US012599354B2

(12) United States Patent
Gopinathan et al.

(10) Patent No.: US 12,599,354 B2
(45) Date of Patent: Apr. 14, 2026

(54) MULTI-SENSOR DEVICE FOR MONITORING HEALTH

(71) Applicant: Analog Devices International Unlimited Company, Limerick (IE)

(72) Inventors: Venugopal Gopinathan, Boston, MA (US); Tony J. Akl, Bedford, MA (US)

(73) Assignee: Analog Devices International Unlimited Company, Limerick (IE)

( * ) Notice: Subject to any disclaimer, the term of this patent is extended or adjusted under 35 U.S.C. 154(b) by 555 days.

(21) Appl. No.: 17/372,979

(22) Filed: Jul. 12, 2021

(65) Prior Publication Data

US 2021/0338190 A1 Nov. 4, 2021

Related U.S. Application Data

(63) Continuation of application No. PCT/EP2020/050813, filed on Jan. 14, 2020.

(Continued)

(30) Foreign Application Priority Data

Jan. 14, 2020 (WO) ................. PCT/EP2020/050813

(51) Int. Cl.
*A61B 7/04* (2006.01)
*A61B 5/00* (2006.01)
(Continued)

(52) U.S. Cl.
CPC .............. *A61B 7/04* (2013.01); *A61B 5/0004* (2013.01); *A61B 5/02055* (2013.01);
(Continued)

(58) Field of Classification Search
CPC ..... A61B 7/04; A61B 5/0004; A61B 5/02055; A61B 5/0531; A61B 5/684
See application file for complete search history.

(56) References Cited

U.S. PATENT DOCUMENTS 3,874,368 A 4/1975 Asrican
4,289,142 A 9/1981 Kearns
(Continued)

FOREIGN PATENT DOCUMENTS

CN 103370004 A 10/2013
CN 103976737 A 8/2014
(Continued)

OTHER PUBLICATIONS

International Search Report and Written Opinion issued in PCT/EP2020/050813 mailed Jul. 21, 2020, 28 pages.
(Continued)

*Primary Examiner* — Carl H Layno
*Assistant Examiner* — Maria Catherine Anthony
(74) *Attorney, Agent, or Firm* — ArentFox Schiff LLP

(57) ABSTRACT

The present invention relates to methods for marking positions for or for positioning of six ECG chest electrodes based on a subject's body height, which allows a reproducible placement of the electrodes in serial independent ECG measurements. The present invention further relates to a device for placement of ECG electrodes which implements said method, and methods and uses applying said device. Hence, the present invention provides an accurate and reproducible, easy to use and low-cost method and device for ECG chest electrode positioning, especially in serial examinations and in obese subjects by minimizing the mistakes in ECG chest electrode placement depending on the subjective and inaccurate defining of anatomic remarks for electrode positions.

10 Claims, 35 Drawing Sheets

Related U.S. Application Data

(60) Provisional application No. 62/923,214, filed on Oct. 18, 2019, provisional application No. 62/792,263, filed on Jan. 14, 2019.

(51) Int. Cl.
| | |
|---|---|
| *A61B 5/0205* | (2006.01) |
| *A61B 5/0531* | (2021.01) |
| *A61B 5/28* | (2021.01) |

(52) U.S. Cl.
CPC .............. *A61B 5/0531* (2013.01); *A61B 5/28* (2021.01); *A61B 5/684* (2013.01); *A61B 2560/0443* (2013.01); *A61B 2560/0475* (2013.01); *A61B 2562/0271* (2013.01)

(56) References Cited

U.S. PATENT DOCUMENTS

| | | | |
|---|---|---|---|
| 4,690,152 A | 9/1987 | Juncosa | |
| 4,917,099 A | 4/1990 | Stice | |
| 5,020,541 A | 6/1991 | Marriott | |
| 5,477,867 A | 12/1995 | Balkanyi | |
| 6,007,532 A | 12/1999 | Netherly | |
| 6,117,077 A | 9/2000 | Del et al. | |
| D443,063 S | 5/2001 | Pisani et al. | |
| D445,507 S | 7/2001 | Pisani et al. | |
| 6,456,872 B1 | 9/2002 | Faisandier | |
| 6,847,836 B1 | 1/2005 | Sujdak | |
| 7,070,568 B1 | 7/2006 | Koh | |
| 7,077,810 B2 | 7/2006 | Lange et al. | |
| 7,226,422 B2 | 6/2007 | Hatlestsad et al. | |
| D598,110 S | 8/2009 | Phillips et al. | |
| D639,437 S | 6/2011 | Bishay et al. | |
| 7,972,276 B1 | 7/2011 | Min | |
| 7,979,115 B2 | 7/2011 | Stahmann et al. | |
| 8,140,154 B2 | 3/2012 | Donnelly et al. | |
| 8,328,718 B2 | 12/2012 | Tran | |
| 8,369,936 B2 | 2/2013 | Farringdon et al. | |
| D682,439 S | 5/2013 | Olson et al. | |
| 8,483,817 B2 | 7/2013 | Anders | |
| D690,021 S | 9/2013 | Olson et al. | |
| D690,824 S | 10/2013 | Olson et al. | |
| 8,626,262 B2 | 1/2014 | Mcgusty et al. | |
| D702,356 S | 4/2014 | Vosch et al. | |
| 8,700,118 B2 | 4/2014 | Oster et al. | |
| 8,831,898 B2 | 9/2014 | Pinter et al. | |
| D718,458 S | 11/2014 | Vosch et al. | |
| 8,892,196 B2 | 11/2014 | Chang | |
| D719,660 S | 12/2014 | Vosch et al. | |
| D744,659 S | 12/2015 | Bishay et al. | |
| D761,436 S | 7/2016 | Fogarty et al. | |
| D766,447 S | 9/2016 | Bishay et al. | |
| 9,579,060 B1 * | 2/2017 | Lisy ......................... A61B 5/16 | |
| D855,191 S | 7/2019 | Hong et al. | |
| D860,465 S | 9/2019 | Lovell et al. | |
| D861,179 S | 9/2019 | Kurachi et al. | |
| D864,400 S | 10/2019 | Benedikter | |
| 10,548,484 B2 | 2/2020 | Brunner et al. | |
| D886,303 S | 6/2020 | Huang et al. | |
| D890,347 S | 7/2020 | Chang et al. | |
| D905,858 S | 12/2020 | Lovell et al. | |
| D914,218 S | 3/2021 | Govari et al. | |
| 10,959,634 B2 | 3/2021 | Varadan et al. | |
| 11,047,821 B2 | 6/2021 | Ano et al. | |
| D932,019 S | 9/2021 | Royea | |
| D932,637 S | 10/2021 | Hsu | |
| D939,710 S | 12/2021 | Olavi | |
| D940,881 S | 1/2022 | Hadley et al. | |
| D967,433 S | 10/2022 | Al-Ali et al. | |
| D969,328 S | 11/2022 | Sun | |
| D970,018 S | 11/2022 | Soosalu et al. | |
| D972,150 S | 12/2022 | Kale et al. | |
| D972,736 S | 12/2022 | Cadena, III | |
| D981,571 S | 3/2023 | Keeman et al. | |
| D997,938 S | 9/2023 | Akl et al. | |
| D1,030,071 S | 6/2024 | Huang et al. | |
| D1,052,089 S | 11/2024 | Sibal et al. | |
| D1,057,167 S | 1/2025 | Zhuang | |
| D1,077,219 S | 5/2025 | Hagerty et al. | |
| D1,090,858 S | 8/2025 | Akl et al. | |
| D1,094,366 S | 9/2025 | Akl et al. | |
| 2003/0100843 A1 | 5/2003 | Hoffman | |
| 2004/0102712 A1 | 5/2004 | Belalcazar et al. | |
| 2004/0122485 A1 | 6/2004 | Stahmann et al. | |
| 2004/0134496 A1 | 7/2004 | Cho et al. | |
| 2005/0101875 A1 | 5/2005 | Semler et al. | |
| 2005/0113661 A1 | 5/2005 | Nazeri et al. | |
| 2006/0064029 A1 | 3/2006 | Shimon | |
| 2006/0247739 A1 | 11/2006 | Wahlstrand et al. | |
| 2007/0010758 A1 | 1/2007 | Matthiessen et al. | |
| 2007/0073168 A1 | 3/2007 | Zhang et al. | |
| 2007/0156061 A1 | 7/2007 | Hess | |
| 2007/0194776 A1 | 8/2007 | Bossche | |
| 2007/0276270 A1 * | 11/2007 | Tran ..................... A61B 5/0022 |
| | | | 600/508 |
| 2008/0001735 A1 | 1/2008 | Tran | |
| 2008/0004904 A1 | 1/2008 | Tran | |
| 2008/0274316 A1 | 11/2008 | Griffith et al. | |
| 2008/0275316 A1 | 11/2008 | Fink et al. | |
| 2009/0069708 A1 | 3/2009 | Hatlestad et al. | |
| 2009/0118626 A1 | 5/2009 | Moon et al. | |
| 2009/0326600 A1 | 12/2009 | Kracker | |
| 2010/0004548 A1 | 1/2010 | Rytky | |
| 2010/0298899 A1 | 11/2010 | Donnelly et al. | |
| 2010/0305633 A1 | 12/2010 | Aziz | |
| 2010/0331713 A1 | 12/2010 | Ostrow | |
| 2011/0001497 A1 | 1/2011 | Chetelat et al. | |
| 2011/0009753 A1 | 1/2011 | Zhang et al. | |
| 2011/0061647 A1 | 3/2011 | Stahmann et al. | |
| 2011/0204971 A1 | 8/2011 | Chang et al. | |
| 2011/0208083 A1 | 8/2011 | Gutfinger | |
| 2011/0237904 A1 | 9/2011 | Kim | |
| 2011/0237922 A1 | 9/2011 | Parker et al. | |
| 2011/0251817 A1 | 10/2011 | Burns et al. | |
| 2011/0257554 A1 | 10/2011 | Banet et al. | |
| 2012/0070707 A1 | 3/2012 | Kim | |
| 2013/0069780 A1 | 3/2013 | Tran et al. | |
| 2013/0108995 A1 | 5/2013 | Depasqua et al. | |
| 2013/0116578 A1 | 5/2013 | An et al. | |
| 2013/0172691 A1 | 7/2013 | Tran | |
| 2013/0190577 A1 | 7/2013 | Brunner et al. | |
| 2013/0338724 A1 | 12/2013 | Joo et al. | |
| 2014/0051962 A1 | 2/2014 | Krusor et al. | |
| 2014/0121257 A1 | 5/2014 | Simpson, Jr. | |
| 2014/0184422 A1 | 7/2014 | Mensinger et al. | |
| 2014/0206948 A1 | 7/2014 | Romem | |
| 2014/0206977 A1 | 7/2014 | Bahney et al. | |
| 2014/0266375 A1 | 9/2014 | Feldman et al. | |
| 2014/0352023 A1 | 12/2014 | Mordecai et al. | |
| 2014/0378849 A1 | 12/2014 | Krimsky et al. | |
| 2015/0068069 A1 | 3/2015 | Tran et al. | |
| 2015/0160185 A1 | 6/2015 | Just et al. | |
| 2016/0022164 A1 | 1/2016 | Brockway et al. | |
| 2016/0066812 A1 | 3/2016 | Cheng et al. | |
| 2016/0135715 A1 | 5/2016 | Seppäet al. | |
| 2016/0195484 A1 | 7/2016 | Emery | |
| 2016/0275776 A1 | 9/2016 | Shen et al. | |
| 2016/0287174 A1 | 10/2016 | Joseph | |
| 2017/0281095 A1 | 10/2017 | An et al. | |
| 2018/0070824 A1 | 3/2018 | Cronin et al. | |
| 2018/0116626 A1 | 5/2018 | Darbari et al. | |
| 2018/0309096 A1 | 10/2018 | Kim et al. | |
| 2018/0325407 A1 | 11/2018 | Varadan et al. | |
| 2019/0021633 A1 | 1/2019 | Wang et al. | |
| 2019/0022400 A1 | 1/2019 | Kumar et al. | |
| 2019/0059777 A1 | 2/2019 | Aga et al. | |
| 2019/0167176 A1 | 6/2019 | Annoni et al. | |
| 2019/0223782 A1 | 7/2019 | Wen et al. | |
| 2020/0038708 A1 | 2/2020 | Cheu et al. | |
| 2020/0196878 A1 | 6/2020 | Bentzion et al. | |
| 2020/0329977 A1 | 10/2020 | Freeman et al. | |
| 2020/0397315 A1 | 12/2020 | Raj et al. | |
| 2021/0153837 A1 | 5/2021 | Jones | |

(56) References Cited

U.S. PATENT DOCUMENTS

| | | |
|---|---|---|
| 2021/0333759 A1 | 10/2021 | Vasavada et al. |
| 2021/0386318 A1 | 12/2021 | Rahman et al. |
| 2021/0401317 A1 | 12/2021 | Olivier |
| 2022/0031253 A1 | 2/2022 | Burnes et al. |
| 2022/0233241 A1 | 7/2022 | Shelton, IV et al. |
| 2022/0344025 A1 | 10/2022 | Bort et al. |
| 2023/0061046 A1 | 3/2023 | Lim et al. |
| 2023/0200710 A1 | 6/2023 | Thakur et al. |

FOREIGN PATENT DOCUMENTS

| | | | | |
|---|---|---|---|---|
| CN | 104138259 A | 11/2014 | | |
| CN | 107957542 A | 4/2018 | | |
| CN | 108209914 A | 6/2018 | | |
| CN | 105286909 B | 2/2019 | | |
| EP | 1923952 | 5/2008 | | |
| EP | 3153099 A1 | 4/2017 | | |
| EP | 2603138 B1 | 11/2017 | | |
| GB | 6392893 | 10/2024 | | |
| JP | 2007-027103 A | 2/2007 | | |
| JP | 2010-282824 A | 12/2010 | | |
| JP | 2012-074265 A | 4/2012 | | |
| JP | 2013-540523 A | 11/2013 | | |
| JP | 2016-517324 A | 6/2016 | | |
| JP | 2016-154864 A | 9/2016 | | |
| JP | 2019-530550 A | 10/2019 | | |
| JP | 2023-177220 A | 12/2023 | | |
| KR | 10-2009-0124140 A | 12/2009 | | |
| KR | 10-2513594 B1 | 3/2023 | | |
| TW | 201626950 A | 8/2016 | | |
| WO | 0007013 | 2/2000 | | |
| WO | WO-2005044090 A2 * | 5/2005 | ......... | A61B 5/02055 |
| WO | 2009/148425 A1 | 12/2009 | | |
| WO | 2012/021900 A1 | 2/2012 | | |
| WO | 2013176861 | 11/2013 | | |
| WO | 2014/021883 A1 | 2/2014 | | |
| WO | 2014/145487 A1 | 9/2014 | | |
| WO | 2016/040879 A1 | 3/2016 | | |
| WO | 2017214198 | 12/2017 | | |
| WO | WO-2017214198 A1 * | 12/2017 | ........... | A61B 5/0002 |
| WO | 2018140509 | 8/2018 | | |
| WO | 2018/217017 A2 | 11/2018 | | |
| WO | 2020/047607 A1 | 3/2020 | | |
| WO | 2020/148280 A2 | 7/2020 | | |
| WO | 2021/110937 A1 | 6/2021 | | |

OTHER PUBLICATIONS

Bera, Tushar Kanti, "Bioelectrical Impedance Methods for Noninvasive Health Monitoring: A Review," Journal of Medical Engineering, vol. 2014, Article ID 381251, 2014, 28 pages.

Blanco-Almazan et al., "Wearable Bioimpedance Measurement for Respiratory Monitoring During Inspiratory Loading", In Proceedings of IEEE Access, vol. 7, Jul. 5, 2019, pp. 89487-89496.

EP Search Report issued in EP Patent Application Serial No. 18744790.0 mailed Aug. 14, 2020, 9 pages.

Extended European Search Report received for European Patent Application No. 24194357.0, mailed on Jan. 23, 2025, 9 pages.

Grenvik et al., "Impedance Pneumography: Comparison between Chest Impedance Changes and Respiratory Volumes in 11 Healthy Volunteers", In Journal of Chest, vol. 62, Issue 4, Oct. 1972, pp. 439-443.

Hamilton et al., "Impedance measurement of tidal volume and ventilation", In Journal of Applied Physiology, vol. 20, No. 3, May 1965, 4 pages.

International Search Report and Written Opinion received for PCT Patent Application No. PCT/US2018/15067, mailed on May 8, 2018, 12 pages.

Kubota et al. Effects of trunk posture in Fowlers position on hemodynamics, Autonom Neurosci Basic Clin 2015; 189: 56-59. ( Year: 2015).

Spooner et al. Head-of-bed elevation improves end-expiratory lung volumes in mechanically ventilated subjects: a prospective observational study, Respir Care 2014;59(10): 1583-1589. (Year: 2014).

Seppa et al., "Assessment of Pulmonary Flow Using Impedance Pneumography", In Proceedings of IEEE Transactions on Biomedical Engineering, vol. 57, Issue 9, Sep. 2010, pp. 2277-2285.

Seppa et al., "Novel electrode configuration for highly linear impedance pneumography", In Journal of Biomed Tech., vol. 58, Issue 1, Feb. 2013, pp. 35-38.

Bera, T. K., "Bioelectrical Impedance and The Frequency Dependent Current Conduction Through Biological Tissues: A Short Review," IOP Conference Series: Materials Science and Engineering, 012005, vol. 331, 2018, pp. 1-9.

Broeders, Jan-Hein, "Wearable Electronic Devices Monitor Vital Signs, Activity Level, and More", Analog Dialogue, vol. 48, Dec. 2014, pp. 1-6.

DAIC, "Medtronic Launches SEEQ Wearable Cardiac Monitoring System in United States", Medtronic Monitor, Available online at: <https://www.dicardiology.com/product/medtronic-launches-seeq-wearable-cardiac-monitoring-system-united-states>, Oct. 7, 2014, pp. 1-6.

Demidenko, E., "An Analytic Solution to the Homogeneous EIT Problem on the 2d Disk and Its Application to Estimation of Electrode Contact Impedances", NIH Public Access, Author Manuscript, Physiological Measurement, PMC, Sep. 1, 2012, pp. 1-24.

Extended European Search Report received for European Patent Application No. 25154192.6, mailed on Jun. 30, 2025, 9 pages.

International Preliminary Report on Patentability received for PCT Application No. PCT/EP2020/050813, mailed Jun. 16, 2021, 15 pages.

International Preliminary Report on Patentability received for PCT Patent Application No. PCT/EP2020/050545, mailed on Jul. 22, 2021, 11 pages.

International Preliminary Report on Patentability received for PCT Patent Application No. PCT/EP21/082219, mailed on Jun. 1, 2023, 9 pages.

International Preliminary Report on Patentability received for PCT Patent Application No. PCT/US2018/015067, mailed on Aug. 8, 2019, 7 pages.

International Search Report and Written Opinion received for PCT Patent Application No. PCT/EP2020/050545, mailed Mar. 31, 2020, 13 pages.

International Search Report and Written Opinion received for PCT Patent Application No. PCT/EP2021/082219, mailed on Mar. 31, 2022, 11 pages.

International Search Report and Written Opinion received for PCT Patent Application No. PCT/EP2025/055429, mailed on May 6, 2025, 14 pages.

International Search Report and Written Opinion received for PCT Patent Application No. PCT/US2025/027751, mailed on Jul. 28, 2025, 14 pages.

Partial European Search Report received for European Patent Application No. 25154190.0, mailed on Jun. 30, 2025, 12 pages.

Partial European Search Report received for European Patent Application No. 25154191.8, mailed on Jun. 30, 2025, 14 Pages.

U.S. Appl. No. 29/901,773, filed Sep. 5, 2023.

Quad Industries, "Smart Health Patches to Run Smart", Available from internet URL: <https://www.quad-ind.com/smart-health-patches-to-run-smart/>, 2026, 7 pages.

Schieszer, John, "Wearable Medical Monitoring Devices: The Innovation Continues", Available from internet URL: <https://www.renalandurologynews.com/features/wearable-medical-monitoring-devices-the-innovation-continues/>, Oct. 31, 2022, 3 pages.

Extended European Search Report received for Patent Application No. 25154191.8, mailed on Nov. 17, 2025, 12 pages.

Mlynczak et al., "Motion Artifact Detection in Respiratory Signals based on Teager Energy Operator and Accelerometer Signals", IFMBE Proceedings, vol. 65, 2017, pp. 45-48.

* cited by examiner

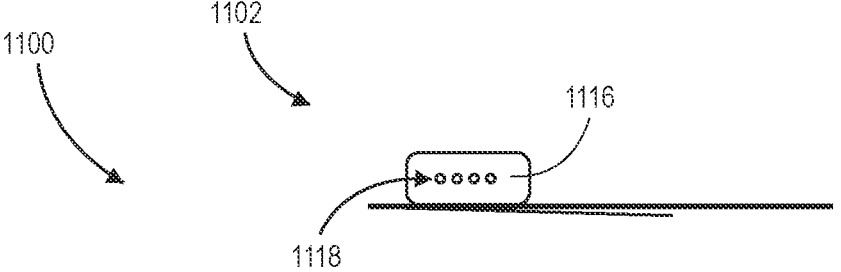
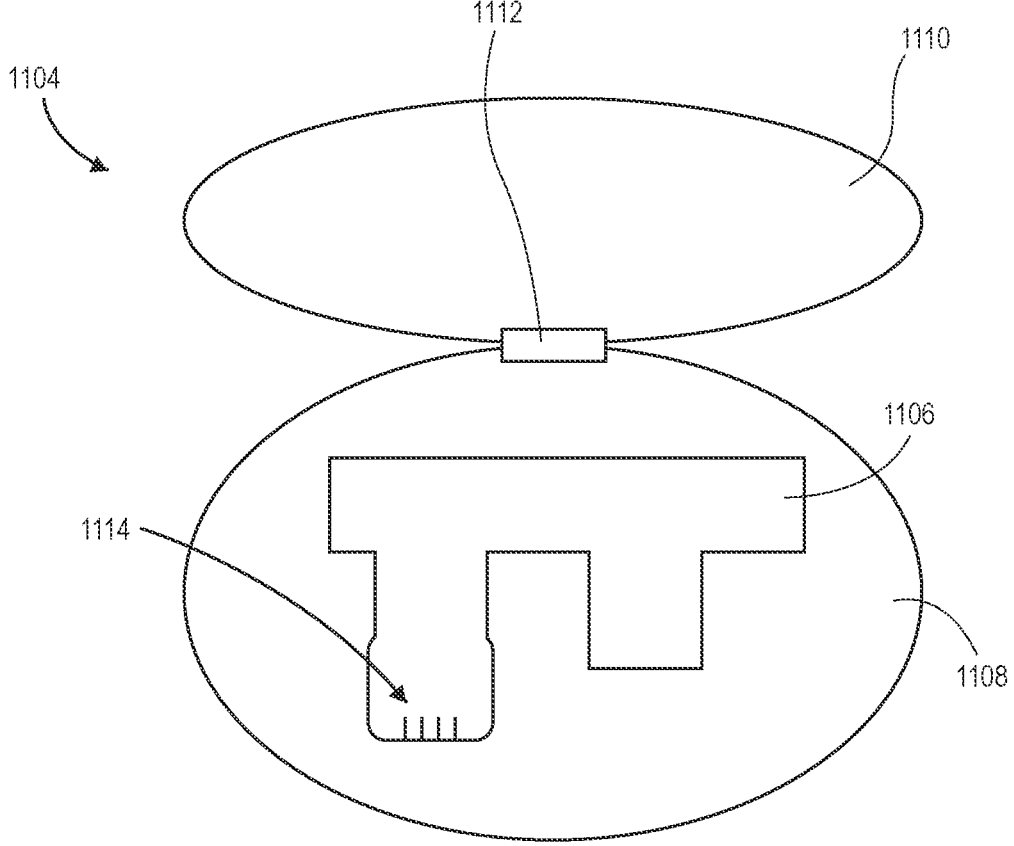
FIG. 11

1200

1204

1202

1300

1306    1308b    1308c     1308a    1308

1304

1302

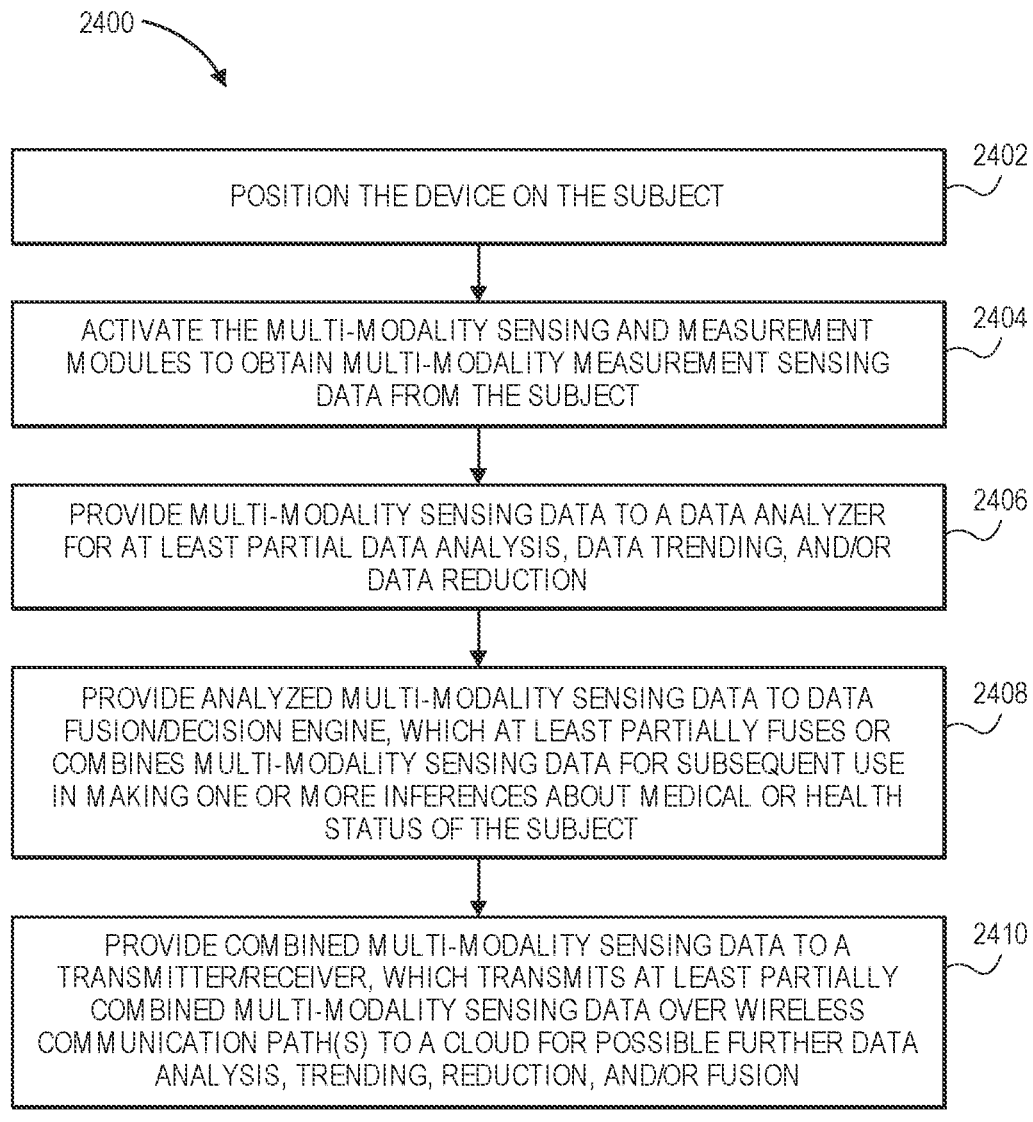

2400

2402
POSITION THE DEVICE ON THE SUBJECT

2404
ACTIVATE THE MULTI-MODALITY SENSING AND MEASUREMENT MODULES TO OBTAIN MULTI-MODALITY MEASUREMENT SENSING DATA FROM THE SUBJECT

2406
PROVIDE MULTI-MODALITY SENSING DATA TO A DATA ANALYZER FOR AT LEAST PARTIAL DATA ANALYSIS, DATA TRENDING, AND/OR DATA REDUCTION

2408
PROVIDE ANALYZED MULTI-MODALITY SENSING DATA TO DATA FUSION/DECISION ENGINE, WHICH AT LEAST PARTIALLY FUSES OR COMBINES MULTI-MODALITY SENSING DATA FOR SUBSEQUENT USE IN MAKING ONE OR MORE INFERENCES ABOUT MEDICAL OR HEALTH STATUS OF THE SUBJECT

2410
PROVIDE COMBINED MULTI-MODALITY SENSING DATA TO A TRANSMITTER/RECEIVER, WHICH TRANSMITS AT LEAST PARTIALLY COMBINED MULTI-MODALITY SENSING DATA OVER WIRELESS COMMUNICATION PATH(S) TO A CLOUD FOR POSSIBLE FURTHER DATA ANALYSIS, TRENDING, REDUCTION, AND/OR FUSION

FIG. 24 feedback loop feedback loop to
the heart to
the artery

*Medical classifications of heart failure*

MULTI-SENSOR DEVICE FOR MONITORING HEALTH

RELATED APPLICATIONS

The present disclosure claims priority to, as a bypass continuation, International Patent Application Serial No. PCT/EP2020/050813, entitled "MULTI-SENSOR DEVICE FOR MONITORING HEALTH" and filed Jan. 14, 2020. The International Patent application claims priority to and receives benefit of U.S. Provisional Application No. 62/923,214 entitled "MULTI-SENSOR DEVICE FOR MONITORING HEALTH" and filed Oct. 18, 2019, and U.S. Provisional Application No. 62/792,263 entitled "MULTI-SENSOR DEVICE FOR MONITORING HEALTH" and filed Jan. 14, 2019, the disclosures of which are incorporated by reference in their entireties.

FIELD OF THE DISCLOSURE

The present application relates generally to systems, apparatus, and methods of managing medical or health conditions in human subjects, and more specifically to systems, apparatus, and methods of non-invasively detecting and monitoring medical or health conditions, such as congestive heart failure (CHF), chronic obstructive pulmonary disease (COPD), and other chronic conditions in human subjects that employ multiple modalities of sensing.

BACKGROUND

In human subjects, congestive heart failure (CHF) is a known cardiac condition in which a damaged heart muscle loses its ability to pump sufficient amounts of blood to meet the body's demands. In the early stages of CHF, such an inability to pump sufficient amounts of blood may occur only while a human subject exercises. However, in more advanced stages of CHF, such an inability to pump sufficient amounts of blood may occur even while the human subject is at rest. CHF is one of the most commonly diagnosed cardiac conditions in hospital patients over the age of 65, and one of the most frequent reasons for such patients' readmission to hospitals in a time duration of 30 days. In recent years, 30-day hospital readmission expenses for CHF have increased to $1.8 billion per year, with approximately $13,000 being allotted for each readmission at a 25% readmission rate. Some of the reasons for such patients' readmission to hospitals can include, but are not limited to: (1) patient non-compliance with regard to diet and medication, which can result in excess fluid in the lungs or extreme dehydration, (2) incomplete titration of medication dosages, which often need to be modified as a patient moves from the hospital environment back to his or her home, and (3) atrial fibrillation, which can onset after the patient's discharge from the hospital.

Management of CHF in patients following discharge from the hospital has traditionally focused on monitoring the patients' fluid retention using sensors incorporated in implantable cardiac devices, such as implantable cardioverter defibrillators (ICDs), cardiac resynchronization therapy-defibrillators (CRT-Ds), or pacemakers. Such implantable cardiac devices can detect developing pulmonary congestion in a patient by measuring the patient's thoracic fluid impedance. For example, an implantable cardiac device such as an ICD, CRT-D, or pacemaker can be configured to pass an electrical current across a patient's lung, and to measure the resulting intra-thoracic impedance.

As the patient's thoracic fluid accumulates during pulmonary congestion, conductance across the patient's lung increases, causing a corresponding decrease in impedance indicative of the level of thoracic fluid accumulation. Such implantable cardiac devices can also be interrogated by hospital clinicians, allowing the hospital clinicians to monitor the patient's fluid status and to receive early warnings of changes that may signal an impending fluid overload. Based on the patient's monitored fluid status, the hospital clinicians may then determine whether or not it would be appropriate to readmit the patient to the hospital for further monitoring and/or treatment.

SUMMARY OF THE DISCLOSURE

Systems, methods, and devices for non-invasively detecting and/or monitoring medical conditions are disclosed. The medical conditions that may be detected and/or monitored may include chronic conditions, such as congestive heart failure (CHF), chronic obstructive pulmonary disease (COPD), other cardiac conditions, and other pulmonary conditions. According to some implementations, a device for non-invasively detecting and monitoring medical conditions using multiple modalities of sensing, comprises at least two electrodes configured to be positioned on a subject, an acoustic sensor configured to be positioned on a subject, a thoracic impedance measurement module connected to the at least two electrodes for measuring a first impedance between the at least two electrodes, and a heart acoustic measurement module connected to the acoustic sensor for detecting and measuring a heart sound from the acoustic sensor. In some implementations, the heart sound is an S3 heart sound. In other implementations, the heart sound is an S4 heart sound. In various implementations, the acoustic sensor is at least one of an ultrasound sensor and a piezoelectric microphone sensor. In some implementations, the at least two electrodes include two electrode pairs, and each electrode pair includes a force electrode and a sense electrode. The force electrode is configured to apply an electrical force (such as a current or voltage) to the subject and the sense electrode is configured to sense changes caused by the applied electrical force. The changes may include changes in a voltage drop between the electrodes and/or electrode pairs, changes in current flow between the electrodes and/or electrode pairs, changes in conductance between the electrodes and/or electrode pairs, or some combination thereof.

In some implementations, the device includes a sensor for determining an orientation of the device. In one implementation, the thoracic impedance measurement module measures the first impedance when the device is in a first orientation, and measures a second impedance when the device is in a second orientation. In one example, a first orientation indicates that the device is approximately horizontal, and the second orientation indicates that the device is approximately vertical. In another example, a first orientation indicates that the device is approximately horizontal, and the second orientation indicates that the device is positioned at an angle of between about 30 degrees and about 90 degrees with respect to the horizontal plane. In another example, a first orientation indicates that the device is approximately horizontal, and the second orientation indicates that the device is positioned at an angle greater than about 30 degrees with respect to the horizontal plane. In one example, the second orientation indicates that the device is in a Fowler's position. In some implementations, the thoracic impedance measurement module automatically measures the first impedance at regular intervals.

In some implementations, the device further comprises an electrocardiogram measurement module, connected to the electrodes, for measuring electrical activity between the electrodes.

According to some implementations, a system for non-invasively detecting and monitoring medical conditions using multiple modalities of sensing, comprises a device positioned on a subject having a plurality of surface sensors and a plurality of sensing modules connected to the plurality of surface sensors, configured to gather multi-modality sensing data, and a data analyzer operative to perform at least one of data analysis, data trending, and data reduction of the multi-modality sensing data. The multi-modality sensing data includes a first impedance between at least two of the surface sensors, and heart sounds from at least one of the surface sensors of the plurality of surface sensors. In various implementations, the surface sensors include at least one of electrodes, heart sounds sensors, ultrasound sensors, and photoplethysmography sensors.

In some implementations, the system further includes a data decision engine configured to combine at least some of the multi-modality sensing data, wherein the combined multi-modality sensing data indicates a medical condition status of the subject. In some implementations, the system further includes a transceiver configured to transmit the combined multi-modality sensing data over at least one wireless communication path to a cloud for further processing.

In some implementations, the device in the system further comprises a sensor for determining an orientation of the device. In some implementations, the device includes a thoracic impedance measurement module configured to measure the first impedance when the device is in a first orientation and a second impedance between the at least two of the surface sensors when the device is in a second orientation. In some implementations, the device in the system further comprises an electrocardiogram measurement module connected to the plurality of surface sensors, the electrocardiogram measurement module for measuring electrical activity between at least two of the surface sensors.

According to some implementations, a method for non-invasively detecting and monitoring medical conditions using multiple modalities of sensing comprises transmitting a current transcutaneously from a first electrode positioned on a subject, receiving a current transcutaneously at a second electrode positioned on the subject, measuring a voltage between the first and second electrodes, determining a thoracic impedance at least based on the voltage, receiving an acoustic signal from an acoustic sensor, measuring a heart sound from the acoustic sensor, and transmitting thoracic impedance data and heart sound measurements to a data analyzer configured to perform at least one of data analysis, data trending, and data reduction of the thoracic impedance data and heart sound measurements. In some implementations, the method further comprises measuring electrical activity between the first electrode and the second electrode and producing an electrocardiogram.

In some implementations, the method further comprises determining an orientation of the device. In some implementations, the thoracic impedance is determined when the device is in a first orientation and the method further comprises determining a second impedance measurement between the first electrode and the second electrode when the device is in a second orientation.

In accordance with the present application, systems, apparatus, and methods are disclosed for non-invasively detecting and monitoring medical or health conditions (such as chronic conditions, including CHF), in human subjects using multiple modalities of sensing, including, but not limited to, thoracic impedance sensing, electrocardiogram (ECG) sensing, breath rate sensing, tidal volume sensing, heart sounds sensing, pulse oximetry sensing, blood pressure (systolic, diastolic) sensing, cardiac output sensing, etc. The disclosed systems, apparatus, and methods can non-invasively gather and at least partially analyze, trend, and/or reduce data from each modality of sensing, and perform data fusions on some or all of the multi-modality sensing data in order to obtain curated data useful in detecting the onset of chronic conditions in a human subject and/or monitor the severity. The disclosed systems, apparatus, and methods can also transmit such multi-modality sensing data (as well as other information pertaining to the onset and/or severity of the human subject's chronic conditions) either directly over a communications network to the "cloud," or to a smartphone or other communications device, which, in turn, can transmit the multi-modality sensing data and/or other information over the communications network to the cloud. The multi-modality sensing data can also be analyzed, trended, reduced, and/or fused in the cloud to augment or at least partially replace the data analysis, trending, reduction, and/or fusion performed by the disclosed systems, apparatus, and methods. The resulting curated multi-modality sensing data and/or other information may then be remotely downloaded from the cloud by hospital clinicians for monitoring and/or tracking purposes. By non-invasively gathering and analyzing data from multiple modalities of sensing to detect the onset of chronic conditions and/or monitor the severity in human subjects, the disclosed systems, apparatus, and methods can increase the positive detection of potentially problematic chronic conditions while decreasing false positives, which can reduce the number of unnecessary hospital readmissions, shorten hospital stays, and reduce hospital costs.

In certain embodiments, a method of non-invasively detecting and monitoring medical or health conditions such as chronic conditions, including congestive heart failure (CHF), in human subjects using multiple modalities of sensing includes positioning a non-invasive chronic condition detection and monitoring device on a human subject such that it makes contact with the human subject's torso and upper chest and neck areas or any other suitable parts or areas of the body, via at least a plurality of surface electrodes and/or one or more sensors such as heart sound sensors, ultrasound sensors, photoplethysmography (PPG) sensors, etc. Once the chronic condition detection and monitoring device is positioned in contact with the human subject's torso and upper chest and neck areas, a plurality of multi-modality sensing and measurement modules contained in the chronic condition detection and monitoring device are activated to obtain multi-modality sensing data from the human subject. The multi-modality sensing data can include, but are not limited to, one or more of thoracic impedance sensing data, electrocardiogram (ECG) sensing data, breath rate and tidal volume sensing data, heart rate variability/heart sounds-based sensing data, and pulse oximetry sensing data. The multi-modality sensing data are provided to a data analyzer contained in the chronic condition detection and monitoring device for at least partially analyzing, trending, and/or reducing the data. Next, the analyzed multi-modality sensing data are at least partially fused or combined by a data fusion/decision engine contained in the chronic condition detection and monitoring device for subsequent use in making one or more inferences about the chronic condition status of the human subject. The at least partially fused or combined multi-modality sensing data are then transmitted by a transmitter/receiver contained in the chronic condition detection and monitoring device over one or more wireless communication paths to the cloud for possible further data analysis, trending, reduction, and/or fusion, as well as subsequent remote downloading by hospital clinicians for monitoring and/or tracking purposes.

In certain further embodiments, an apparatus for non-invasively detecting and monitoring medical or health conditions such as chronic conditions in human subjects using multiple modalities of sensing includes a non-invasive chronic condition detection and monitoring device configured to be positioned on a human subject, thereby making contact with the human subject's torso and upper chest and neck areas or any other suitable parts or areas of the body, via at least a plurality of surface electrodes and/or one or more sensors, such as heart sound sensors, ultrasound sensors, photoplethysmography (PPG) sensors, etc. The chronic condition detection and monitoring device includes a plurality of multi-modality sensing and measurement modules, a data analyzer, a data fusion/decision engine, and a transmitter/receiver. The plurality of multi-modality sensing and measurement modules are operative to obtain multi-modality sensing data from the human subject, including, but not limited to, one or more of thoracic impedance sensing data, ECG sensing data, breath rate and tidal volume sensing data, heart rate variability/heart sounds-based sensing data, and pulse oximetry sensing data. The data analyzer is operative to perform at least partial data analysis, data trending, and/or data reduction on the multi-modality sensing data. The data fusion/decision engine is operative to at least partially fuse or combine the analyzed multi-modality sensing data for subsequent use in making one or more inferences about the chronic condition status of the human subject. The transmitter/receiver is operative to transmit the at least partially fused or combined multi-modality sensing data over one or more wireless communication paths to the cloud for possible further data analysis, trending, reduction, and/or fusion, as well as subsequent remote downloading by hospital clinicians for monitoring and/or tracking purposes.

Other features, functions, and aspects of the present application will be evident from the description that follows.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 11 illustrates an example system utilized for non-invasively detecting and monitoring medical or health conditions, according to some embodiments of the disclosure;

FIG. 24 is a flow diagram illustrating an example method of detecting the onset of a medical or health condition and/or monitoring its severity, according to some embodiments of the disclosure;

DESCRIPTION OF EXAMPLE EMBODIMENTS OF THE DISCLOSURE

Figure 1:
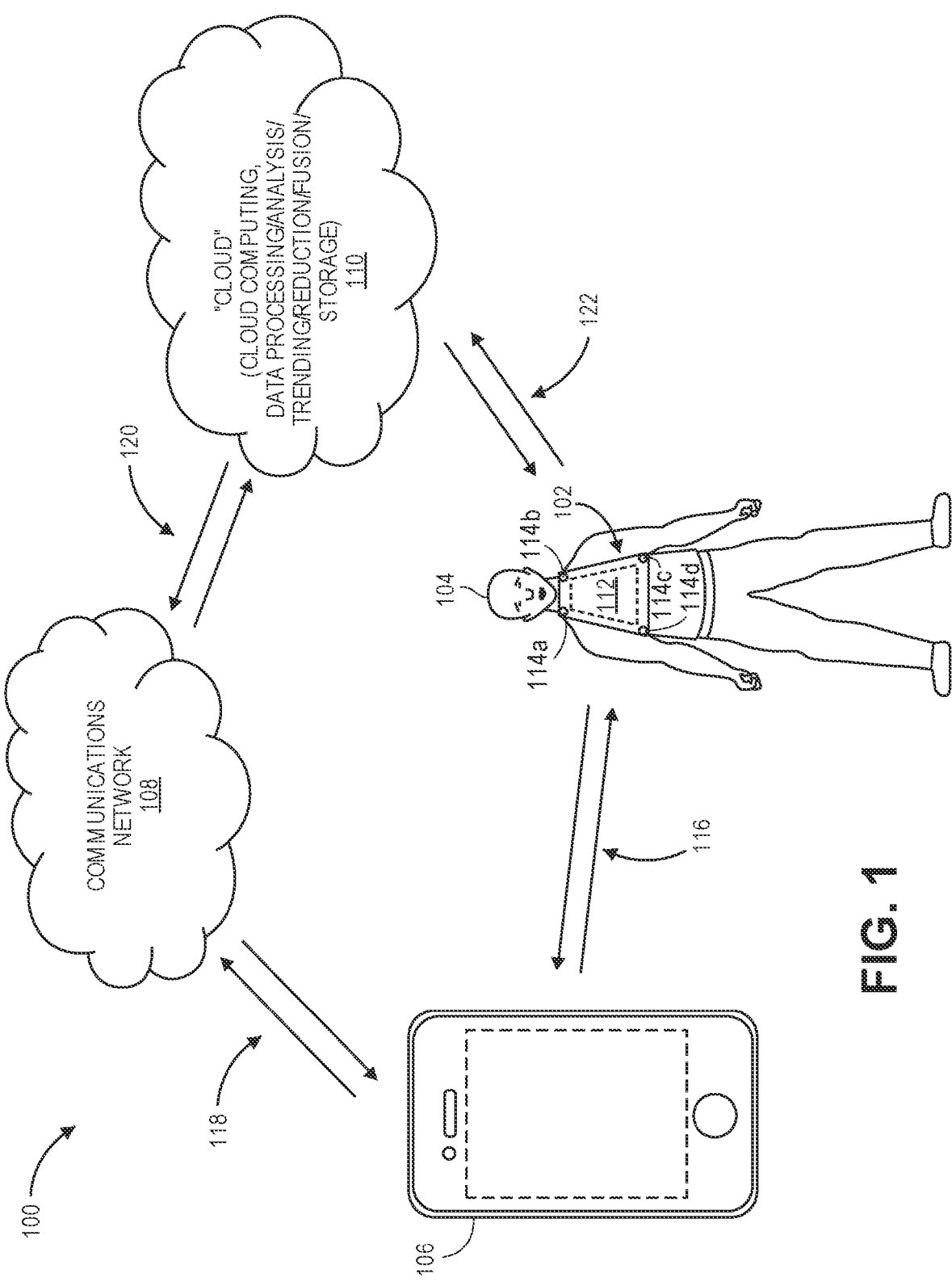
FIG. 1 is a diagram illustrating an environment including an example system for non-invasively detecting and monitoring medical or health conditions of a subject using multiple modalities, according to some embodiments of the disclosure.

Systems, apparatus, and methods are disclosed for non-invasively detecting and monitoring medical or health conditions such as congestive heart failure (CHF) conditions, chronic obstructive pulmonary disease (COPD), and other chronic conditions in human subjects using multiple modalities of sensing. In particular, a device for non-invasively gathering and analyzing, trending, and/or reducing data from each modality of sensing is disclosed. The device can perform data fusions on some or all of the multi-modality sensing data to obtain curated data useful in detecting the onset of a health condition in a human subject and/or monitor its severity, and transmit such multi-modality sensing data (as well as other information pertaining to the onset and/or severity of the human subject's health condition). The data can be transmitted either directly over a communications network to the "cloud," or to a smartphone or other communications device. A smartphone or other communication device can analyze the data locally, or the smartphone or other communication device can transmit the multi-modality sensing data and/or other information over the communications network to the cloud. Data transmitted to the cloud can be remotely analyzed, trended, reduced, and/or fused to augment or at least partially replace the data analysis, trending, reduction, and/or fusion performed by the disclosed systems, apparatus, and methods. In some examples, hospital clinicians can remotely download the resulting curated multi-modality sensing data and/or other information from the cloud for monitoring and/or tracking the health status of the human subject.

The disclosed systems, apparatus, and methods for non-invasively detecting and monitoring chronic conditions in human subjects using multiple modalities of sensing can provide improvements over conventional implantable cardiac devices for managing chronic conditions in human subjects, such as implantable cardioverter defibrillators (ICDs), cardiac resynchronization therapy-defibrillators (CRT-Ds), or pacemakers. For example, such conventional implantable cardiac devices typically include one or more sensors configured to provide a single or limited number of sensing modalities, such as a modality for detecting a human subject's fluid retention. However, monitoring and/or tracking the chronic condition status of a human subject based on just a single or limited number of sensing modalities can often lead to false positives, resulting in unnecessary hospital readmissions that can increase hospital costs. Further, such conventional implantable cardiac devices are generally incapable of analyzing the interrelationship of multi-modality sensing data to obtain positive detection of potentially problematic chronic conditions in human subjects. Moreover, the implantable nature of such conventional cardiac devices can increase surgical risks, as well as the incidence of infection. Additionally, the implantable nature of such conventional cardiac devices limits the availability of the devices to patients, since only patients qualified for the surgery to insert the implant can receive the device.

The disclosed systems, apparatus, and methods for non-invasively detecting and monitoring medical or health conditions (such as chronic conditions, including CHF, COPD, other cardiac conditions, and other pulmonary conditions) in human subjects can non-invasively gather data, and at least partially analyze, trend, and/or reduce data from multiple modalities of sensing. Additionally, the systems, apparatus, and methods can perform data fusions on some or all of the multi-modality sensing data and obtain curated data useful in detecting the onset of chronic conditions, and also useful in monitoring the severity of chronic conditions in human subjects. The disclosed systems, apparatus, and methods thereby increase the positive detection of potentially problematic chronic conditions while decreasing false positives, which can reduce the number of unnecessary hospital readmissions, shorten hospital stays, and reduce hospital costs. Moreover, the disclosed systems, apparatus, and methods for non-invasively detecting and monitoring chronic conditions can be implemented in an external device that can be conveniently employed by a human subject following discharge from the hospital, allowing the human subject as well as hospital clinicians to monitor the subject's chronic condition status with reduced risks from surgery and/or infection.

Worsening heart failure is correlated with changes over time in multiple measurements that can be gathered using the non-invasive systems, apparatus, and methods disclosed herein. In particular, worsening heart failure is correlated with an increase in amplitude of the S3 heart sound, increasingly rapid and shallow breathing at rest, a decrease in the relative tidal volume (the lung volume representing the volume of air displaced between inhalation and exhalation at rest), and a decrease in thoracic impedance.

FIG. 1 depicts a typical environment 100 in which an illustrative embodiment of an example system 102 for non-invasively detecting and monitoring medical or health conditions (such as chronic conditions, including CHF) in human subjects using multiple modalities of sensing may be employed, according to some embodiments of the disclosure. As shown in FIG. 1, the system 102 includes a plurality of multi-modality sensing and measurement modules 112 (see also FIG. 2), and a plurality of surface electrodes/sensors 114*a*-114*d* (e.g., four (4) surface electrodes/sensors, or any other suitable number of surface electrodes/sensors). For example, one or more of the surface electrodes can be implemented as solid-gel surface electrodes, or any other suitable surface electrodes. Further, one or more of the sensors can be implemented as heart sound sensors, ultra-sound sensors, photoplethysmography (PPG) sensors, or any other suitable sensors. The system 102 can be configured as a generally triangular-shaped device, or any other suitably shaped device, operative to contact one or more of the torso, upper chest, and neck areas, or any other suitable parts or areas of the body, of a human subject 104 via at least the plurality of surface electrodes/sensors 114*a*-114*d*.

In various implementations, the system 102 can have a configuration that allows it to be implemented within a wearable vest-like structure, as multiple patch-like devices, or any other suitable structure or device(s). Various examples of device configurations are shown in FIGS. 4A-8, FIG. 10, FIGS. 14-18, and FIG. 25.

In the typical environment 100, the system 102 is operative to engage in bidirectional communications over wireless communication paths 116 with a smartphone 106, which, in turn, is operative to engage in bidirectional communications over wireless communication paths 118 with a communications network 108 (e.g., the Internet). The smartphone 106 is further operative, via the communications network 108, to engage in bidirectional communications over wireless communication paths 120 with the cloud 110, which can include resources for cloud computing, data processing, data analysis, data trending, data reduction, data fusion, data storage, and/or other functions. The system 102 is further operative to engage in bidirectional communications over wireless communication paths 122 directly with the cloud 110.

Figure 2:
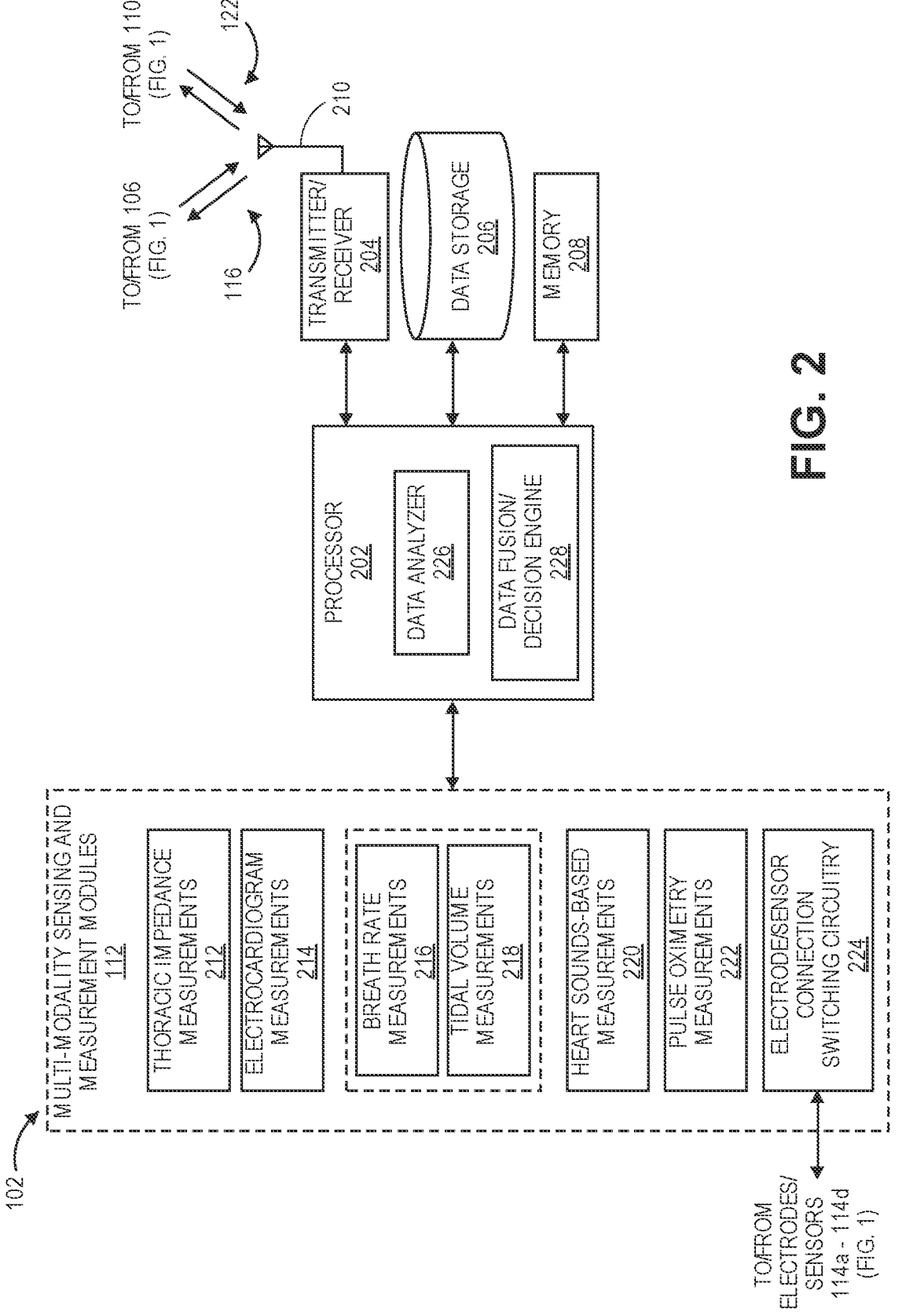
FIG. 2 is a diagram illustrating example functional components of the system of FIG. 1, according to some embodiments of the disclosure.

FIG. 2 depicts a detailed view of the system 102 for non-invasively detecting and monitoring medical or health conditions (such as chronic conditions, including CHF, COPD, other cardiac conditions, and/or other pulmonary conditions) in human subjects, according to some embodiments of the disclosure. As shown in FIG. 2, the system 102 includes the plurality of multi-modality sensing and measurement modules 112, a processor 202 and its associated memory 208, a data storage 206 for storing multi-modality sensing data, and a transmitter/receiver 204. The transmitter/receiver 204 can be configured to perform Bluetooth communications, WiFi communications, or any other suitable short-range communications for communicating with the smartphone 106 (see FIG. 1) over the wireless communication paths 116. The transmitter/receiver 204 can be further configured to perform cellular communications or any other suitable long-range communications for communicating with the cloud 110 (see FIG. 1) over the wireless communication paths 122.

In some implementations, the plurality of multi-modality sensing and measurement modules 112 can include, but are not limited to, one or more of a thoracic impedance measurement module 212, an electrocardiogram (ECG) measurement module 214, a breath rate measurement module 216 and a tidal volume measurement module 218, a heart sounds-based measurement module 220, and a pulse oximetry measurement module 222. In one embodiment, the system 102 can be configured to perform reflective pulse oximetry measurements. In another embodiment, the system 102 can include a finger-pocket device (not shown) for performing finger-based pulse oximetry measurements. The plurality of multi-modality sensing and measurement modules 112 further include electrode/sensor connection switching circuitry 224 for switchably making connections with the plurality of surface electrodes/sensors 114a-114d shown in FIG. 1.

The processor 202 can include a plurality of processing modules such as a data analyzer 226 and a data fusion/decision engine 228. The transmitter/receiver 204 can include at least one antenna 210 operative to transmit/receive wireless signals such as Bluetooth or WiFi signals over the wireless communications paths 116 to/from the smartphone 106, which can be a Bluetooth or WiFi-enabled smartphone or any other suitable smartphone. The antenna 210 is further operative to transmit/receive wireless signals such as cellular signals over the wireless communications paths 122 to/from the cloud 110.

The operation of the system 102 for non-invasively detecting and monitoring medical or health conditions such as chronic conditions, including CHF, COPD, other cardiac conditions, and/or other pulmonary conditions, in human subjects using multiple modalities of sensing will be further understood with reference to the following illustrative example, as well as FIGS. 1 and 2. In this illustrative example, at fixed times each day for a predetermined number of days (e.g., twice a day) while the human subject 104 is in a supine or upright position, the human subject 104 (see FIG. 1) or a human assistant positions the system 102 configured as the generally triangular-shaped device (or any other suitably shaped device) such that it makes contact with one or more of the subject's torso and upper chest and neck areas (or any other suitable parts or areas of the body) via the plurality of surface electrodes/sensors 114a-114d.

Having positioned the system 102 in contact with the human subject's torso and/or upper chest and/or neck areas, the plurality of multi-modality sensing and measurement modules 112 can be activated to gather, collect, sense, measure, or otherwise obtain multi-modality sensing data from the human subject 104. For example, the thoracic impedance measurement module 212 can perform thoracic impedance sensing using multiple vectors to obtain a measure of the human subject's thoracic fluid impedance, as well as trends for obtaining a localization of fluid congestion in the lungs. To that end, the thoracic impedance measurement module 212 can apply, via the electrode/sensor connection switching circuitry 224, a suitable high frequency, low amplitude current between two or more of the surface electrodes 114a-114d. In one example, the current is applied between two of the electrodes 114a-114d at the neck and thorax of the human subject, such as being applied via the surface electrode pair 114a, 114b. The thoracic impedance measurement module 212 obtains, via the electrode/sensor connection switching circuitry 224, a thoracic impedance signal by measuring the potential difference between two of the surface electrodes 114a-114d. In some examples, the high frequency, low amplitude current applied between the surface electrodes 114a-114d has a frequency between about 50 kilohertz (kHz) and about 100 kHz and has an amplitude between about 1 milliamps root mean squared (mArms) and 4 mArms. In other examples, the current has a frequency below about 50 kHz or above about 100 kHz. In some examples, the current has a frequency of between about 20 kHz and about 200 kHz, or between about 20 kHz and about 1 megahertz (MHz).

In some implementations, the thoracic impedance measurement module 212 uses measurements obtained from two pairs of surface electrodes. In one implementation, four electrodes are used for impedance measurements. The four electrodes include two force electrodes and two sense electrodes, with each force electrode paired with a sense electrode. Each group of four electrodes can resolve a vector in space to localize observed changes. There are two of the four electrodes on each side of a vector. In particular, there may be a force electrode and a sense electrode on each side of a vector. The force electrode applies (or injects) current into the body (or receives current injected into the body). The sense electrode measures the disturbance caused by the current applied into the body by the force electrode. In various implementations, the sense electrodes of the vector sense current and/or voltage drop caused by the injection of a current into the body by the force electrodes through application of a voltage and/or current. Since voltage and current are related to impedance $(V=Z*i)$, to measure impedance Z, a known current i can be applied, and the subsequent voltage drop V can be measured, and Z can be calculated using the known current i and measured change in voltage V. According to various implementations, the properties of the circuitry for applying current (the force electrode) are different from the properties of the circuitry for measuring the voltage (the sense electrodes). According to various implementations, there are two different sets of electrodes (force electrodes and sense electrodes), and each electrode has a positive and a negative side.

Using the four electrodes, different parts of the tissue and tissue at varying depths can be scanned by adjusting the frequency of the injected waveform. Impedance is measured on a single vector without spatial resolution. In some implementations, more than four electrodes are used, and additional electrode pairs add multiple vectors, which add additional tissue scans. In some implementations, each pair of sense and force electrodes is one side of multiple vectors. For example, two pairs of sense and force electrodes form one vector, and three pairs of sense and force electrodes form three vectors. In other examples, more pairs of electrodes are used, and more vectors are formed. As such, each vector monitors a selected spatial area.

In other embodiments, each of the electrodes 114a-114d may operate as either a force electrode or a sense electrode depending on the electrode/sensor connection switching circuitry 224. Further, the force electrodes may be configured by the electrode/sensor connection switching circuitry 224 to control either a voltage or a current applied by the force electrodes and the sense electrodes may measure either a current or a voltage, respectively. Based on the voltage or the current applied and the measured current or voltage, the system 102 may derive an impedance, which may be utilized for determining certain health characteristics of the subject.

The measurement of impedance can be used to determine physiologic information, including respiration rate, tidal volume, and lung fluids. Impedance measurements can also be used to determine derived metrics such as pulmonary resistance and lung fluid location. For respiration rate, the respiration of a patient causes air to go into the lungs and increase the lung volume which compresses the surrounding tissue. This leads to changes in the impedance with an increase on some vectors (mainly vectors that cross the lung(s)) and a decrease in other vectors due to redirection of the current. Respiration rate is determined based on the changes in impedance, which follow the same periodicity as the respiration. Additionally, tidal volume can be monitored by determining the amplitude of the changes, which are proportional to the tidal volume (change in lung volume). The shape of the waveform relates to the breathing pattern and can be used to monitor the airway/lung resistance.

Fluid in the lungs can be detected and/or monitored by scanning multiple frequencies and/or multiple spatial vectors, which are used to distinguish fluids in the lung versus other bodily fluids. Another method to add to the specificity of the separation between lung fluid and other bodily fluids is to measure impedance changes with posture. Changes in posture can cause lung fluids to move with gravity. The movement in fluids can be detected by various vector measurements and helps separate the moving lung fluids from other bodily fluids. In one example, the vector of impedance is measured at the bottom of the lungs using a single frequency of 50 kHz. For example, the impedance vector between electrodes 114c and 114d of FIG. 1 may be measured. If the impedance vector is measured when the person is supine (horizontal position) and then is measured again after the patient moves to the standard Fowler position, a change in the impedance of 1 ohm or more can indicate the presence of fluid in the lungs. In congestive heart failure patients, the change in impedance is typically more than 5 ohms when patients start experiencing symptoms.

Note that in medicine, Fowler's position is a standard patient position in which the patient is seated in a semi-upright sitting position with the patient's torso at an angle relative to the horizontal plane. In various examples, Fowler's position includes the patient's torso being at an angle of between about 15 and thirty degrees, the patient's torso being at an angle of between about 30 and about 45 degrees, the patient's torso being at an angle of between about 45 and about 60 degrees, and the patient's torso being an angle of between about 60 and about 90 degrees. In standard Fowler's position, the patient's torso is between about 45 and about 60 degrees.

In various implementations, the device includes a sensor that can determine the position of the device, thereby indicating the horizontal position of the patient, including whether the patient is upright or supine. The device automatically measures thoracic impedance in both upright and supine positions of the patient, and uses these two measurements to monitor and/or detect chronic conditions.

As discussed above, the device also includes an electrocardiogram (ECG) measurement module 214, which can perform ECG measurements at some or all of the plurality of surface electrodes 114a-114d that contact the skin of the human subject 104 on his or her torso, upper chest, and/or neck areas. In one embodiment, the pulse oximetry measurement module 222 (or the finger-pocket device for performing finger-based pulse oximetry measurements) can be employed in conjunction with the ECG measurement module 214 to obtain further measurements. Because respiratory activity can cause corresponding changes in the measured thoracic impedance, each of the breath rate measurement module 216 and the tidal volume measurement module 218 can operate in conjunction with the thoracic impedance measurement module 212 to obtain measurements of the human subject's breath rate/breath rate variability and tidal volume, respectively.

The heart sounds-based measurement module 220 can include an electronic stethoscope, stethophone, or any other suitable device for obtaining heart rate variability data, as well as obtaining and converting heart sounds (e.g., the S1 heart sound, "lub"; the S2 heart sound, "dub") to sensing data that can be subsequently algorithmically analyzed by the data analyzer 226 to obtain information pertaining to the S3 heart sound (also known as the proto-diastolic or ventricular gallop), which may be heard at the beginning of diastole (during the rapid filling of the ventricles), and the S4 heart sound (also known as the atrial gallop), which may heard late in diastole. In one implementation, the heart sounds-based measurement module 220 measures sub-audible heart sounds (heart sounds below about 40 Hz), thereby measuring S3 and S4 heart sounds that cannot be heard by a physician or other health care professional using a stethoscope. S3 and S4 heart sounds are pathological and indicate heart failure. Information about sub-audible S3 and S4 heart sounds can be used to detect and monitor chronic conditions. The heart sounds can be measured by a sensor placed over the heart region. The sensor detects sounds and/or vibrations. The sensor detects different heart sounds depending on the location of sensor placement relative to the various regions of the heart. For example, to maximize the chances of detecting the signal that is pertinent to S3, the sensor may be positioned over the apex of the heart, which is in the fifth intercostal space. Abnormal S3 heart sounds occur when the heart pumping is compromised. The S3 heart sounds are early indicators of heart problems and can change prior to other measurable heart signals. Because the S3 heart sounds have a lot of energy at low frequencies that are not audible to the human ear, the S3 heart sounds are initially undetectable by physicians. A sensing system sensitive to low frequencies coupled with an automated algorithm can detect the S3 heart sounds earlier. Any presence of S3 or S4 heart sounds in adult patients is abnormal and the detection of any energy that is determined to be S3 or S4 can be used to flag a potential problem. The flags from different sensors can be combined by higher-level logic to generate a single metric that can be designed to be more specific and more sensitive than individual measures.

In one embodiment, the pulse oximetry measurement module 222 (or the finger-pocket device for performing finger-based pulse oximetry measurements) can be employed in conjunction with the heart sounds-based measurement module 220 to obtain further measurements. It is noted that the pulse oximetry measurement module 222 can perform reflective or finger-based pulse oximetry measurements. In one embodiment, the pulse oximetry measurement module 222 can include a pulse rate sensor, as well as a blood oxygen level (SpO2) sensor.

Having performed the thoracic impedance measurements, the ECG measurements, the breath rate and tidal volume measurements, the heart rate variability/heart sounds-based measurements, and the pulse oximetry measurements, the thoracic impedance measurement module 212, the electrocardiogram (ECG) measurement module 214, the breath rate and tidal volume measurement modules 216, 218, the heart sounds-based measurement module 220, and the pulse oximetry measurement module 222 provide corresponding multi-modality sensing data to the data analyzer 226 for at least partial data analysis, data trending, and/or data reduction. In one embodiment, such multi-modality sensing data can also be analyzed, trended, and/or reduced "in the cloud" and made available in cloud-based data storage 110 with pre-set alerts for use in various levels of clinical interventions. For example, the data analyzer 226 can (1) analyze the thoracic impedance measurement data to obtain information pertaining to the human subject's lung congestion, (2) analyze the breath rate and tidal volume measurement data to obtain information pertaining to the human subject's shortness of breath (e.g., dyspnea, paroxysmal nocturnal dyspnea), (3) analyze the ECG measurement data and heart rate variability data in multiple (e.g., 3) projections to obtain information pertaining to possible atrial fibrillation and localization in the human subject 104, and (4) analyze the heart sounds-based measurement data to obtain information pertaining to a possible increase in the S3 heart sound (which can be indicative of a failing left ventricle due to a dilated CHF condition).

The data analyzer 226 provides the at least partially analyzed multi-modality sensing data to the data fusion/decision engine 228, which effectively at least partially fuses or combines the multi-modality sensing data, in accordance with one or more algorithms and/or decision criteria, for subsequent use in making one or more inferences about the chronic condition status of the human subject 104. For example, combined multi-modality sensing data that show, substantially concurrently, an increase in the S3 heart sound, an increase in rapid shallow breathing while the human subject 104 is at rest, a decrease in the relative tidal volume, and a decrease in the thoracic impedance, can be a strong predictor of a potentially problematic chronic condition in the human subject 104. In one embodiment, such algorithms and/or decision criteria implemented in the data fusion/decision engine 228 can be proven and/or refined through one or more clinical trials for strengthening the inferences made by the data fusion/decision engine 228 regarding the human subject's chronic condition status. The processor 202 then provides the at least partially combined multi-modality sensing data to the transmitter/receiver 204, which transmits the combined multi-modality sensing data either directly over the wireless communication paths 122 to the cloud 110, or over the wireless communication paths 116 to the smartphone 106. Next, the smartphone 106 can transmit, via the communications network 108, the combined multi-modality sensing data over the wireless communication paths 118, 120 to the cloud 110, where it can be further analyzed, trended, reduced, and/or fused. The resulting curated multi-modality sensing data can then be remotely downloaded by hospital clinicians for monitoring and/or tracking purposes.

Figure 3:
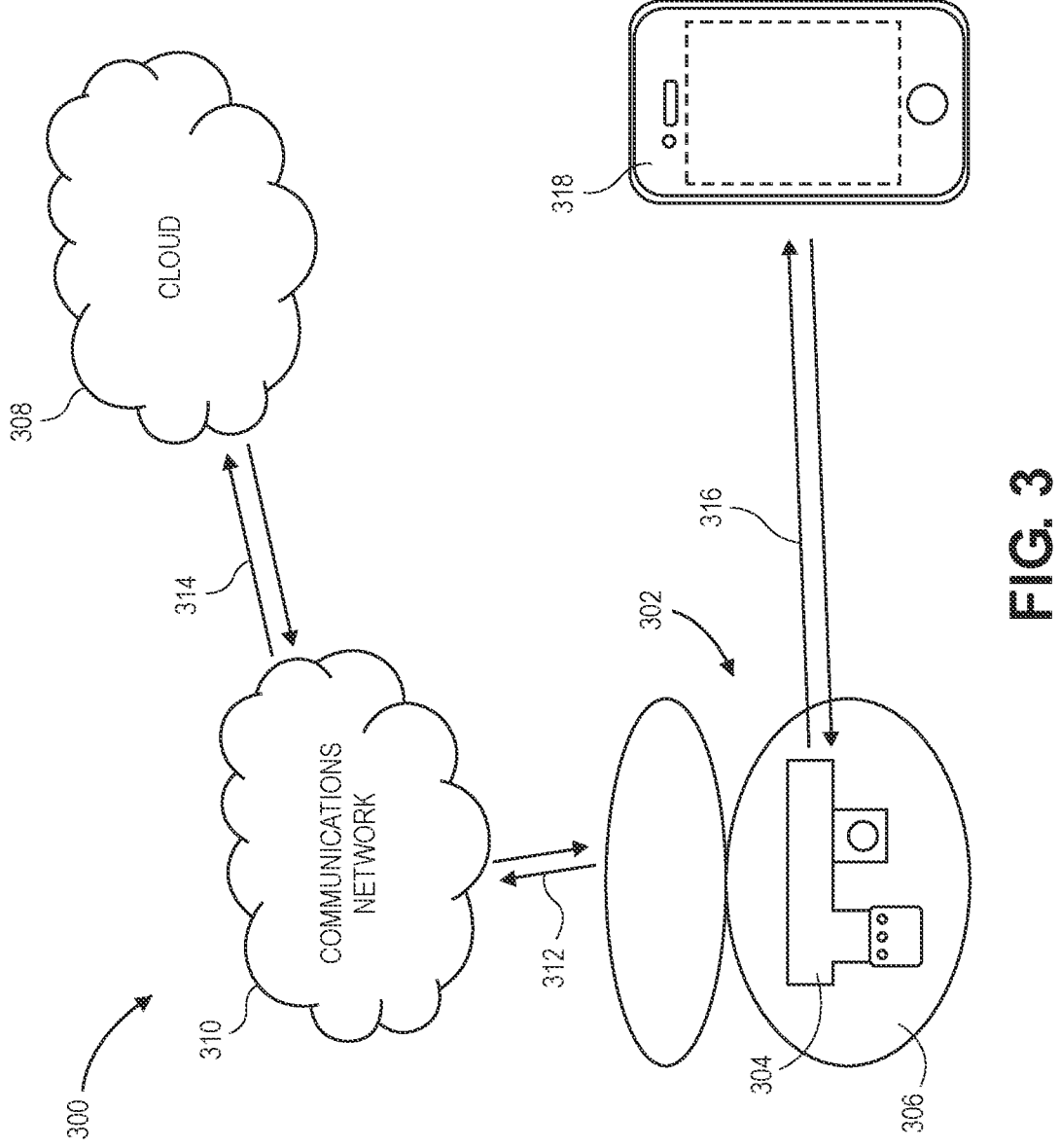
FIG. 3 illustrates another example environment in which an illustrative embodiment of an example system for non-invasively detecting and monitoring medical or health conditions may be employed, according to some embodiments of the disclosure.

FIG. 3 illustrates another example environment 300 in which an illustrative embodiment of an example system 302 for non-invasively detecting and monitoring medical or health conditions may be employed, according to some embodiments of the disclosure. In particular, the system 302 in the illustrated embodiment includes a device 304 for non-invasively detecting medical or health condition of a subject and a case 306 for storage of the device 304. The case 306 may be referred to as a base station.

The device 304 may be incapable of wireless communication in some embodiments. In these embodiments, the device 304 may depend on a wired connection with the case 306 to communicate with remote devices. For example, the device 304 may establish a wired connection with the case 306 when the device 304 is positioned in the case 306, and the device 304 and the case 306 may exchange communications via the wired connection. The case 306 may be enabled to wirelessly communicate with the remote devices, and may act as an intermediary for communication between the remote devices and the device 304. Further details of the device 304 and the case 306 are described in relation to FIGS. 7-11.

The environment 300 further includes a cloud 308. The cloud 308 may include one or more of the features of the cloud 110 (FIG. 1). The cloud 308 may include one or more servers that provides resources for remote devices, including the system 302. For example, the resources may include computing resources (such as processors), storage resources (such as memory devices), or some combination thereof, that may be utilized by the remote devices. The resources may include resources for cloud computing, data processing, data analysis, data trending, data reduction, data fusion, data storage, and/or other functions. Further, the cloud 308 can be utilized to share data among remote devices. For example, data stored on the cloud 308 may be shared with a medical provider of the subject, thereby allowing the medical provider to monitor health characteristics of the subject captured by the device 304. In some embodiments, the medical provider may utilize the data to perform electrical imaging tomography (EIT) and/or impedance spectroscopy for evaluating the health characteristics of the subject.

The environment 300 further includes a communications network 310. The communications network 310 may provide a communication intermediary between the system 302 and the cloud 308. For example, the communications network 310 may comprise one or more communication components that facilitate and/or manage the transfer of communications between the cloud 308 and the system 302. In some embodiments, the communications network 310 may further be coupled to remote devices, and may facilitate and/or manage transfer of communications among the system 302, the cloud 308, and the remote devices.

The communications network 310 may provide wireless connections between the system 302 and the cloud 308, may provide wired connections between the system 302 and the cloud 308, or some combination thereof. In particular, a communication path 312 may be established between the system 302 and the communications network 310, the communication path 312 providing for transfer of communications between the system 302 and the communications network 310. Another communication path 314 may be established between the communications network 310 and the cloud 308, the communication path 314 providing for transfer of communications between the communications network 310 and the cloud 308. The communication path 312 and the communication path 314 may both be wireless communication paths, may both be wired communication paths, or one may be a wireless communication path and the other may be a wired communication path. For example, the communications network 310 may comprise a cellular network in some embodiments, and the communication path 312 may be a wireless, cellular communication path in some embodiments. In other embodiments, the communications network 310 may comprise a local area network and the case 306 may be connected via a wired connection (such as an ethernet connection) to the communications network 310.

In other embodiments where the device 304 is capable of wireless communication, the device 304 may operate as described in relation to the environment 100 (FIG. 1) and in relation to the environment 300. In particular, the device 304 may operate via wireless connections as described in relation to the environment 100 when the device 304 is disconnected from the case 306. When the device 304 is connected with the case 306, the device 304 may operate with the case 306 as an intermediary as described in relation to the environment 300. Further, the device 304 may determine whether to operate in accordance with the operation described in relation to the environment 100 or the environment 300 based on a state of the device 304. For example, the device 304 may determine that it is in a low power state based on a battery level of the device 304 and select to disable wireless communications of the device 304 to save power, thereby being limited to the operation described in relation to the environment 300.

In some embodiments, the environment 300 may further include a remote device 318. The remote device 318 may include a display for displaying information to a user and/or a user input element (such as a keyboard, a touch screen, one or more buttons, and/or other inputs) to receive input from the user. In some embodiments, the remote device 318 may comprise a smartphone, such as the smartphone 106 (FIG. 1).

A communication path 316 may be established between the device 304 and the remote device 318. The communication path 316 may comprise a wireless communication path, such as communication via Bluetooth communication, WiFi communication, or any other suitable short-range communication. The device 304 and the remote device 318 may exchange communications via the communication path 316. For example, the device 304 may provide information to the remote device 318 to be displayed to the user on the remote device 318. The information provided via the device 304 may comprise results of operations requested by the remote device 318 and/or indications of actions to be taken for performing an operation (such as proper placement of the device 304 on a subject). The remote device 318 may receive inputs from a user, and utilize the inputs to change what is displayed on the remote device 318 and/or provide the inputs to the device 304 to cause the device 304 to perform operations in response to the inputs. In some embodiments, user authentication can be utilized for establishment of the communication path 316 or utilization of the communication path 316 for communication. For example, user authentication may comprise password verification, biometric recognition, and/or device recognition. Failure of user authentication may cause the communication path 316 to not be established and/or data to be prevented from transmission across the communication path 316.

Figure 4A:
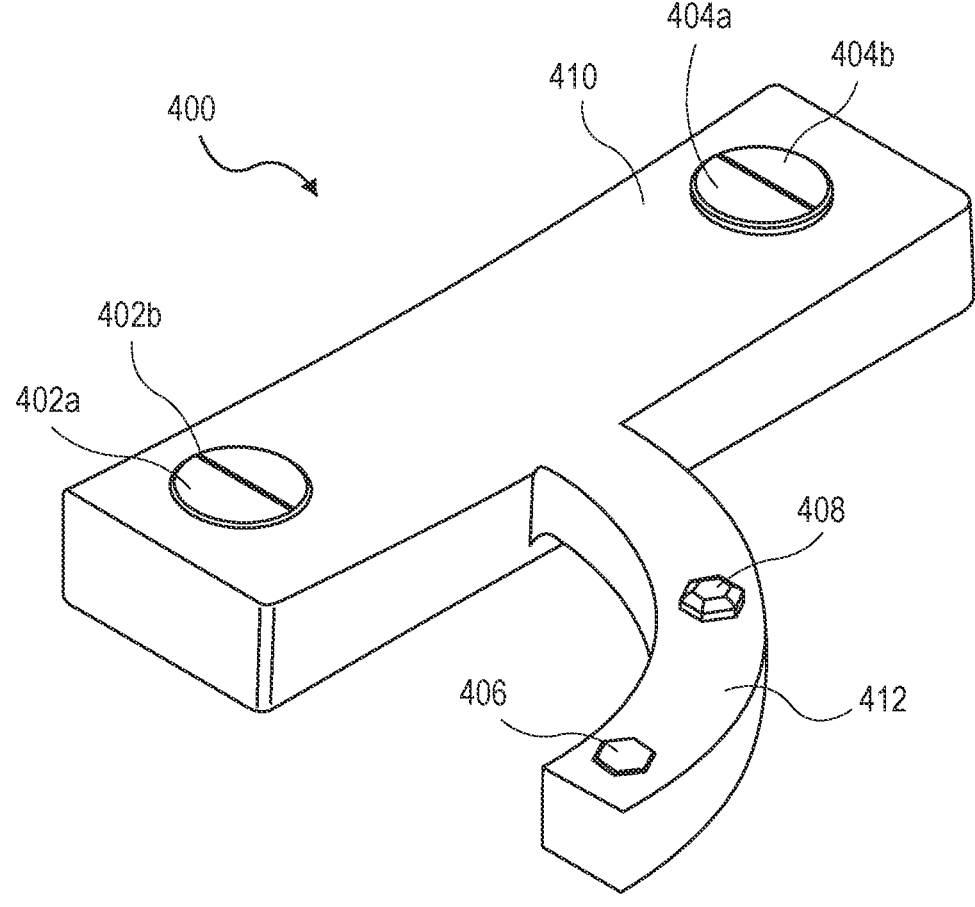
FIGS. 4A-4C are diagrams illustrating a device for detecting and monitoring health conditions of a subject, according to some embodiments of the disclosure.

FIG. 4A is a diagram illustrating a device 400 for detecting and monitoring health conditions of a subject, according to some embodiments of the disclosure. In particular, the device 400 non-invasively detects and monitors chronic conditions in human subjects. The device 400 includes a first electrode pair 402a-402b, a second electrode pair 404a-404b, a third electrode 406, and a fourth electrode 408. The first electrode pair 402a-402b includes one force electrode and one sense electrode, as described above. Similarly, the second electrode pair 404a-404b includes one force electrode and one sense electrode. The third 406 and fourth 408 electrode can be any type of electrode, including, for example, one of a heart sound sensor, a force electrode, and a sense electrode. The device 400 has an elongated rectangular base portion 410, which includes the first electrode pair 402a-402b positioned on a first end and the second electrode pair 404a-404b positioned on a second end. In various examples, the elongated base portion 410 is between about 10 centimeters (cm) and about 20 cm long, and between about 2 cm and about 6 cm wide. In some examples, the elongated base portion 410 is between about 1 cm and about 4 cm thick. Along the mid-section of the length of the rectangular base portion 410, a curved tail portion 412 extends out in the same plane as the rectangular base portion 410 and arcs around toward the direction of the first electrode pair 402a-402b. The base portion 410 and the curved tail portion 412 may comprise a frame of the device 400. The curved tail portion 412 includes the third electrode 406 and the fourth electrode 408. The third electrode 406 is positioned at the end of the curved tail portion 412 and the fourth electrode 408 is positioned in the middle of the curved tail portion 412. According to various implementations, the device 400 is placed on a subject's torso, with the electrodes 402a-402b, 404a-404b, 406, 408 in contact with the subject's skin.

Figure 4C:
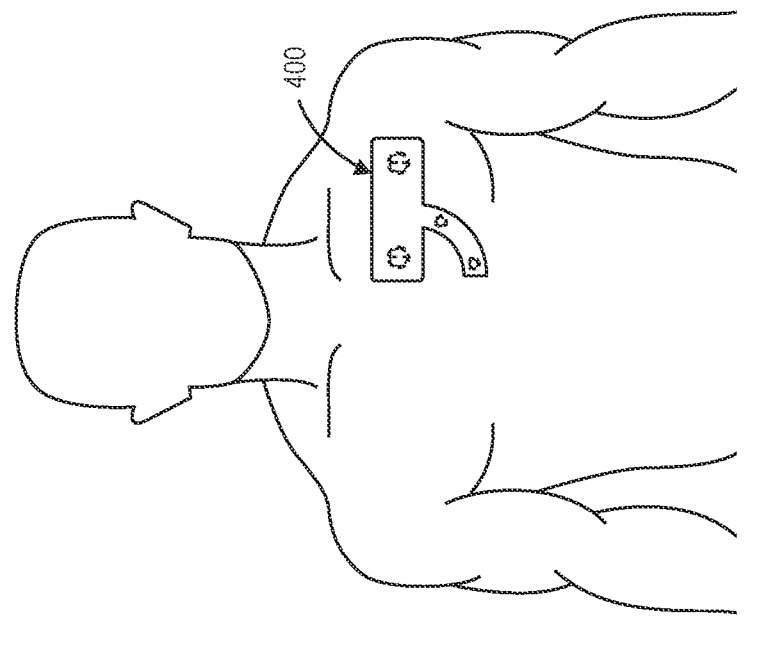
Figure 4B:
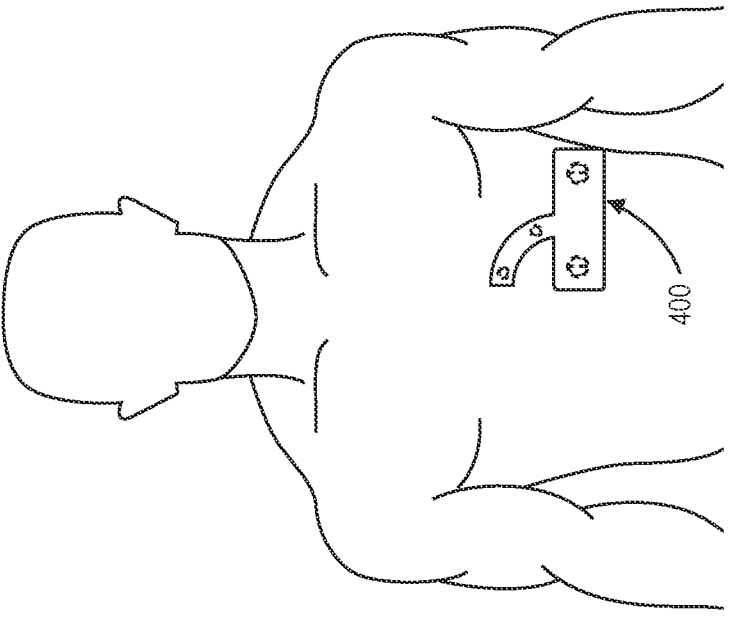

FIG. 4B shows the device 400 positioned on the torso of a subject. The elongated base portion 410 is positioned around the sixth intercostal space, and the curved tail portion 412 extends upwards, curving inward toward the midline of the torso. In some implementations, the fourth electrode 408 is positioned in the fifth intercostal space on the left side of the torso, and is optimally positioned to detect S3 sounds. In other implementations, the curved tail portion 412 curves outward away from the midline of the torso. The electrodes are shown in dotted lines to indicate that the electrodes are located on an opposite side of the device 400 from shown with the electrodes positioned against the skin of the subject.

FIG. 4C shows the device 400 positioned on the torso of a subject. The elongated base portion 410 is positioned below the shoulder level, and the curved tail portion 412 extends downwards over the heart, curving inward toward the midline of the torso. In other implementations, the curved tail portion 412 curves outward away from the midline of the torso. The electrodes are shown in dotted lines to indicate that the electrodes are located on an opposite side of the device 400 from shown with the electrodes positioned against the skin of the subject.

Figure 5:
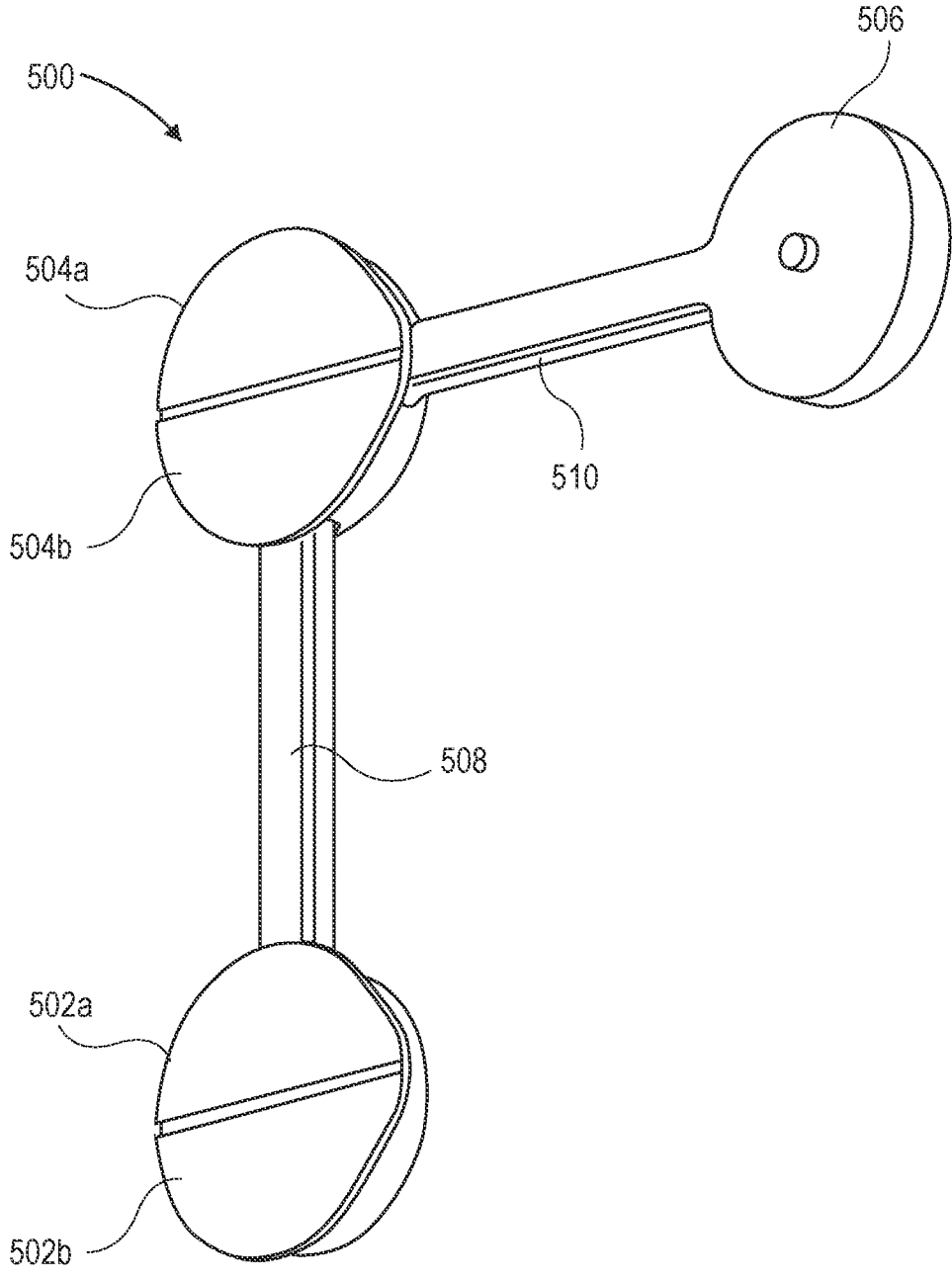
FIG. 5 is a diagram illustrating another device for detecting and monitoring health conditions of a subject, according to some embodiments of the disclosure.

FIG. 5 is a diagram illustrating a device 500 for detecting and monitoring health conditions of a subject, according to some embodiments of the disclosure. In particular, the device 500 non-invasively detects and monitors chronic conditions in human subjects. The device 500 includes a first electrode pair 502a-502b, a second electrode pair 504a-504b, and a sensor 506. The first electrode pair 502a-502b includes a force electrode and a sense electrode. Similarly, the second electrode pair 504a-504b includes a force electrode and a sense electrode. Additionally, one of the first electrode pair 502a-502b and one of the second electrode pair 504a-504b measures ECG. The sensor 506 is a heart sounds sensor for detecting sound vibrations. In one implementation, the sensor 506 is a piezo-electric microphone.

The membrane of the microphone protrudes to contact the torso and detect the heart sounds. The first electrode pair 502a-502b is connected to the second electrode pair 504a-504b via a first elongated element 508. The second electrode pair 504a-504b is connected to the sensor 506 via a second elongated element 510. The first elongated element 508 and the second elongated element 510 may comprise a frame of the device 500. As shown in FIG. 5, in the device 500, the first 508 and second 510 elongated elements are approximately perpendicular to each other. In other implementations, the first 508 and second 510 elongated elements can be oriented at any selected position relative to each other. The device 500 is placed on a subject's torso, with the electrodes 502a-502b and 504a-504b, and the sensor 506 in contact with the subject's skin. In some implementations, the electrodes 502a-502b and 504a-504b, are positioned along the sixth intercostal space and the sensor 506 is positioned along the fifth intercostal space at the apex of the heart.

Figure 6:
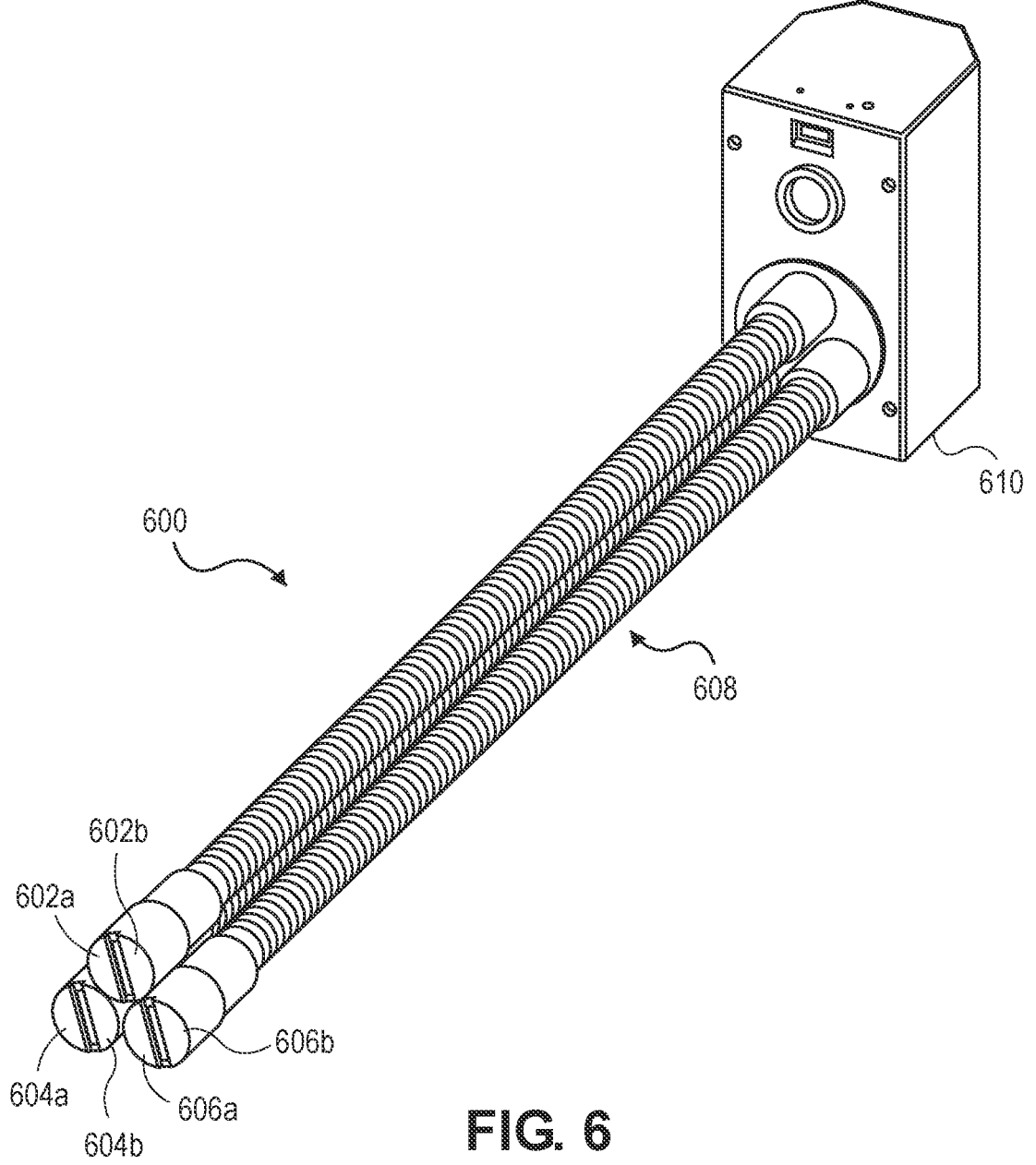
FIG. 6 is a diagram illustrating another device for detecting and monitoring health conditions of a subject, according to some embodiments of the disclosure.

FIG. 6 is a diagram illustrating a device 600 for detecting and monitoring health conditions of a subject, according to some embodiments of the disclosure. The device 600 includes three long flexible arms 608 that extend from a rectangular box 610. The rectangular box 610 and the flexible arms 608 may comprise a frame of the device 600. At the tip of each of the flexible arms 608 is a pair of electrodes—first electrode pair 602a-602b, second electrode pair 604a-604b, and third electrode pair 606a-606b. The electrode pairs 602a-602b, 604a-604b, 606a-606b can be moved to be oriented to fit a subject's body and secured in place. The device 600 is a handheld device that the subject places on the body. In some examples, the subject positions the device 600 on the body regularly, such as two or more times per day, and records measurements. According to some implementations, the device 600 includes a sensor for recording heart sounds. The heart sound sensor may also be attached to the device via a long flexible arm. The heart sound sensor may be a microphone, and, in some examples, it is a piezo-electric microphone.

In other implementations, electrodes and/or other sensors are positioned subcutaneously on a subject. Subcutaneous sensors can remain in place long term and can be connected to an external device for measurements. In other implementations, electrodes and/or other sensors are positioned within patches which attach to a subject's skin. The patches are connected to an external device for measurement.

Figure 7:
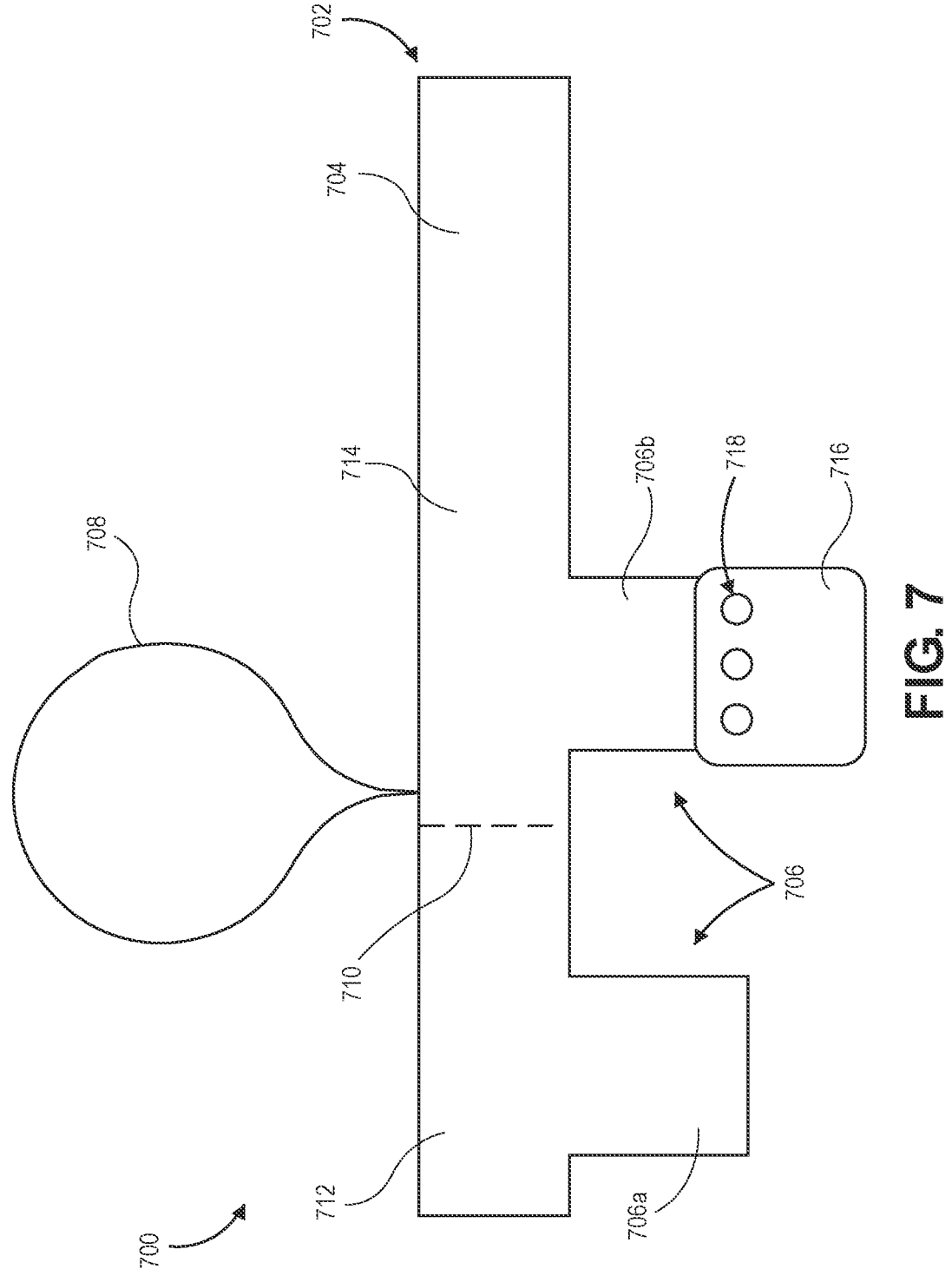
FIG. 7 illustrates another example device for detecting and monitoring health conditions of a subject, according to some embodiments of the disclosure.

FIG. 7 illustrates another example device 700 for detecting and monitoring health conditions of a subject, according to some embodiments of the disclosure. In particular, FIG. 7 illustrates a front side of the device 700 that is to be positioned away from the skin of a subject when worn by the subject.

The device 700 may include a frame 702. Components of the device 700 may be mounted to the frame 702 to maintain positions of the components relative to each other. In some embodiments, the frame 702 may be available in different sizes, where the different sizes have different distances between the components or arrangements of the components to facilitate different body types and/or body sizes of a subject. In other embodiments, mounting locations of the components to the frame 702 may be adjustable to adjust the locations of the components for different body types and/or body sizes of a subject. In some of the embodiments where the mounting locations are adjustable, ability to adjust the locations of the components may be limited to specific individuals (such as by requiring a special tool for adjustment that may not be made publicly available), which may prevent a subject from inadvertently adjusting the mounting locations to incorrect locations for operation.

The frame 702 may include a main body 704 that extends in a first direction. Further, the frame 702 may include one or more extensions 706 that extend from the main body 704 in one or more other directions. For example, the frame 702 includes a first extension 706a and a second extension 706b that extend from the main body 704 in the illustrated embodiment. The first extension 706a and the second extension 706b extend substantially (within 5 degrees) perpendicularly from the main body 704 in the illustrated embodiment, however it is to be understood that the angles may be different in other embodiments. Further, the extensions 706 are illustrated as being affixed to the main body 704 in the illustrated embodiment. In other embodiments, the positions of the extensions 706 along the main body 704 may be adjustable.

In some embodiments, the main body 704 may include rigid portions and one or more bend points between the rigid portions. For example, the main body 704 includes a bend point 710 (indicated by a dashed line), a first rigid portion 712 located on a first side of the bend point 710, and a second rigid portion 714 on a second side of the bend point 710 in the illustrated embodiment. The first rigid portion 712 and the second rigid portion 714 may each include a rigid material (such as a rigid metal, rigid plastic, or other rigid material) that maintains a rigidity of the rigid portions. In some embodiments, the rigid material may be surrounded by other material (such as fabric) that may be more comfortable against a skin of the subject. The bend point 710 may include a flexible material that allows the first rigid portion 712 and the second rigid portion 714 to bend about the bend point 710. In some embodiments, the flexible material may be the same material (such as fabric) that surrounds the rigid material and the bend point 710 may be characterized by the absence of the rigid material. In other embodiments, the bend point 710 may include a hinge rather than the flexible material. Further, an entirety of the main body 704 may be flexible or rigid in other embodiments. The extensions 706 may be rigid or flexible, and may be formed of the same material as some portion of the main body 704 or may be formed of a different material.

The device 700 may further include a reference element 708, which may also be referred to as a guide. The reference element 708 may be connected to the frame 702 and may be utilized for proper positioning of the device 700 on a subject. In particular, the reference element 708 may identify a reference point on the subject and may facilitate proper positioning of the frame 702 relative to the subject. The reference element 708 comprises a lanyard or a necklace (collectively referred to as "lanyard" herein) in the illustrated embodiment. The lanyard may utilize a neck of the subject as a reference point for positioning of the frame 702. In particular, placing the lanyard around the neck of the subject may help the subject in positioning the frame 702 a proper distance from the neck of the subject for proper positioning of the frame 702. In some of the embodiments, the lanyard may be adjustable or may be available in different sizes to facilitate proper positioning for different body types and/or different body sizes. In other embodiments, the reference element 708 may comprise other means for facilitating positioning the frame 702, such as straps or other markers that reference a point on the subject (such one or both of the arms of the subject, or a sternum of the subject) and indicate a position that the frame 702 should be positioned relative to the point on the subject. The proper positioning of the frame 702 may comprise one or more of the positionings of the surface sensors described throughout this disclosure.

The device 700 may further include a control module 716. The control module 716 may be mounted to the frame 702. The control module 716 is mounted to the second extension 706b in the illustrated embodiment, however it is to be understood that the control module 716 may be mounted to other locations of the frame 702 in other embodiments.

The control module 716 may include one or more of the multi-modality sensing and measurement modules 112 (FIG. 2), the processor 202 (FIG. 2), the transmitter/receiver 204 (FIG. 2), the data storage 206 (FIG. 2), the memory 208 (FIG. 2), or some combination thereof. The control module 716 may further include a battery for powering the device 700. The control module 716 may be coupled to one or more surface sensors of the device 700, as described further in relation to FIG. 8. The control module 716 may control operation of the surface sensors and may store data received from the surface sensors. In some embodiments, the control module 716 may store the data, along with an indication of a time that the data was captured (such as time stamping the data), for future transfer of the data to a cloud (such as the cloud 110 (FIG. 1) and/or the cloud 308 (FIG. 3)). In other embodiments, the control module 716 may further perform operations with the data prior to transfer of the data to the cloud. For example, the control module 716 may analyze, trend, reduce and/or fuse the data, or some portion thereof, prior to transfer of the data to the cloud.

In some embodiments, the control module 716 may further include an orientation detection sensor. The orientation detection sensor may determine an orientation of the control module 716, which may be utilized for determining an orientation of the subject. For example, the control module 716 can determine whether a subject is standing, laying, or can determine an angle at which the subject is reclined based on the orientation measured by the orientation detection sensor. In some embodiments, the orientation detection sensor may comprise an accelerometer that can be utilized for determining the orientation of the control module 716.

The control module 716 may further include one or more indicators 718. The indicators 718 may indicate a status of the device 700. For example, the indicators 718 may indicate a status of electronics of the device 700, an orientation of the subject (or instructions for the subject to transition to a proper orientation for performance of an operation by the device 700), data transmission status, power status, operational status, or some combination thereof. The indicators 718 may include visual indicators, audible indicators, motion indicators (such as an indicator that produces a physical force including vibration), or some combination thereof. In the illustrated embodiment, the indicators 718 comprise lights that may light up to indicate the status of the device 700. In other embodiments, the indicators 718 may include lights, displays, speakers, or some combination thereof.

In some embodiments, the indicators 718 may include three different colored lights (such as light emitting diodes (LEDs)). Depending on the color of the light that is lit, whether the light is blinking, and/or whether the light is pulsating, different states of the device 700 may be indicated. For example, a first light may indicate that the device 700 is connected to a communications network when lit, the device is ready to connect to the communications network when blinking, and/or is exchanging data with the communications network when pulsating. A second light may indicate that the device 700 is in a pre-reading mode when lit, and/or is measuring an ECG of the subject when blinking. A third light may indicate that the device 700 is fully charged when lit, is charging when pulsating, and/or is in a low battery state when blinking. Further, if all three lights are blinking at the same time, it may indicate that one or more of the electrodes or sensors are not properly applied to the subject. If all three of the lights are blinking in turn, it may indicate that the position of the subject is improper for capturing data. Further, the order in which the three lights are blinking in turn may indicate how the position of the subject is incorrect, such as indicating that the subject should be leaned forward or backward from a current position.

While a shape of the frame 702 and positioning of components mounted to the frame 702 are described in relation to FIG. 7, it is to be understood that the shape of the frame 702 and/or positioning of the components may be different in other embodiments. In particular, the shape of the frame 702 and positioning of the components may be any shape or position that achieves the positioning of the surface sensors in accordance with one or more of the surface sensors positioning described throughout this disclosure, such as the positioning described in relation to FIGS. 26A-26G.

Figure 8:
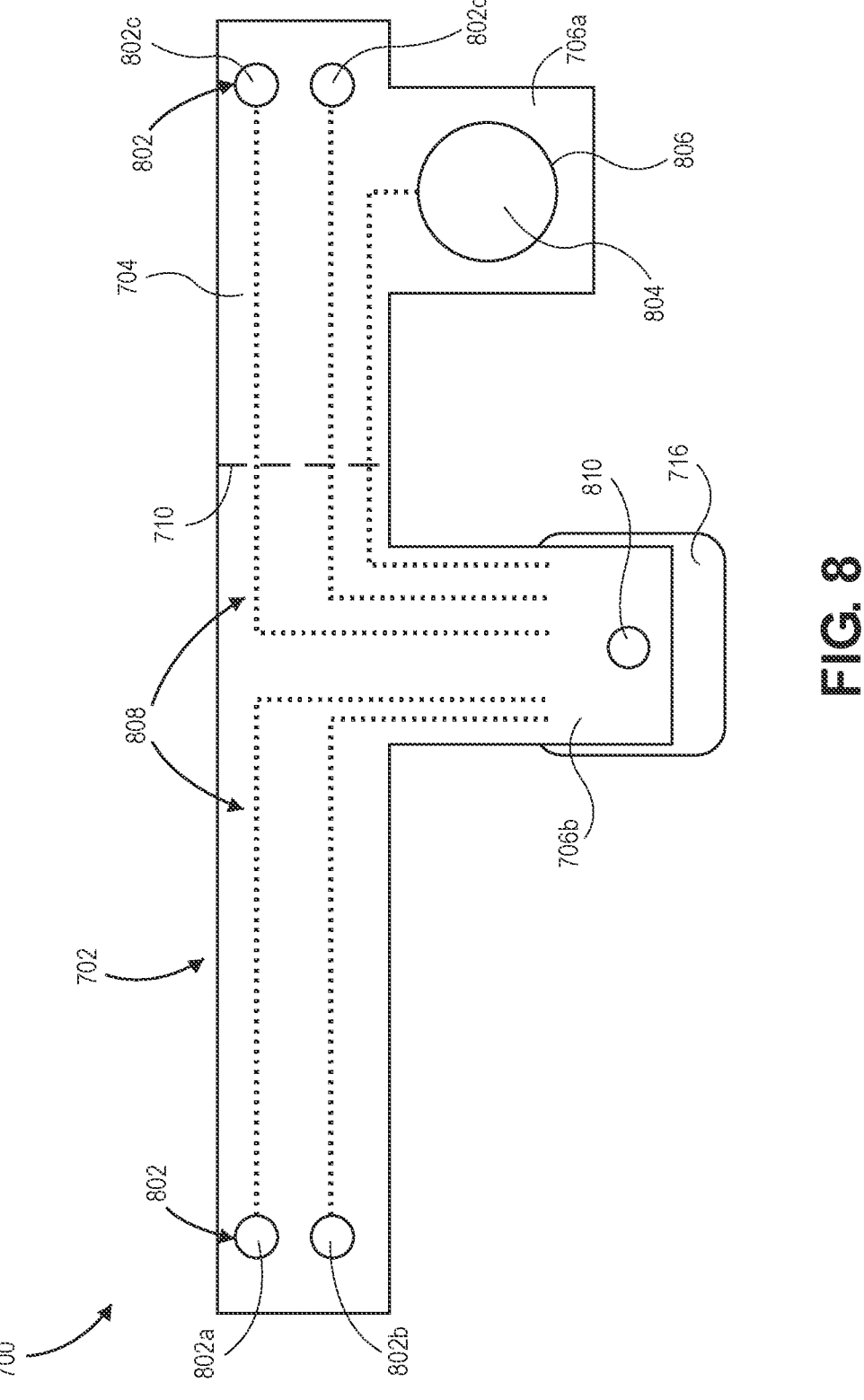
FIG. 8 illustrates a back side of the example device of FIG. 7, according to some embodiments of the disclosure.

FIG. 8 illustrates a back side of the example device 700 of FIG. 7, according to some embodiments of the disclosure. In particular, FIG. 8 illustrates a side of the device 700 that is to be positioned toward the skin of a subject when worn by the subject.

The device 700 includes one or more surface sensors mounted to frame 702. The surface sensors may include one or more of the features of the surface sensors described throughout this disclosure. The surface sensors may include electrodes, heart sound sensors, ultrasound sensors, photoplethysmography (PPG) sensors, or some combination thereof. The surface sensors may be arranged to contact a surface of a skin of a subject when the device 700 is worn by the subject.

The surface sensors may include one or more electrodes 802. For example, the device 700 includes four electrodes in the illustrated embodiment. The electrodes 802 may include polished stainless-steel electrodes, platinum black electrodes, or some combination thereof. A plurality of the electrodes 802 may be positioned in locations to measure a thoracic impedance when the device 700 is worn by the subject. For example, the plurality of electrodes 802 may be positioned against a chest of the subject, a neck of the subject, a stomach of the subject, or some combination thereof, when the device 700 is worn by the subject. In some embodiments, the electrodes 802 may be positioned in the locations indicated by FIGS. 26A-26G. In the illustrated embodiment, the device 700 includes a first electrode 802a and a second electrode 802b located toward a first end of the main body 704, and a third electrode 802c and a fourth electrode 802d located toward a second end of the main body 704. In other embodiments, the device 700 may have more or fewer electrodes 802, the electrodes 802 may be located in different positions, or some combination thereof.

The electrodes 802 located toward a same end of the main body 704 may be located as close as possible in view of manufacturing and design considerations (such as allowing for space for proper adhesion of the electrodes 802 by adhesives, such as first adhesive 902 (FIG. 9), second adhesive 904 (FIG. 9), and third adhesive 906 (FIG. 9)). For example, the distance between the electrodes located toward the same end may be separated by 0.5 cm in some embodiments. In particular, the first electrode 802a may be separated from the second electrode 802b by 0.5 cm, and the third electrode 802c may be separated from the fourth electrode 802d by 0.5 cm in some embodiments. In some embodiments, the distance between the electrodes located toward the same end may be separated by between 0.3 cm and 5 cm.

The electrodes 802 located at opposite ends of the main body 704 may be located at a distance to span a lung of a subject. For example, the first electrode 802a and the second electrode 802b may be separated from the third electrode 802c and the fourth electrode 802d by between 17 cm and 20 cm in some embodiments, where between 17 cm and 20 cm may be approximately the width of an adult human lung. In some embodiments, the first electrode 802a and the second electrode 802b may be separated from the third electrode 802c and the fourth electrode 802d by 19 cm. In other embodiments, the distance by which the first electrode 802a and the second electrode 802b are separated from the third electrode 802c and the fourth electrode 802d may be adjustable to fit different sized subjects.

While the electrodes 802 are illustrated as being circular in the embodiment, it is to be understood that the electrodes 802 may be any shape, including oval-shaped, rectangle-shaped, triangle-shaped, diamond-shaped, or some combination thereof. Further, the electrodes 802 may comprise segmented electrodes in some embodiments, where each of the electrodes 802 may be formed of multiple pieces of material. For example, the electrodes 802 illustrated may be segmented into halves or quarters. Further, the size of the electrodes 802 (or segments thereof) may be any size suitable for performance of the measurements, such as having a combined diameter of between 0.5 cm and 5 cm.

The surface sensor may further include one or more sound sensors. The sound sensors may include piezo-electric sensors, acoustic sensors, or some combination thereof. In the illustrated embodiment, the device 700 includes a sound sensor 804. The sound sensor 804 is located on the first extension 706a. In other embodiments, the sound sensor 804 may be located at other positions along the frame 702. The sound sensor 804 may be positioned against a chest of the subject and adjacent to a heart of the subject when the device 700 is worn by the subject. The sound sensor 804 may detect sounds of the heart of the subject during operation. The sound sensor 804 may have a curved surface that is to be positioned against the skin of the subject, where the curve may provide greater surface contact with the skin of the subject and provide good contact with the skin. Further, an edge 806 of the sound sensor 804 may be protruded and the skin of the subject may deform to fill the cavity formed by the protrusion. The protrusion of the edge 806 may assist in blocking external sounds from affecting the capture of the sounds of the heart captured by the sound sensor 804. In some embodiments, gel may be applied a surface of the sound sensor 804 that is to contact the skin of the subject, where the gel may reduce inadvertent movement of the sound sensor 804, reduce loss of sound transmission that may be caused by air located between the sound sensor 804 and the skin of the subject, or some combination thereof.

In some embodiments, the edge 806 of the sound sensor 804 may form an O-ring. The portion of the sound sensor 804 inside of the edge 806 may be recessed as compared to the edge 806. The recess formed within the edge 806 may be filled with gel in some embodiments. The gel may facilitate transmission of heart sounds to the portion of the sound sensor 804 inside of the edge 806. The gel may be implemented as part of the sound sensor 804 (such as a solid-gel)

or may be applied and/or reapplied to the sound sensor 804 prior to the application of the device 700 to a subject.

The device 700 may further include one or more temperature sensors. For example, the device 700 includes a temperature sensor 810. The temperature sensor 810 may contact the skin of the subject and may measure the temperature of the skin of the subject. In other embodiments, the temperature sensor 810 may be located near the electrodes 802 or may be embedded in area of one or more of the pads of the electrodes 802. Further, the device 700 may include an additional temperature sensor that is to measure a temperature of the environment in which the subject is located in other embodiments.

In other embodiments, the device 700 may further include additional types of sensors, including any of the types of sensors described throughout this disclosure. For example, the device 700 may include a pulse oximetry sensor in some embodiments. The pulse oximetry sensor may be located near the electrodes 802, near the sound sensor 804, near the temperature sensor 810, or at any other position along the frame 702.

The surface sensors may be coupled to the control module 716 and operation of the surface sensors may be controlled by the control module 716. In particular, the surface sensors may be coupled to the control module 716 by electrical conductors 808 (illustrated by dotted lines). The electrical conductors 808 may comprise wires, circuits, or some combination thereof. The electrical conductors 808, or some portion thereof, may be flexible. In particular, at least a portion of the electrical conductors 808 that extend across the bend point 710 may be flexible and may be designed to be bent multiple times without becoming inoperable. The electrical conductors 808 may be located within the frame 702, along the frame 702, or some combination thereof. In embodiments where the bend point 710 comprises a hinge, the electrical conductors 808 may include portions of the hinge that are designed to be electrically conductive.

The control module 716 may control operation of the surface sensors and receive data of the surface senses via the electrical conductors 808. For example, the control module 716 may define when sound data is to be captured by the sound sensor 804, and may receive and store the sound data from the sound sensor 804. Further, the control module 716 may determine which portion of the electrodes 802 are to apply electrical force (such as voltage and/or current) and which portion of the electrodes 802 are to detect the changes (such as increase/decrease in voltage drop or current flow) affected by the application of the electrical force. For example, the control module 716 may cause the first electrode 802a and the second electrode 802b to apply the electrical force, while the control module 716 causes the third electrode 802c, and the fourth electrode 802d to detect the changes. A first vector may be formed between the first electrode 802a, that applies the electrical potential, and the third electrode 802c, that detects the changes. A second vector may be formed between the second electrode 802b, that applies the electrical potential, and the fourth electrode 802d, that detects the changes. The second vector may be lower on the body of the subject than the first vector when the device 700 is positioned on the subject. In some embodiments, the changes detected by one of the electrodes 802, such as the fourth electrode 802d, may be used as reference data and may be utilized for compensation of data captured by the other electrodes. In other embodiments, the device 700 may include a particular electrode that may be utilized as a reference electrode and capture reference data.

In some embodiments, the control module 716 may cause one or more of the electrodes 802 to apply alternating currents as the electrical force, and may cause one more of the electrodes 802 to detect the changes caused by the application of the alternating currents. For example, the control module 716 may cause the first electrode 802a and the second electrode 802b to apply alternating currents, while the control module 716 may cause the third electrode 802c and the fourth electrode 802d to detect the changes. The control module 716 may determine equi-potentials based on the detected changes, where the equi-potentials determined from the third electrode 802c and the fourth electrode 802d may be utilized to perform EIT. Further, the control module 716 may vary the frequency of the alternating current in some embodiments. In these embodiments, the changes detected may include an amount of capacitance and/or resistance between the electrodes applying the alternating currents and the electrodes detecting the changes, in addition to the equi-potentials. The amount of capacitance and/or resistance may be used for impedance spectroscopy to produce an impedance spectrum representation for the paths between the electrodes applying the alternating currents and the electrodes detecting the changes. Further, the equi-potentials may also be utilized to perform EIT when the frequency of the alternating current is varied.

Figure 9:
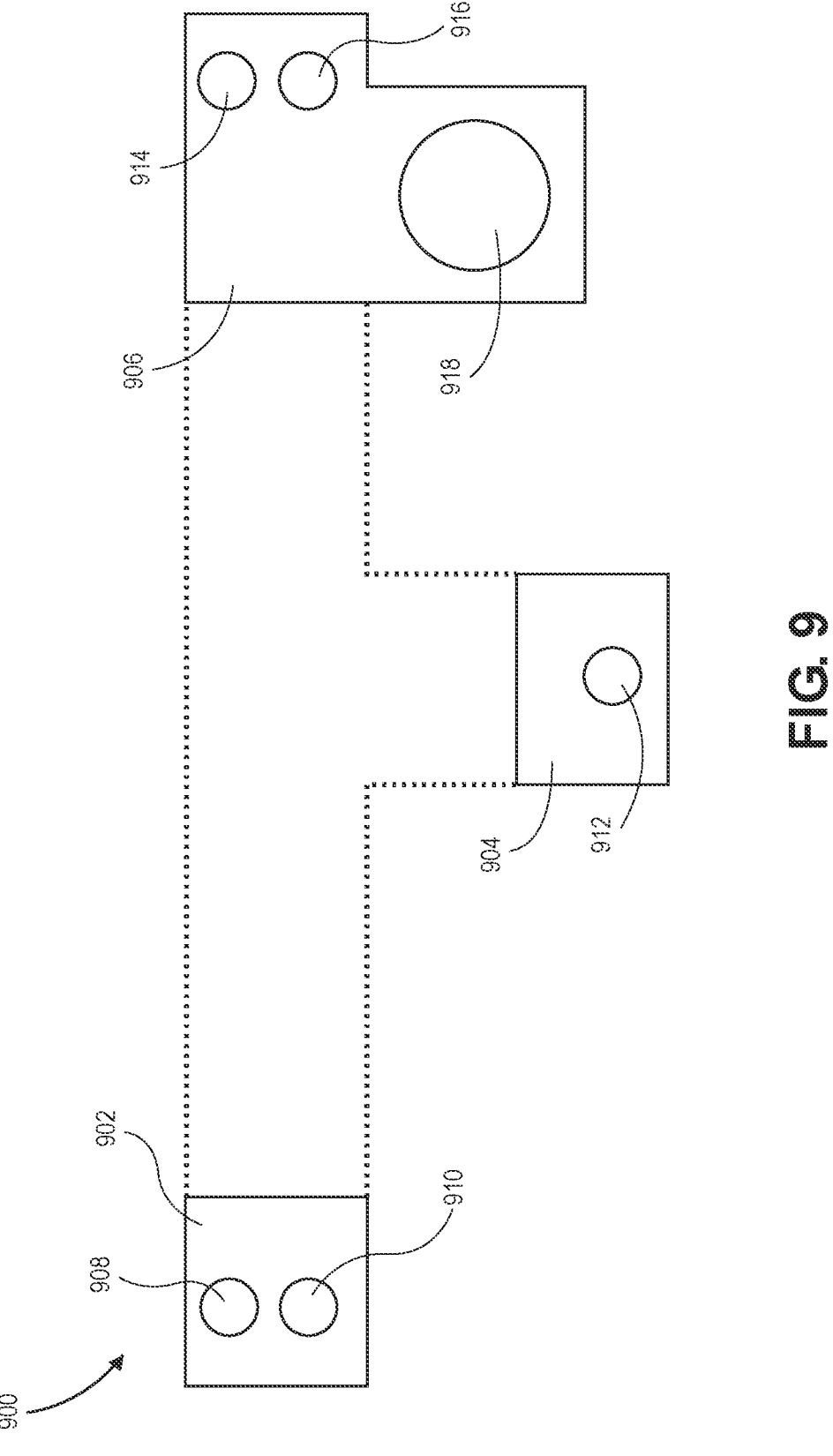
FIG. 9 illustrates example adhesives to be utilized for maintaining a device for detecting and monitoring medical or health conditions on a subject, according to some embodiments of the disclosure.

FIG. 9 illustrates example adhesives 900 to be utilized for maintaining a device for detecting and monitoring medical or health conditions on a subject, according to some embodiments of the disclosure. In particular, the illustrated embodiment illustrates adhesives 900 for the device 700 (FIG. 7). For clarity, an outline of the device 700 that is not covered by the adhesives 900 is shown in dotted lines to illustrate the relationship between the device 700 and the intended locations of the adhesives 900.

In the illustrated embodiment, the adhesives 900 include a first adhesive 902, a second adhesive 904, and a third adhesive 906. The adhesives 900 may be double-sided adhesives, where one side of the adhesives 900 is to adhere to the device 700 and the other side of the adhesives 900 is to adhere to the skin of a subject when the device 700 is worn by the subject. The adhesives 900 may be disposable, consumable, and/or replaceable in some embodiments. In other embodiments, the adhesives 900 may be reusable.

The adhesives 900 are to be positioned near the surface sensors of the device 700 and are to maintain contact of the surface sensors with the skin of the subject when the device 700 is worn by the subject. For example, the first adhesive 902 is to be located near the first electrode 802a (FIG. 8) and the second electrode 802b (FIG. 8), the second adhesive 904 is to be located near the temperature sensor 810 (FIG. 8), and the third adhesive 906 is to be located near the third electrode 802c (FIG. 8), the fourth electrode 802d (FIG. 8), and the sound sensor 804 (FIG. 8). Further, the adhesives 900 are to encircle the surface sensors in the illustrated embodiment. In particular, the first adhesive 902 may include a first aperture 908 through which the first electrode 802a is to extend to contact the skin of the subject and a second aperture 910 through which the second electrode 802b is to extend to contact the skin of the subject. The second adhesive 904 may include an aperture 912 through which the temperature sensor 810 is to extend to contact the skin of the subject. The third adhesive 906 may include a first aperture 914 through which the third electrode 802c is to extend to contact the skin of the subject, a second aperture 916 through which the fourth electrode 802d is to extend to contact the skin of the subject, and a third aperture 918 through which the sound sensor 804 is to extend to contact the skin of the subject. Each of the apertures may have a diameter slightly larger than the element that is to extend through the aperture, thereby facilitating simple placement of the elements through the apertures. In other embodiments, the adhesives 900 may include more or fewer adhesives than in the illustrated embodiment.

Figure 10:
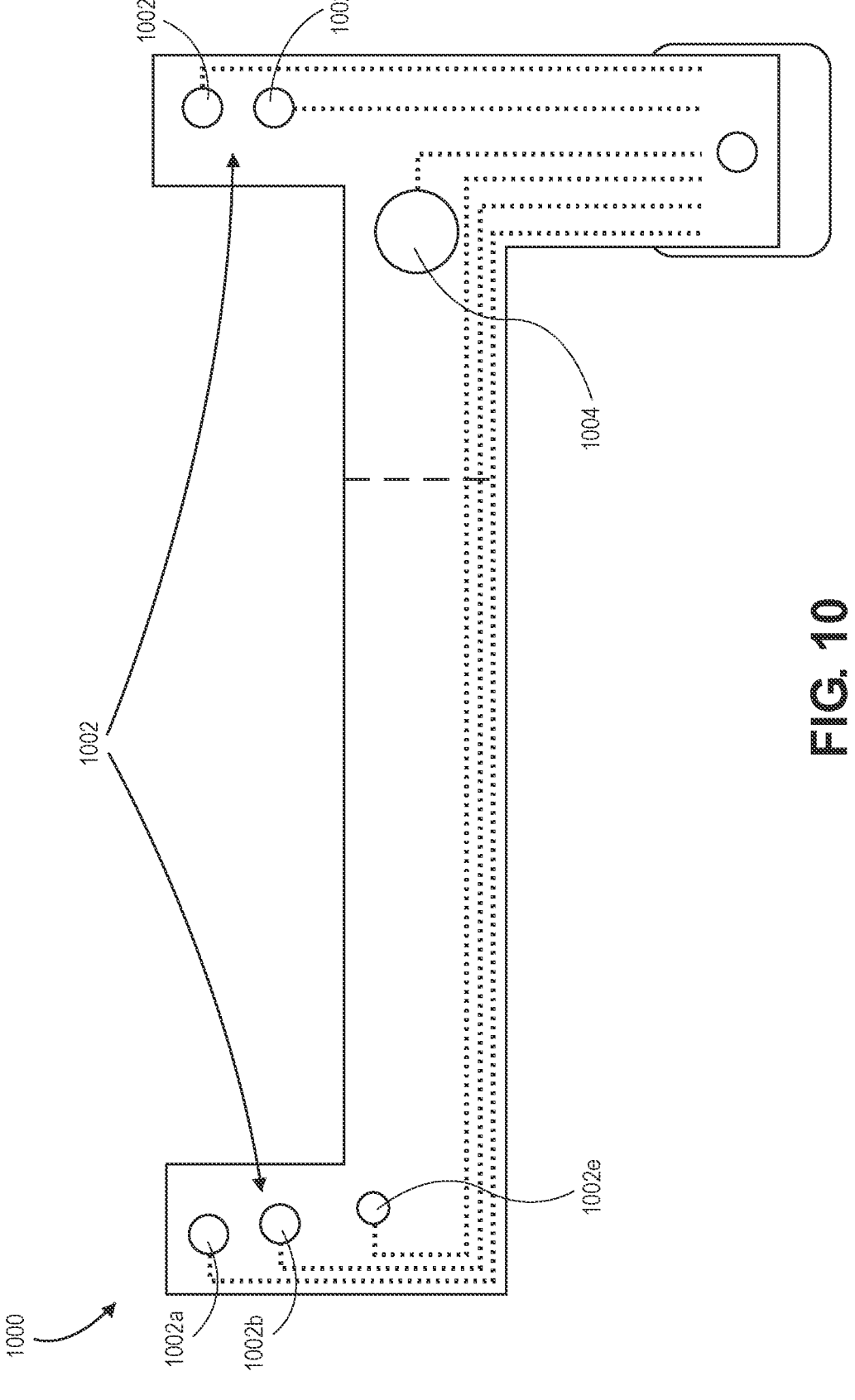
FIG. 10 illustrates another example device for detecting and monitoring health conditions of a subject, according to some embodiments of the disclosure.

FIG. 10 illustrates another example device 1000 for detecting and monitoring health conditions of a subject, according to some embodiments of the disclosure. In particular, FIG. 10 illustrates a side of the device 1000 that is to be positioned toward the skin of a subject when worn by the subject. The device 1000 may include one or more of the features of the device 700 (FIG. 7).

The device 1000 may include one or more electrodes 1002. For example, the device 1000 includes five electrodes 1002 in the illustrated embodiment. In particular, the device 1000 includes a first electrode 1002a, a second electrode 1002b, a third electrode 1002c, and a fourth electrode 1002d. Each of the first electrode 1002a, the second electrode 1002b, the third electrode 1002c, and the fourth electrode 1002d may include one or more of the features of the first electrode 802a (FIG. 8), the second electrode 802b (FIG. 8), the third electrode 802c (FIG. 8), and the fourth electrode 802d (FIG. 8), respectively.

Further, the device 1000 may include a reference electrode 1002e (which may be referred to as a leg drive electrode). The reference electrode 1002e may be utilized to set a body of the subject at a certain potential, which may minimize noise detected by the other electrodes 1002. In some embodiments, the reference electrode 1002e may be utilized to detect a potential of the body of the subject, which may be utilized when processing data captured by the other electrodes 1002 to compensate for any noise.

The reference electrode 1002e may be smaller than the other of the electrodes 1002 in some embodiments. For example, the reference electrode 1002e may have a diameter of 1 cm or less, and the first electrode 1002a, the second electrode 1002b, the third electrode 1002c, and the fourth electrode 1002d may have a diameter of 2 cm or more. In other embodiments, the reference electrode 1002e may be the same size as the other electrodes 1002. Further, the distance between the reference electrode 1002e and the other electrodes 1002 may be 0.5 cm or greater. For example, the reference electrode 1002e may be located 0.5 cm or greater from the second electrode 1002b in the illustrated embodiment.

The device 1000 may further include a sound sensor 1004. The sound sensor 1004 may include one or more of the features of the sound sensor 804 (FIG. 8). The sound sensor 1004 may be configured to be located near a heart of the subject and may be utilized for detecting sounds produced by the heart of the subject. Accordingly, the sound sensor 1004 may be located below the first electrode 1002a, the second electrode 1002b, the third electrode 1002c, and the fourth electrode 1002d, and between the electrodes 1002. In particular, the sound sensor 1004 may be located below the fourth electrode 1002d by between 2 cm and 10 cm, and to a side of the fourth electrode 1002d by between 2 cm and 10 cm in the illustrated embodiment. In some embodiments, the sound sensor 1004 may be configured to be positioned between a midline of the subject and 10 cm toward a side from the midline of the subject. In other embodiments, the position of the sound sensor 1004, may be limited by space or manufacturability. The sound sensor 1004 may be located at different positions relative the electrodes 1002 in other embodiments while still being configured to be located near the heart of the subject.

Figure 25:
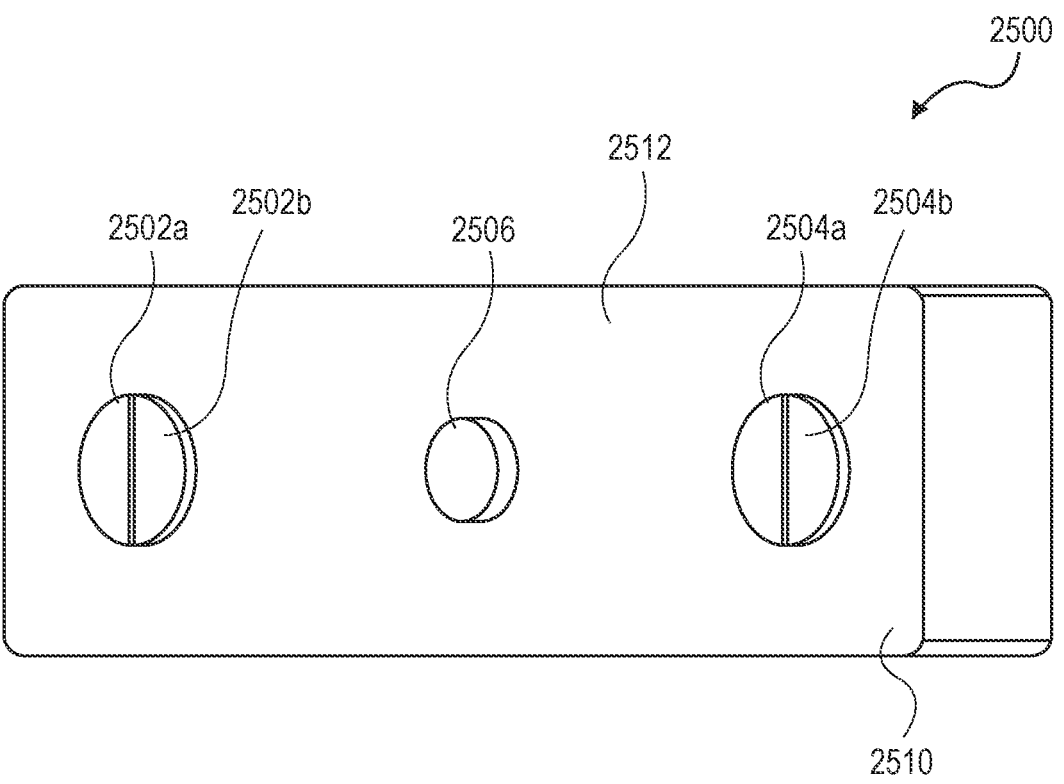
FIG. 25 is a diagram illustrating another device for detecting and monitoring health conditions of a subject, according to some embodiments of the disclosure.

FIG. 11 illustrates an example system 1100 utilized for non-invasively detecting and monitoring medical or health conditions, according to some embodiments of the disclosure. The system 1100 may be implemented as the system 302 (FIG. 3) in the environment 300 (FIG. 3). In particular, the system 1100 may include a device 1102 and a case 1104. The case 1104 may be referred to as a base station. In the illustrated environment, the device 1102 is shown as the device 700 (FIG. 7). In other embodiments, the device 1102 may comprise any of the devices described herein, including the device 400 (FIG. 4A), the device 500 (FIG. 5), the device 600 (FIG. 6), the device 700, the device 1000 (FIG. 10), or the device 2500 (FIG. 25). The device 1102 and the case 1104 may include one or more of the features of the device 304 (FIG. 3) and the case 306 (FIG. 3), respectively.

The case 1104 may receive the device 1102 and may be utilized for storage of the device 1102. In the illustrated embodiment, the case 1104 may include a contoured portion 1106 into which the device 1102 can be received. The contoured portion 1106 may be a similar shape as the device 1102, or the device 1102 when the device 1102 is in a folded state (as shown). In other embodiments, the contoured portion 1106 may be omitted or may be shaped to receive a portion of the device 1102.

In the illustrated embodiment, the case 1104 is shown with a bottom piece 1108 and a top piece 1110 connected by a hinge 1112. The hinge 1112 may allow the bottom piece 1108 and the top piece 1110 to rotate to open and close the case 1104. For example, the case 1104 may be closed with the device 1102 located within the contoured portion 1106 of the case 1104 to protect the device 1102 from damage when not in use. It is to be understood that the case 1104 described and illustrated is just one example of case that may be implemented within the system 1100. In other embodiments, the case 1104 may comprise a single piece to which the device 1102 may be docked. In some embodiments, the case 1104 may be sized to fit on a night stand.

The case 1104 may include electronics for transmission and storage of data from the device 1102. For example, the case 1104 may include electronics for transmission and storage of data received from the device 1102. For example, the case 1104 may include a transmitter/receiver (such as the transceiver/receiver 204), a data storage (such as the data storage 206), a memory device (such as the memory 208), or some combination thereof. In particular, the transmitter/receiver may be utilized for transmitting communications between the device 1102 and the case 1104, transmitting communications between the case 1104 and a communications network (such as the communications network 310 (FIG. 3)), or some combination thereof. The transmitter/receiver may provide for wired communication, wireless communication, or some combination thereof. For example, the transmitter/receiver may provide Bluetooth communication, WiFi communication, other suitable short-range communication, cellular communication, or other suitable long-range communications, or some combination thereof. In some embodiments, the transmitter/receiver may provide for wired communication with the device 1102, and may provide for wired communication or wireless communication with the communications network.

The case 1104 may include electronics for processing of data and/or communications. For example, the case 1104 may include a processor (such as the processor 202 (FIG. 2)). The processor may perform one or more of the operations of the data analyzer 226 (FIG. 2) and/or the data fusion/decision engine 228 (FIG. 2). For example, the processor may analyze, trend, reduce and/or fuse data received from the device 1102, or some portion thereof. In other embodiments, the device 1102 may perform one or more of the operations of the data analyzer 226 and/or the data fusion/decision engine 228, both the device 1102 and the case 1104 may perform one or more of the operations of the data analyzer 226 and/or the data fusion/decision engine 228, the device 1102 may perform some of the operations of the data analyzer 226 and/or the data fusion/decision engine 228, or neither of the device 1102 and the case 1104 may perform the operations of the data analyzer 226 and/or the data fusion/decision engine 228. In some embodiments, the processor and/or the device 1102 may perform compression of the data in addition to, or in lieu of, the operations of the data analyzer 226 and/or the data fusion/decision engine 228. Further, the device 1102, the case 1104, or both, may process and/or format the data to be in a format that can be readily utilized for EIT and/or impedance spectroscopy. In embodiments where the operations are performed, the operations may be performed with the data received from the device 1102 prior to the data being transferred to the communications network.

The case 1104 may further include electronics for charging the device 1102. For example, the case 1104 may connect to a power source (such as mains electricity) and may include a charging circuitry that enables charging of the device 1102 from the power source when the device 1102 is connected to the case 1104.

The case 1104 may further include a connector for connecting with the device 1102. For example, the case 1104 includes pins 1114 in the illustrated embodiment. The pins 1114 are coupled with the electronics of the case 1104 and may couple the device 1102 with the electronics of the case 1104 when the device 1102 is connected to the case 1104. When the device 1102 is connected to the case 1104, the pins 1114 may facilitate the transfer of data between the device 1102 and the case 1104, and the charging of the device 1102. The pins 1114 may extend into the contoured portion 1106, such that the device 1102 can be connected to the pins 1114 when the device 1102 is positioned within the contoured portion 1106 of the case 1104. In other embodiments, the connector may comprise a header (such as a USB port and/or a serial port), a cable (such as a USB cable or another computer cable), or some combination thereof.

The device 1102 is illustrated as showing a bottom of the device 1102 with the device 1102 in a folded state. For example, a portion of the device 1102 may be folded around a bend point (such as the bend point 710 (FIG. 7)) for placement of the device 1102 within the case 1104. The device 1102 may further include a control module 1116, which may include one or more of the features of the control module 716 (FIG. 7). The control module 1116 may include a connector to mate with the connector of the case 1104. For example, the control module 1116 includes receptacles 1118 that are to mate with the pins 1114 of the case 1104. The device 1102 is connected to the case 1104 when the connector of the control module 1116 is mated with the connector of the case 1104. When the device 1102 is connected with the case 1104, the case 1104 may charge the device 1102 and communications (such as data) may be exchanged between the device 1102 and the case 1104. Once the case 1104 receives the data from the device 1102, the data may be communicated to the communications network by the case 1104.

Figure 12:
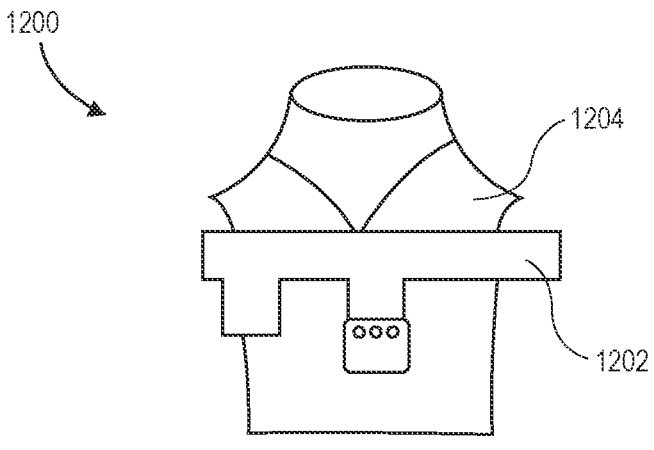
FIG. 12 illustrates another example system utilized for non-invasively detecting and monitoring medical or health conditions, according to some embodiments of the disclosure.

FIG. 12 illustrates another example system 1200 utilized for non-invasively detecting and monitoring medical or health conditions, according to some embodiments of the disclosure. The system 1200 may include one or more of the features of the system 1100 (FIG. 11).

The system 1200 may include a device 1202. In the illustrated environment, the device 1202 is shown as the device 700 (FIG. 7). In other embodiments, the device 1202 may comprise any of the devices described herein, including the device 400 (FIG. 4A), the device 500 (FIG. 5), the device 600 (FIG. 6), the device 700, the device 1000 (FIG. 10), or the device 2500 (FIG. 25).

The system 1200 may further include a base station 1204. The base station 1204 may include one or more of the features of the case 1104 (FIG. 11). In particular, the base station 1204 may be utilized for storage, charging, and/or transfer of data with the device 1202. For example, the device 1202 may be hung from the base station 1204 by a reference element of the device (such as the reference element 708 (FIG. 7)) for storage. In the particular embodiment, the reference element may be a lanyard or a necklace that extends around a portion of the base station 1204 and suspends the device 1202 from the base station 1204. The base station 1204 may further include one or more wires to couple to the device 1202 for charging and/or transfer of data with the device 1202, may include wireless circuitry for wirelessly charging and/or transfer of data with the device 1202, or some combination thereof.

Figure 13:
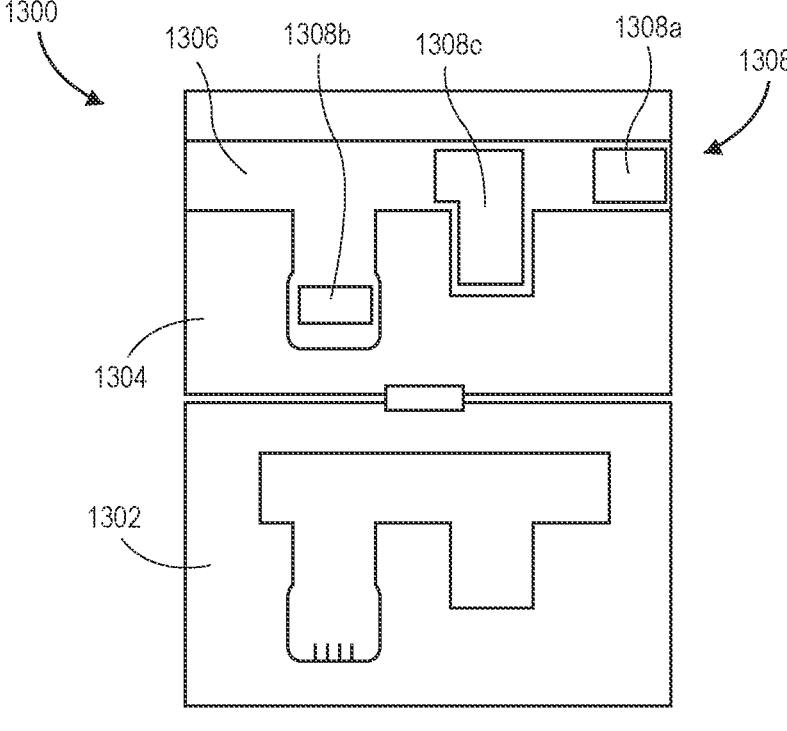
FIG. 13 illustrates another example base station, according to some embodiments of the disclosure.

FIG. 13 illustrates another example base station 1300, according to some embodiments of the disclosure. The base station 1300 may include one or more of the features of the case 1104 (FIG. 11). The base station 1300 may comprise a case with a lower portion 1302 and an upper portion 1304. The lower portion 1302 may be similar to the bottom piece 1108 (FIG. 11) of the case 1104, and may be utilized for storage, charging, and transfer of data with a device.

The upper portion 1304 may be utilized for refreshing and/or replacement of adhesives (such as the first adhesive 902 (FIG. 9), the second adhesive 904 (FIG. 9), and the third adhesive 906 (FIG. 9)) for the device. In particular, the upper portion 1304 may include a tray that has a recess 1306 to receive the device and one or more adhesive recesses 1308 to receive the adhesives.

The adhesive recesses 1308 may extend from the recess 1306 into the upper portion 1304. The adhesive recesses 1308 may receive the adhesives and the adhesives may be adhered to the device in proper locations when the device is placed within the recess 1306. In particular, a user may place the adhesives in the adhesive recesses 1308 with protective covers covering the adhesive portions and then remove the protective covers facing away from the upper portion 1304 exposing the adhesive portions. When the device is placed in the recess 1306, the exposed adhesive portions may contact the device and adhere the adhesive to the device in the proper locations.

In some embodiments, different adhesives may be adhered at different times. For example, the device may be wider than the base station 1300 when the device is unfolded in the illustrated embodiment. To facilitate proper placement of the adhesive a first portion of the adhesives may be applied at one time and a second portion of the adhesives may be applied at a different time. In the illustrated embodiment, the first adhesive 902 may be placed in a first adhesive recess 1308a and the second adhesive 904 may be placed in a second adhesive recess 1308b. A portion of the device may then be placed in the recess 1306 with the control module 716 located adjacent to the second adhesive recess 1308b, and the first electrode 802a and the second electrode 802b located adjacent to the first adhesive recess 1308a. When the portion of the device is placed in the recess 1306, the first adhesive 902 and the second adhesive 904 may become adhered to the device. Separately, the third adhesive 906 may be placed in a third adhesive recess 1308c. Another portion of the device may be placed in the recess 1306 with the third electrode 802c, the fourth electrode 802d, and the sound sensor 804 located adjacent to the third adhesive recess 1308c. When the portion of the device is placed in the recess 1306, the third adhesive 906 may become adhered to the device.

Figure 14:
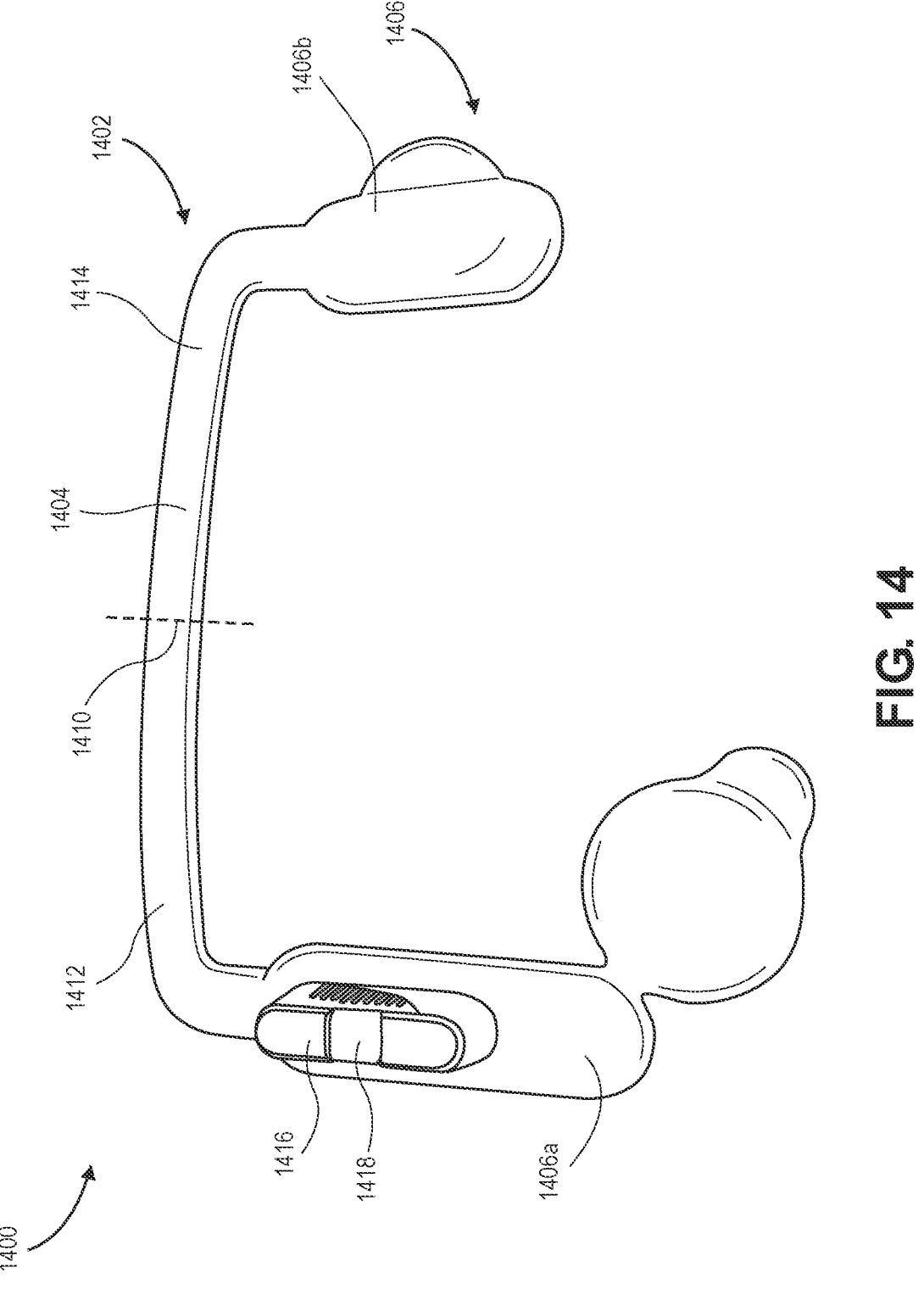
FIG. 14 illustrates another example device for detecting and monitoring health conditions of a subject, according to some embodiments of the disclosure.

FIG. 14 illustrates another example device 1400 for detecting and monitoring health conditions of a subject, according to some embodiments of the disclosure. In particular, FIG. 14 illustrates a front side of the device 1400 that is to be positioned away from the skin of a subject when worn by the subject.

The device 1400 may include a frame 1402. Components of the device 1400 may be mounted to the frame 1402 to maintain positions of the components relative to each other. In some embodiments, the frame 1402 may be available in different sizes, where the different sizes have different distances between the components or arrangements of the components to facilitate different body types and/or body sizes of a subject. In other embodiments, mounting locations of the components to the frame 1402 may be adjustable to adjust the locations of the components for different body types and/or body sizes of a subject. In some of the embodiments where the mounting locations are adjustable, ability to adjust the locations of the components may be limited to specific individuals (such as by requiring a special tool for adjustment that may not be made publicly available), which may prevent a subject from inadvertently adjusting the mounting locations to incorrect locations for operation.

The frame 1402 may include a main body 1404. The main body 1404 may extend in a first direction and may be curved. In other embodiments, the main body 1404 may be straight. Further, the frame 1402 may include one or more extensions 1406 that extend from the main body in one or more other directions. For example, the main body 1404 includes a first extension 1406a and a second extension 1406b coupled to the main body 1404 and that extend from the main body 1404 in the illustrated embodiment. The first extension 1406a may be coupled to the main body 1404 at a first end of the main body 1404 and the second extension 1406b may be coupled at a second end of the main body 1404, where the second end is opposite to the first end. The first extension 1406a and the second extension 1406b extend substantially (within 5 degrees) perpendicularly from the main body 1404 in the illustrated embodiment, however it is to be understood that the angles may be different in other embodiments. Further, the extensions 1406 are illustrated as being affixed to the main body 1404 in the illustrated embodiment. In other embodiments, the positions of the extensions 1406 along the main body 1404 may be adjustable.

In some embodiments, the main body 1404 may include rigid portions and one or more bend points between the rigid portions. For example, the main body 1404 includes a bend point 1410 (indicated by a dashed line), a first rigid portion 1412 located on a first side of the bend point 1410, and a second rigid portion 1414 located on a second side of the bend point 1410. The first rigid portion 1412 and the second rigid portion 1414 may each include a rigid material (such as a rigid metal, rigid plastic, or other rigid material) that maintains a rigidity of the rigid portions. In some embodiments, the rigid material may be surrounded by other material (such as fabric) that may be more comfortable against a skin of the subject. The bend point 1410 may include a flexible material that allows the first rigid portion 1412 and the second rigid portion 1414 to bend about the bend point 1410. In some embodiments, the flexible material may be the same material (such as fabric) that surrounds the rigid material and the bend point 1410 may be characterized by the absence of the rigid material. In other embodiments, the bend point 1410 may include a hinge rather than the flexible material. Further, an entirety of the main body 1404 may be flexible or rigid in other embodiments. The extensions 1406 may be rigid or flexible, and may be formed of the same material as some portion of the main body 1404 or may be formed of a different material.

The device 1400 may further include a control module 1416. The control module 1416 may be mounted to the frame 1402. The control module 1416 is mounted to the first extension 1406a in the illustrated embodiment, however it is to be understood that the control module 1416 may be mounted to other locations of the frame 1402 in other embodiments.

The control module 1416 may include one or more of the multi-modality sensing and measurement modules 112 (FIG. 2), the processor 202 (FIG. 2), the transmitter/receiver 204 (FIG. 2), the data storage 206 (FIG. 2), the memory 208 (FIG. 2), or some combination thereof. The control module 1416 may further include a battery for powering the device 1400. The control module 1416 may be coupled to one or more surface sensors of the device 1400, as described further in relation to FIG. 15. The control module 1416 may control operation of the surface sensors and may store data received from the surface sensors. In some embodiments, the control module 1416 may store the data, along with an indication of a time that the data was captured (such as time stamping the data), for future transfer of the data to a cloud (such as the cloud 110 (FIG. 1) and/or the cloud 308 (FIG. 3)). In other embodiments, the control module 1416 may further perform operations with the data prior to transfer of the data to the cloud. For example, the control module 1416 may analyze, trend, reduce, and/or fuse the data, or some portion thereof, prior to transfer of the data to the cloud.

In some embodiments, the control module 1416 may further include an orientation detection sensor. The orientation detection sensor may determine an orientation of the control module 1416, which may be utilized for determining an orientation of the subject. For example, the control module 1416 can determine whether a subject is standing, laying, or may determine an angle at which the subject is reclined based on the orientation measured by the orientation detection sensor. In some embodiments, the orientation detection sensor may comprise an accelerometer that can be utilized for determining the orientation of the control module 1416.

The control module 1416 may further include one or more switches 1418. The switches 1418 may comprise a button, a sliding switch, a throw switch, a toggle switch, a rotary switch, or some combination thereof. In the illustrated embodiment, the switch 1418 comprises a button. Actuation of the switch 1418 may be detected by the control module 1416 and may cause a procedure (such as the method 2400 (FIG. 24)) to be initiated. In some embodiments, a procedure initiated in response to the actuation of the switch 1418 may be dependent on an amount of time that the switch 1418 is actuated. For example, the switch 1418 being actuated in excess of a threshold time period may cause a current procedure to be halted or may restart the procedure.

While a shape of the frame 1402 and positioning of components mounted to the frame 1402 are described in relation to FIG. 14, it is to be understood that the shape of the frame 1402 and/or positioning of the components may be different in other embodiments. In particular, the shape of the frame 1402 and positioning of the components may be any shape or position that achieves the positioning of the surface sensors in accordance with one or more of the surface sensors positioning described throughout this disclosure, such as the positioning described in relation to FIGS. 26A-26G.

Figure 15:
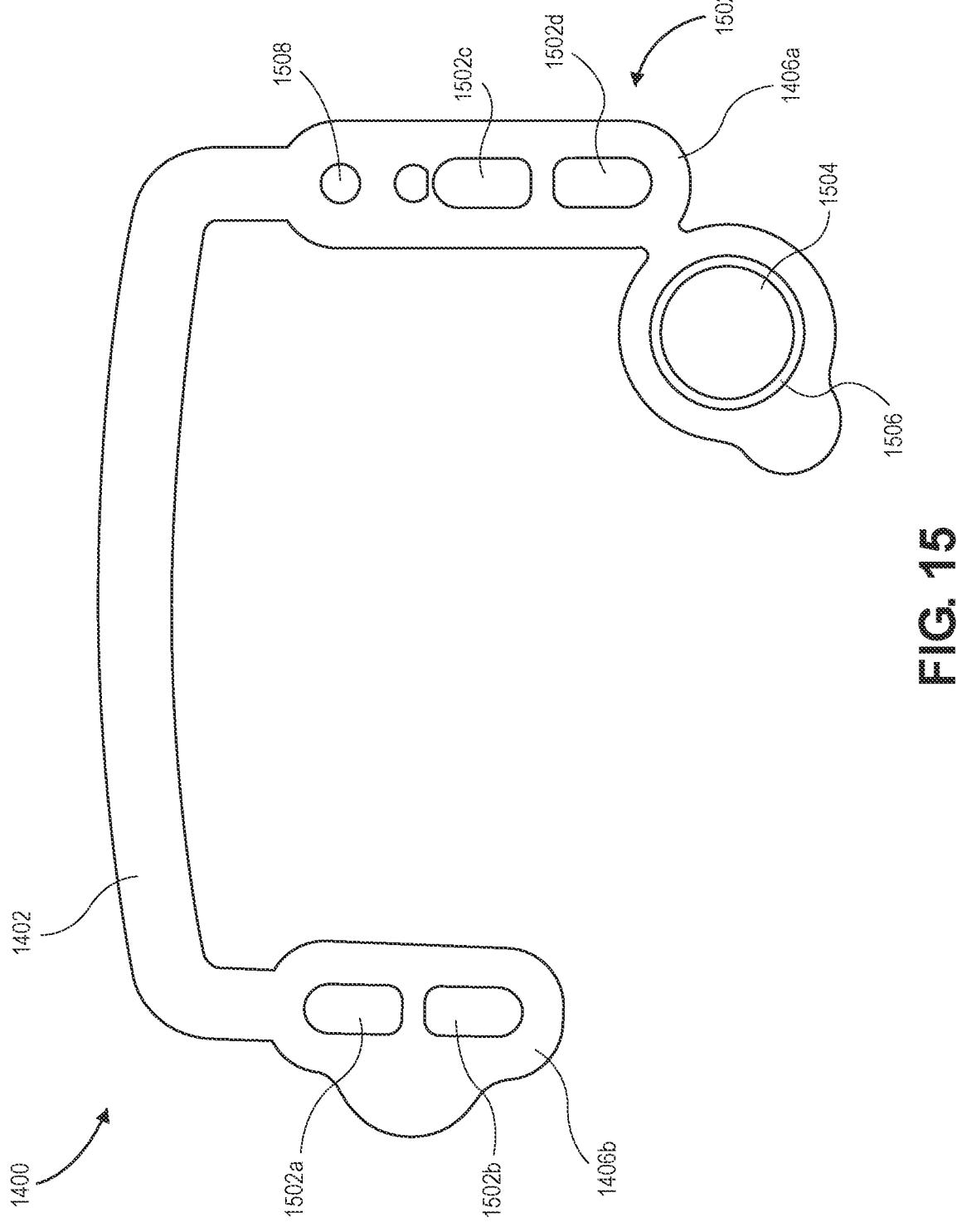
FIG. 15 illustrates a back side of the example device of FIG. 14 according to some embodiments of the disclosure.

FIG. 15 illustrates a back side of the example device 1400 of FIG. 14 according to some embodiments of the disclosure. In particular, FIG. 15 illustrates a side of the device 1400 that is to be positioned toward the skin of a subject when worn by the subject.

The device 1400 includes one or more surface sensors mounted to frame 1402. The surface sensors may include one or more of the features of the surface sensors described throughout this disclosure. The surface sensors may include electrodes, heart sound sensors, ultrasound sensors, PPG sensors, or some combination thereof. The surface sensors may be arranged to contact a surface of a skin of a subject when the device 1400 is worn by the subject.

The surface sensors may include one or more electrodes 1502. For example, the device 1400 includes four electrodes in the illustrated embodiment. The electrodes 1502 may include polished stainless-steel electrodes, platinum black electrodes, or some combination thereof. A plurality of the electrodes 1502 may be positioned in locations to measure a thoracic impedance when the device 1400 is worn by the subject. For example, the plurality of electrodes 1502 may be positioned against a chest of the subject, a neck of the subject, a stomach of the subject, or some combination thereof, when the device 1400 is worn by the subject. In some embodiments, the electrodes 1502 may be positioned in the locations indicated by FIGS. 26A-26G. In the illustrated embodiment, the device 1400 includes a first electrode 1502a and a second electrode 1502b located toward a first end of the main body 1404, and a third electrode 1502c and a fourth electrode 1502d located toward a second end of the main body 1404. In other embodiments, the device 1400 may have more or fewer electrodes, the electrodes may be located in different positions, or some combination thereof.

The electrodes 1502 located toward a same end of the main body 1404 may be located as close as possible in view of manufacturing and design considerations (such as allowing for space for proper adhesion of the electrodes by adhesives). For example, the distance between the electrodes 1502 located toward the same end may be separated by 0.5 cm in some embodiments. In particular, the first electrode 1502a may be separated from the second electrode 1502b by 0.5 cm, and the third electrode 1502c may be separated from the fourth electrode 1502d by 0.5 cm. In some embodiments, the distance between the electrodes located toward the same end may be separated by between 0.3 cm and 5 cm.

The electrodes 1502 located at opposite ends of the main body 1404 may be located at a distance to span a lung of a subject. For example, the first electrode 1502a and the second electrode 1502b may be separated from the third electrode 1502c and the fourth electrode 1502d by between 17 cm and 20 cm in some embodiments, where between 17 cm and 20 cm may be approximately the width of an adult human lung. In some embodiments, the first electrode 1502a and the second electrode 1502b may be separated from the third electrode 1502c and the 1502d by 19 cm. In other embodiments, the distance by which the first electrode 1502a and the second electrode 1502b are separated from the third electrode 1502c and the fourth electrode 1502d may be adjustable to fit different sized subjects.

While the electrodes 1502 are illustrated as being substantially oval-shaped in the embodiment, it is to be understood that the electrodes may be any shape, including circle-shaped, rectangle-shaped, triangle-shaped, diamond-shaped, or some combination thereof. Further, the electrodes 1502 may comprise segmented electrodes in some embodiments, where each of the electrodes 1502 may be formed of multiple pieces of material. For example, the electrodes 1502 illustrated may be segmented into halves or quarters. Further, the size of the electrodes 1502 (or segments thereof) may be any size suitable for performance of the measurements, such as having a surface area of between 0.9 centimeters squared ($cm^2$) and 19.7 $cm^2$.

The surface sensors may further include one or more sound sensors. The sound sensors may include piezo-electric sensors, acoustic sensors, or some combination thereof. In the illustrated embodiment, the device 1400 includes a sound sensor 1504. The sound sensor 1504 is located on the first extension 1406a. In other embodiments, the sound sensor 1504 may be located at other positions along the frame 1402. The sound sensor 1504 may be positioned against a chest of the subject and adjacent to a heart of the subject when the device 1400 is worn by the subject. The sound sensor 1504 may detect sounds of the heart of the subject during operation. The sound sensor 1504 may have a curved surface that is to be positioned against the skin of the subject, where the curve may provide greater surface contact with the skin of the subject and provide good contact with the skin. Further, an edge 1506 of the sound sensor 1504 may be protruded and the skin of the subject may deform to fill the cavity formed by the protrusion. The protrusion of the edge 1506 may assist in blocking external sounds from affecting the capture of the sounds of the heart captured by the sound sensor 1504. In some embodiments, gel may be applied to a surface of the sound sensor 1504 that is to contact the skin of the subject, where the gel may reduce inadvertent movement of the sound sensor 1504, reduce loss of sound transmission that may be caused by air located between the sound sensor 1504 and the skin of the subject, or some combination thereof.

The surface sensors may include a combination sensor 1508. The combination sensor 1508 may include a reference electrode (such as the reference electrode 1002e (FIG. 10)) and a temperature sensor (such as the temperature sensor 810 (FIG. 8)). The reference electrode of the combination sensor 1508 may be utilized to set a body of the subject at a certain potential, which may minimize noise detected by the other electrodes 1502. In some embodiments, the reference electrode may be utilized to detect a potential of the body of the subject, which may be utilized when processing data captured by the other electrodes 1502 to compensate for any noise.

The combination sensor 1508 may be smaller than the other electrodes in some embodiments. For example, the combination sensor 1508 may have a surface area of 3.1416 $cm^2$, and the first electrode 1502a, the second electrode 1502b, the third electrode 1502c, and the fourth electrode 1502d may have a surface area of 12.5664 $cm^2$ or more. In other embodiments, the combination sensor 1508 may be the same size as the other electrodes 1502. Further, the distance between the combination sensor 1508 and the other electrodes 1502 may be 0.5 cm or greater. For example, the combination sensor 1508 may be located 0.5 cm or greater from the third electrode 1502c in the illustrated embodiment.

The temperature sensor of the combination sensor 1508 may contact the skin of the subject and may measure the temperature of the skin of the subject. In other embodiments, temperature sensor may be located near the electrodes or may be embedded in area of one or more of the pads of the electrodes. Further, the device 1400 may include an additional temperature sensor that is to measure a temperature of the environment in which the subject is located in other embodiments.

In other embodiments, the device 1400 may further include additional types of sensors, including any of the types of sensors described throughout this disclosure. For example, the device 1400 may include a pulse oximetry sensor in some embodiments. The pulse oximetry sensor may be located near the electrodes 1502, near the combination sensor 1508, or at any other position along the frame 1402.

The surface sensors may be coupled to the control module 1416 (FIG. 14) and operation of the surface sensors may be controlled by the control module 1416. In particular, the surface sensors may be coupled to the control module 1416 by electrical conductors (such as the electrical conductors 808 (FIG. 8)). The electrical conductors may comprise wires, circuits, or some combination thereof. The electrical conductor, or some portion thereof, may be flexible. In particular, at least a portion of the electrical conductors that extend across the bend point 1410 (FIG. 14) may be flexible and may be designed to be bent multiple times without becoming inoperable. The electrical conductors may be located within the frame 1402, along the frame 1402, or some combination thereof. In embodiments where the bend point 1410 comprises a hinge, the electrical conductors may include portions of the hinge that are designed to be electrically conductive.

The control module 1416 may control operation of the surface sensors and receive data of the surface sensors via the electrical conductors. For example, the control module 1416 may define when sound data is to be captured by the sound sensor 1504, and may receive and store the sound data from the sound sensor 1504. Further, the control module 1416 may determine which portion of the electrodes 1502 are to apply electrical force (such as voltage and/or current) and which portion of the electrodes are to detect the changes (such as increase/decrease in voltage drop or current flow) affected by the application of the electrical force. For example, the control module 1416 may cause the first electrode 1502a and the second electrode 1502b to apply the electrical force, while the control module 1416 causes the third electrode 1502c, and the fourth electrode 1502d to detect the changes. In some embodiments, the changes detected by one of the electrodes, such as the reference electrode of the combination sensor 1508, may be used as reference data and may be utilized for compensation of data captured by the other electrodes. In other embodiments, the device 1400 may include a particular electrode that may be utilized as a reference electrode and capture reference data.

In some embodiments, the control module 1416 may cause one or more of the electrodes to apply alternating currents as the electrical force, and may cause one more of the electrodes to detect the changes caused by the application of the alternating currents. For example, the control module 1416 may cause the first electrode 1502a and the second electrode 1502b to apply alternating currents, while the control module 1416 causes the third electrode 1502c and the fourth electrode 1502d to detect the changes. The control module 1416 may determine equi-potentials based on the detected changes, where the equi-potentials determined from the third electrode 1502c and the fourth electrode 1502d may be utilized to perform EIT. Further, the control module 1416 may vary the frequency of the alternating current in some embodiments. In these embodiments, the changes detected may include an amount of capacitance and/or resistance between the electrodes applying the alternating currents and the electrodes detecting the changes, in addition to the equi-potentials. The amount of capacitance and/or resistance may be used for impedance spectroscopy to produce an impedance spectrum representation for the paths between the electrodes applying the alternating currents and the electrodes detecting the changes. Further, the equi-potentials may also be utilized to perform EIT when the frequency of the alternating current is varied.

Figure 16:
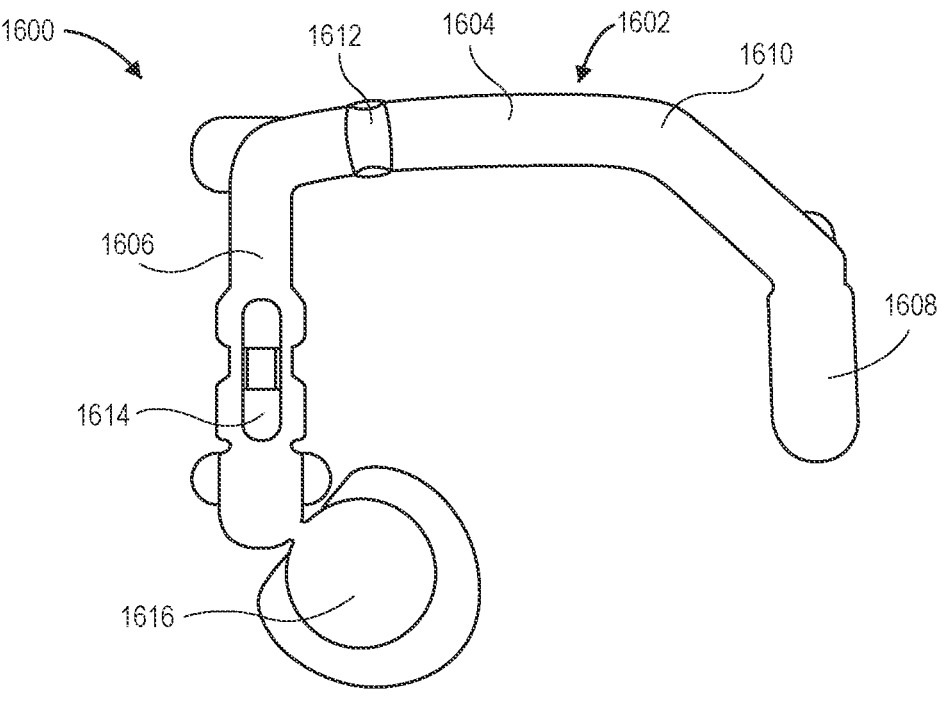
FIG. 16 illustrates another example device for detecting and monitoring health conditions of a subject, according to some embodiments of the disclosure.

FIG. 16 illustrates another example device 1600 for detecting and monitoring health conditions of a subject, according to some embodiments of the disclosure. The device 1600 may include one or more of the features of the device 1400 (FIG. 14). FIG. 16 illustrates a front side of the device 1600 that is to be positioned away from the skin of a subject when worn by a user.

The device 1600 may include a frame 1602. The frame 1602 may include one or more of the features of the frame 1402 (FIG. 14). For example, the components of the device 1600 may be mounted to the frame 1602 to maintain positions of the components relative to each other. The frame 1602 may include a main body 1604 with a first extension 1606 and a second extension 1608 extending from the main body 1604. In the illustrated embodiment, the main body 1604 includes a bend 1610 that causes a first portion of the frame 1602 to extend in a first direction and a second portion of the frame 1602 to extend in a second direction. The first extension 1606 and the second extension 1608 may extend from the main body 1604 in a third direction, where the third direction is different than the first direction and the second direction.

The device 1600 may further include a holder 1612. The device 1600 may be flexible and/or have a bend point that allows a portion of the main body 1604 to fold onto another portion of the main body 1604. The holder 1612 may interact with the portion of the main body 1604 and maintain the device 1600 in the folded arrangement. For example, the holder 1612 may make a friction contact with the portion of the main body 1604 to maintain the device 1600 in the folded arrangement.

The device 1600 may include a control module 1614 mounted to the first extension 1606. The control module 1614 may include one or more of the features of the control module 1416 (FIG. 14). Further, the first extension 1606 may include an island 1616. The island 1616 may be utilized for mounting of a sound sensor, as described further in relation to FIG. 17.

Figure 17:
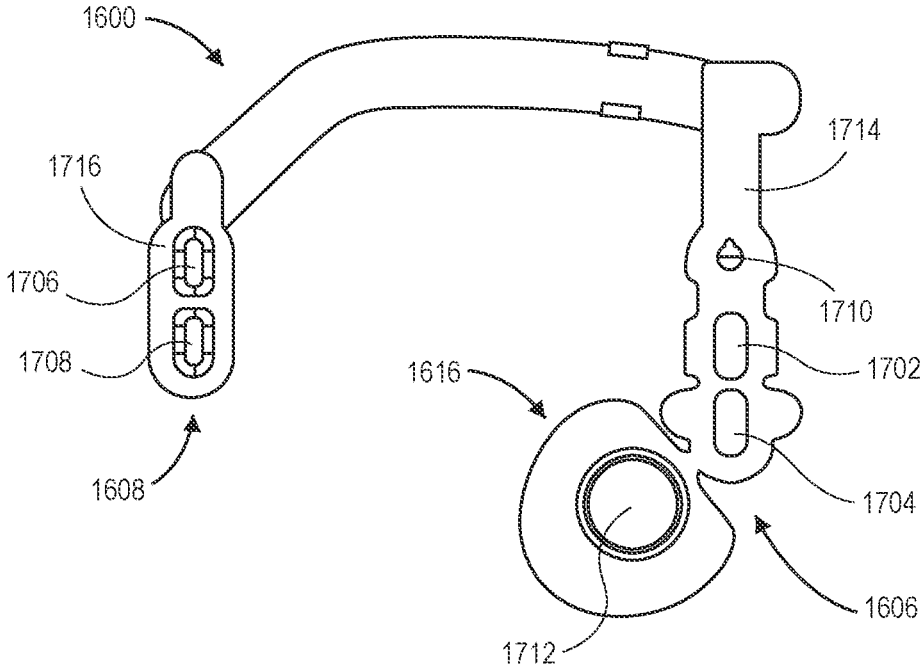
FIG. 17 illustrates a back side of the example device of FIG. 16, according to some embodiments of the disclosure.

FIG. 17 illustrates a back side of the example device 1600 of FIG. 16, according to some embodiments of the disclosure. In particular, FIG. 17 illustrates a side of the device 1600 that is to be positioned toward the skin of a subject when worn by the subject.

The device 1600 includes one or more surface sensors mounted to the frame, where the surface sensors include one or more of the features of the surface sensors described in relation to FIG. 15. The surface sensors may include a first electrode 1702 and a second electrode 1704 mounted to the first extension 1606, and a third electrode 1706 and a fourth electrode 1708 mounted to the second extension. The surface sensors may further include a combination sensor 1710 mounted to the first extension 1606, where the combination sensor 1710 includes one or more of the features of the combination sensor 1508 (FIG. 15). The surface sensors may further include a sound sensor 1712 mounted to the island 1616.

FIG. 17 further illustrates adhesives applied to the device 1600. In particular, a first adhesive portion 1714 is located on the first extension 1606 and a second adhesive portion 1716 is located on the second extension 1608. The first adhesive portion 1714 and the second adhesive portion 1716 each may include an adhesive and a cover. When the cover is removed, the adhesive may be exposed and can be utilized to affix the device 1600 to the skin of the subject. For example, the first adhesive portion 1714 may affix the first extension 1606 and the second adhesive portion 1716 may affix the second extension 1608 to the skin of the subject.

Figure 18:
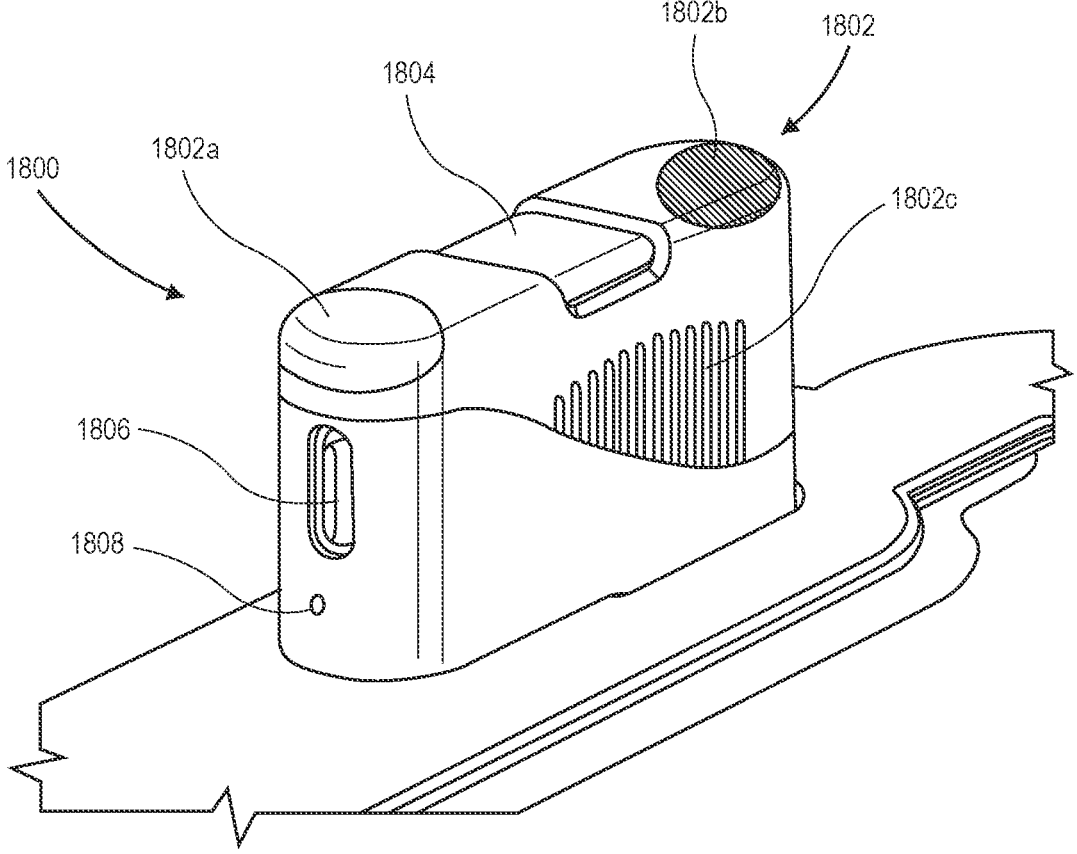
FIG. 18 illustrates an example control module, according to some embodiments of the disclosure.

FIG. 18 illustrates an example control module 1800, according to some embodiments of the disclosure. The control module 1800 may include one or more of the features of the control modules described throughout this disclosure, such as the control module 716 (FIG. 7) and/or the control module 1416 (FIG. 14). Further, the control module 1800 may be implemented in place of the control modules described throughout this disclosure.

The control module 1800 may include one or more of the multi-modality sensing and measurement modules 112 (FIG. 2), the processor 202 (FIG. 2), the transmitter/receiver 204 (FIG. 2), the data storage 206 (FIG. 2), the memory 208 (FIG. 2), or some combination thereof. The control module 1800 may further include a battery for powering a device that implements the control module 1800. The control module 1800 may be coupled to one or more surface sensors of the device. The control module 1800 may control operation of the surface sensors and may store data received from the surface sensors. In some embodiments, the control module 1800 may store the data, along with an indication of a time that the data was captured (such as time stamping the data), for future transfer of the data to a cloud (such as the cloud 110 (FIG. 1) and/or the cloud 308 (FIG. 3)). In other embodiments, the control module 1800 may further perform operations with the data prior to transfer of the data to the cloud. For example, the control module 1800 may analyze, trend, reduce, and/or fuse the data, or some portion thereof, prior to transfer of the data to the cloud.

In some embodiments, the control module 1800 may further include an orientation detection sensor. The orientation detection sensor may determine an orientation of the control module 1800, which may be utilized for determining an orientation of the subject. For example, the control module 1800 can determine whether a subject is standing, laying, or can determine an angle at which the subject is reclined based on the orientation measured by the orientation detection sensor. In some embodiments, the orientation detection sensor may comprise an accelerometer that can be utilized for determining the orientation of the control module 1800.

The control module 1800 may further include one or more indicators 1802. For example, the control module 1800 includes a first indicator 1802a and a second indicator 1802b in the illustrated embodiment. The indicators 1802 may indicate a status of the device. For example, the indicators 1802 may indicate a status of the electronics of the device, an orientation of the subject (or instructions for the subject to transition to a proper orientation for performance of an operation by the device), data transmission status, power status, operational status, or some combination thereof. The indicators 1802 may include visual indicators, audible indicators, motion indicators (such as an indicator that produces a physical force including vibration), or some combination thereof. In the illustrated embodiment, the indicators 1802 each comprise a light that may light up to indicate the status of the device. In other embodiments, the indicators 1802 may include lights, displays, speakers, or some combination thereof.

In some embodiments, each of the indicators 1802 may include a multi-colored light (such as multi-colored LEDs) or multiple lights of different colors (such as different colored LEDs). In some embodiments, the indicators 1802 may emit green, yellow, and blue light. Depending on the color of the light that is lit, a sequence of the light being emitted, whether the light is blinking, and/or whether the light is pulsating, different states of the device may be indicated. For example, a first color light may indicate that the device is connected to a communications network when lit, the device is ready to connect to the communications network when blinking, and/or is exchanging data with the communications network when pulsating. A second color light may indicate that the device is in a pre-reading mode when lit, and/or is measuring an ECG of the subject when blinking. A third color light may indicate that the device is fully charged when lit, is charging when pulsating, and/or is in a low battery state when blinking. Further, in some embodiments, sequences of the light being emitted may indicate a measurement is being performed, an orientation of the device (as determined by the position of the subject) is proper or requires adjustment, one or more of the surface sensors is not properly applied to the subject, measurement has been completed, or some combination thereof.

The indicators 1802 may further include a speaker 1802*c* to emit sound in some embodiments. The speaker 1802*c* may emit sounds (such as beeps and/or tones) that indicate a status of the device and/or supplement the first indicator 1802*a* and the second indicator 1802*b* in indicating a status of the device. For example, the speaker 1802*c* may emit beeps and/or tones to indicate one or more of the surface sensors is not properly applied to the subject, an orientation of the device requires adjustment, measurement has been completed, or some combination thereof.

The control module 1800 may further include a switch 1804 (such as a button, a sliding switch, a throw switch, a toggle switch, or a rotary switch). In the illustrated embodiment, the switch 1804 comprises a button. Actuation of the switch 1804 may be detected by the control module 1800 and may cause a procedure (such as the method 2400 (FIG. 24)) to be initiated. In some embodiments, a procedure initiated in response to the actuation of the switch 1804 may be dependent on an amount of time that the switch 1804 is actuated. For example, the switch 1804 being actuated in excess of a threshold time period may cause a current procedure to be halted or may restart the procedure.

The control module 1800 may further include a reset pin 1808. The reset pin 1808 may comprise a button in the illustrated embodiment. Actuation of the reset pin 1808 may be detected by the control module 1800 and may cause the control module 1800 to be reset. In particular, actuation of the reset pin 1808 may cause the control module 1800 to perform a hard restart in some embodiments.

The control module 1800 may further include a wired connection port 1806. The wired connection port 1806 comprises a universal serial bus type-C (USB-C) port in the illustrated embodiment. A charger and/or a base station (such as the base station 1204 (FIG. 12) and/or the base station 1300 (FIG. 13)) may be coupled to the wired connection port 1806 via a wire for charging a battery of the control module 1800. In some embodiments, the base station and/or another computer device may be coupled to the wired connection port 1806 via a wire for communicating data between the control module 1800 and the base station and/or another computer device, updating software and/or firmware of the control module 1800, or some combination thereof.

Figure 19:
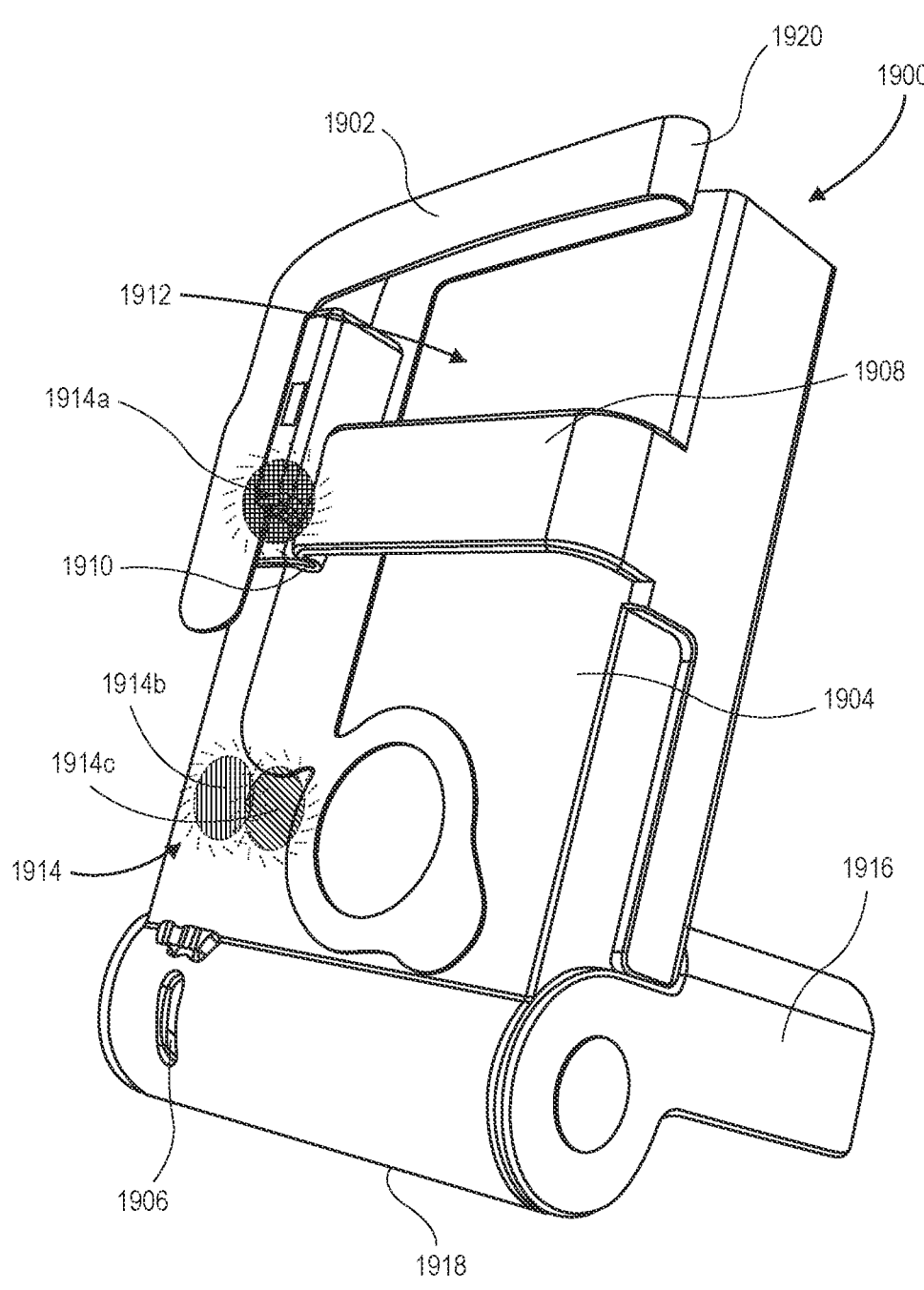
FIG. 19 illustrates another example base station, according to some embodiments of the disclosure.

FIG. 19 illustrates another example base station 1900, according to some embodiments of the disclosure. The base station 1900 may include one or more of the features of the base station 1204 (FIG. 12) and/or the base station 1300 (FIG. 13). The base station 1900 is illustrated with a device 1902 (which may include one or more of the features of the device 1400 (FIG. 14)) mounted to the base station 1900. When the device 1902 is mounted to the base station 1900, the device 1902 may be folded at a bend point 1920, where the bend point 1920 includes one or more of the features of the bend point 710 (FIG. 7) and/or the bend point 1410 (FIG. 14).

The base station 1900 may include a housing 1904. The housing 1904 may comprise a main body of the base station 1900 and may house electronics of the base station 1900 within the housing 1904. For example, the housing 1904 may house a processor (such as the processor 202 (FIG. 2)), a transmitter/receiver (such as the transmitter/receiver 204 (FIG. 2)), a data storage (such as the data storage 206 (FIG. 2)), a memory (such as the memory 208 (FIG. 2)), or some combination thereof.

The housing 1904 may include a wired connection port 1906. The wired connection port 1906 comprises a USB-C port in the illustrated embodiment. A wire may be coupled between the wired connection port 1906 and a wired connection port (such as the wired connection port 1806 (FIG. 18)) of the device 1902 to couple the electronics of the base station 1900 with electronics of the device 1902. When coupled, the base station 1900 may charge the device 1902 and/or exchange data with the device 1902.

The base station 1900 may further include an arm 1908. The arm 1908 may retain the device 1902 when the device 1902 is mounted to the base station 1900. The arm 1908 may be coupled to the housing 1904 and extend across a side of the housing 1904 in the illustrated embodiment. The side of the housing 1904 may be a front side 1912 of the housing 1904. A portion of the device 1902 may be located between a portion of the arm 1908 and the housing 1904 when the device 1902 is mounted to the base station 1900. The portion of the arm 1908 can apply pressure to the portion of the device 1902 to maintain the position of the device 1902 when mounted to the base station 1900. The arm 1908 may extend substantially (within 5 degrees) parallel to the front side 1912 of the housing 1904, and have an offset portion 1910 that extends toward the front side 1912 of the housing 1904 and applies pressure toward the front side 1912 of the housing 1904. In some embodiments, the offset portion 1910 may comprise a curved portion that extends from the substantially parallel portion of the arm 1908 toward the front side 1912 of the housing 1904. The offset portion 1910 may apply the pressure to the device 1902 when the device 1902 is mounted to the housing 1904 to maintain the device 1902 in position against the housing 1904.

The base station 1900 may include one or more indicators 1914. The indicators 1914 may include visual indicators, audible indicators, or some combination thereof. In the illustrated embodiment, the base station 1900 includes a first indicator 1914*a*, a second indicator 1914*b*, and a third indicator 1914*c*. The indicators 1914 comprise different colored lights (such as colored LEDs) in the illustrated embodiment. In particular, the first indicator 1914*a* comprises a yellow light, the second indicator 1914*b* comprises an amber light, and the third indicator 1914*c* comprises a green light in the illustrated embodiment. In other embodiments, the indicators 1914 may be different colors than illustrated, may all be the same color, or some combination thereof.

The indicators 1914 may indicate a status of the base station 1900. For example, the indicators 1914 may indicate as statuses of the base station 1900 that the base station 1900 is booting up, whether the device 1902 is coupled to the base station 1900, whether the base station is connected to a network (such as the communications network 108 (FIG. 1)) or the cloud (such as the cloud 110 (FIG. 1)), whether the base station 1900 is exchanging data with the network or the cloud, a charge status of the device 1902 when coupled to the base station 1900, or some combination thereof. The indicators 1914 may indicate the status of the base station 1900 based on the color of the indicators 1914 that are illuminated, whether the indicators 1914 are blinking or solid, or some combination thereof. Further, the indicators 1914 may be utilized in combination with indicators of the device 1902 (such as the indicators 1802 (FIG. 18)) to indicate a status of the base station 1900 and/or a status of the device 1902.

The base station 1900 may further include a cover 1916. The cover 1916 may be rotatably coupled to the housing 1904, and may rotate between a cover position and a stand position. In the illustrated embodiment, the cover 1916 is rotatably coupled toward a lower end 1918 of the housing 1904. When in the stand position, the cover 1916 may be rotated around a back side of the housing 1904 and may contact the back side of the housing 1904, the back side of the housing 1904 being opposite to the front side 1912 of the housing 1904. The cover 1916 may extend substantially perpendicular from the back side of the housing 1904. When the cover 1916 is in the stand position and placed on a surface, the housing 1904 may rest on the lower end 1918 and tilt backward, where the cover 1916 contacts the surface and prevents the housing 1904 from tipping over backward. The housing 1904 can set on the lower end 1918 and the cover 1916 on the surface.

Figure 20:
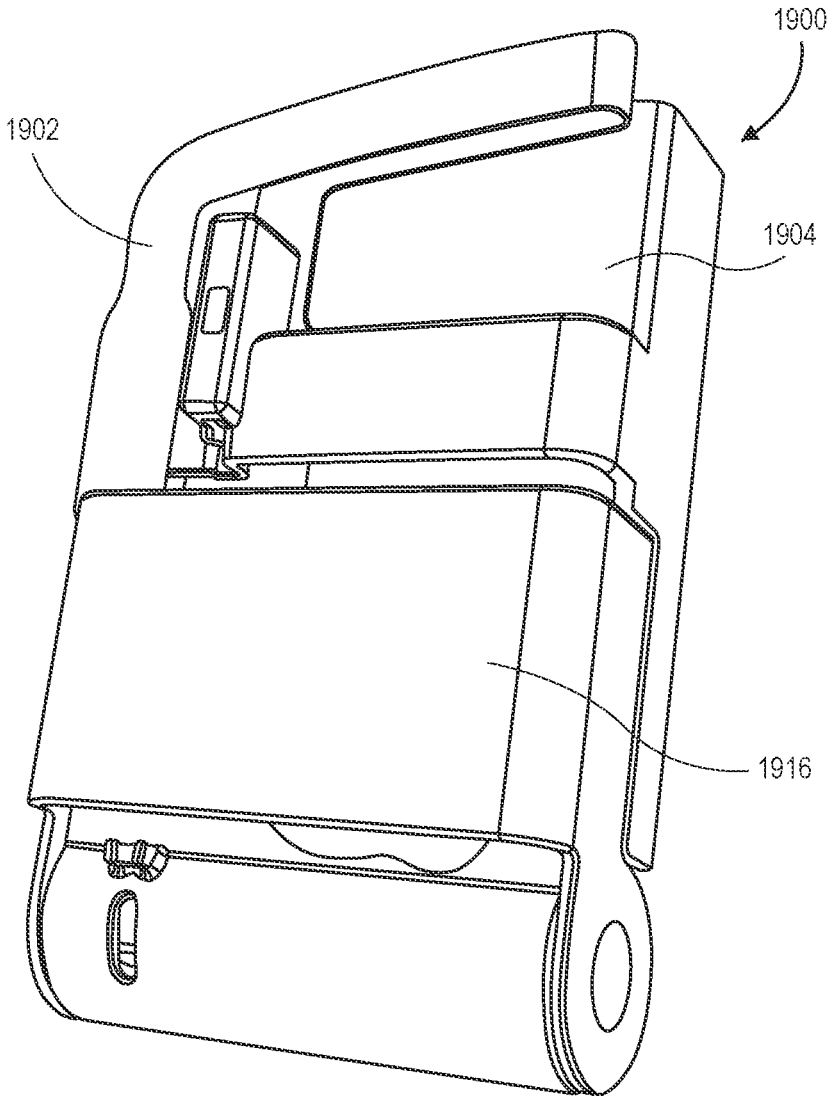
FIG. 20 illustrates the base station of FIG. 19, according to some embodiments of the disclosure.

FIG. 20 illustrates the base station 1900 of FIG. 19, according to some embodiments of the disclosure. In particular, the base station 1900 is illustrated with the cover 1916 in a cover position. When in the cover position, the cover 1916 is rotated to extend across the front side 1912 of the housing 1904, where a portion of the cover 1916 extends substantially (within 5 degrees) parallel to the front side 1912 of the housing 1904. The cover 1916 may cover a portion of the device 1902 and a portion of the front side 1912 of the housing 1904 when in the cover position. Accordingly, the cover 1916 may protect the portion of the device 1902 and the portion of the front side 1912 from damage when in the cover position.

Figure 21:
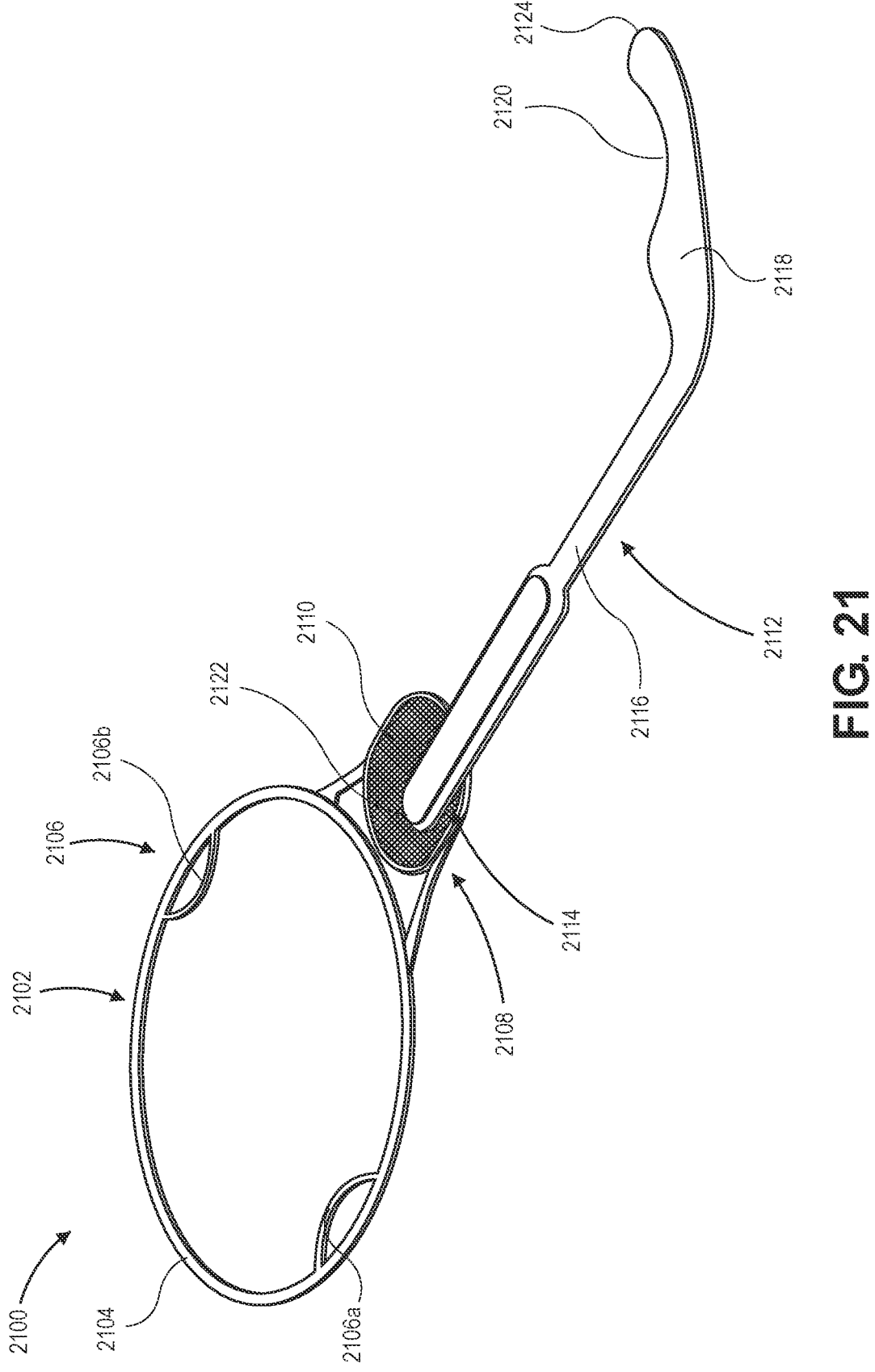
FIG. 21 illustrates an example guide, according to some embodiments of the disclosure.

FIG. 21 illustrates an example guide 2100, according to some embodiments of the disclosure. In some instances, the guide 2100 may be referred to as a stetho guide. The guide 2100 may be utilized for positioning of a system (such as the system 102 (FIG. 1) and/or the system 1100 (FIG. 11)) or a device (such as the device 304 (FIG. 3), the device 400 (FIG. 4A), the device 500 (FIG. 5), the device 600 (FIG. 6), the device 700 (FIG. 7), the device 1000 (FIG. 10), the device 1400 (FIG. 14), and/or the device 1902 (FIG. 19)) on a subject. In particular, the guide 2100 may be worn by the subject and the guide may indicate a position where the system or device should be positioned on the subject when worn.

The guide 2100 may include a neck piece 2102 that is to be worn around a neck of the subject when positioning the system or the device. The neck piece 2102 may include a necklace portion 2104 that is to be placed around the neck of the subject. The necklace portion 2104 may be semirigid in some embodiments, thereby allowing the necklace portion 2104 to maintain a shape absent forces exceeding a threshold force while allowing some flexibility in response to application of forces exceeding the threshold force to facilitate placement of the necklace portion 2104 around the neck of the subject. In other embodiments, the necklace portion 2104 may be rigid. The necklace portion 2104 has a circular shape with hollow center through which the neck of the subject is to be positioned in the illustrated embodiment. In other embodiments, the necklace portion 2104 may have other shapes, such as being oval-shaped or polygon-shaped.

The guide 2100 may further include one or more positioning elements 2106 coupled to the necklace portion 2104. For example, the guide 2100 includes a first positioning element 2106a and a second positioning element 2106b in the illustrated embodiment. The positioning elements 2106 may extend inward from the necklace portion 2104 and may contact the neck of the subject to provide further positioning in addition to the necklace portion 2104. In particular, the first positioning element 2106a is to contact a first side of the neck of the subject and the second positioning element 2106b is to contact a second side of the neck of the subject, the second side being opposite to the first side, and apply forces to the sides of the neck of the subject to center the necklace portion 2104 on the neck of the subject. The positioning elements 2106 may be semirigid, where a rigidity of the positioning elements 2106 is less than the rigidity of the necklace portion 2104. Accordingly, the necklace portion 2104 may retain shape while the positioning elements 2106 may flex and apply force to the neck of the subject when the neck piece 2102 is worn by the subject. In some embodiments, the positioning elements 2106 may be omitted.

The neck piece 2102 may further include a mounting portion 2108. The mounting portion 2108 may be coupled to the necklace portion 2104 and may be located at a front of the subject when the neck piece 2102 is worn as intended. In some embodiments, the mounting portion 2108 may be coupled to the necklace portion 2104 and extend outwards from the necklace portion 2104. The mounting portion 2108 may include a mounting element 2110 utilized to mount items to the neck piece 2102. In the illustrated embodiment, the mounting element 2110 comprises a hook and loop material (in particular, a hook material or a loop material of a hook and loop fastener) to facilitate mounting of items to the neck piece 2102. In other embodiments, the mounting element 2110 may comprise other materials to facilitate mounting of items to the neck piece 2102, such as an adhesive, a flat surface to which a suction cup can be mounted, one or more apertures to which fasteners may be utilized for mounting the items, and/or one or more fasteners for mounting the items. The mounting element 2110 may allow for the items to be mounted in multiple different positions to the mounting portion 2108.

The guide 2100 may further include a positioning piece 2112. The positioning piece 2112 may couple to the neck piece 2102, and indicate proper positioning of the system or device when coupled to the neck piece 2102 and when the neck piece 2102 is worn by the subject. The positioning piece 2112 may include an elongated member 2116. The elongated member 2116 may comprise a rigid material and may maintain shape.

The positioning piece 2112 may further comprise a mounting portion 2114. The mounting portion 2114 may be coupled to the elongated member 2116 and may be located toward a first end 2122 of the positioning piece 2112. The mounting portion 2114 may include a mounting element that couples to the mounting element 2110 of the neck piece 2102 to mount the positioning piece 2112 to the neck piece 2102. The mounting element of the mounting portion 2114 may comprise a hook and loop material (in particular, a hook material or a loop material of a hook and loop fastener, where the hook and loop material of the mounting element of the mounting portion 2114 is the opposite material from the mounting element 2110) to facilitate mounting of the positioning piece 2112 to the neck piece 2102. In other embodiments, the mounting element of the mounting portion 2114 may comprise other materials to facilitate mounting of the positioning piece 2112, such as an adhesive, a suction cup, one or more apertures to which fasteners may be utilized for mounting, and/or one or more fasteners for mounting. The mounting portion 2114 may be mounted to multiple different positions on the mounting portion 2108, thereby allowing adjustment of the location of positioning piece 2112 to facilitate different sizes of subjects that may utilize the guide 2100.

The positioning piece 2112 may further include an indication portion 2118. The indication portion 2118 may indicate a position where a portion of the system or device should be positioned on the subject. The indication portion 2118 may have an edge 2120 of the indication portion 2118 that is shaped to match an edge of the system or device. In particular, the edge of the system or device is to be positioned adjacent to the edge 2120 of the indication portion 2118 for proper positioning of the system or device on the subject. In the illustrated embodiment, the edge 2120 of the indication portion 2118 includes two curves that match a portion of the system or device and indicate proper positioning of the system or device adjacent to the two curves. The indication portion 2118 may be located at a second end 2124 of the positioning piece 2112, the second end 2124 being opposite to the first end 2122.

While the guide 2100 in the illustrated embodiment has two pieces (i.e., the neck piece 2102 and the positioning piece 2112), it is to be understood that guide 2100 may comprise one or more pieces, where the features of neck piece 2102 and the positioning piece 2112 may be implemented by the one or more pieces. For example, the neck piece 2102 and the positioning piece 2112 may be implemented as a single piece in some embodiments, where the positioning piece 2112 is affixed to the neck piece 2102.

Figure 22:
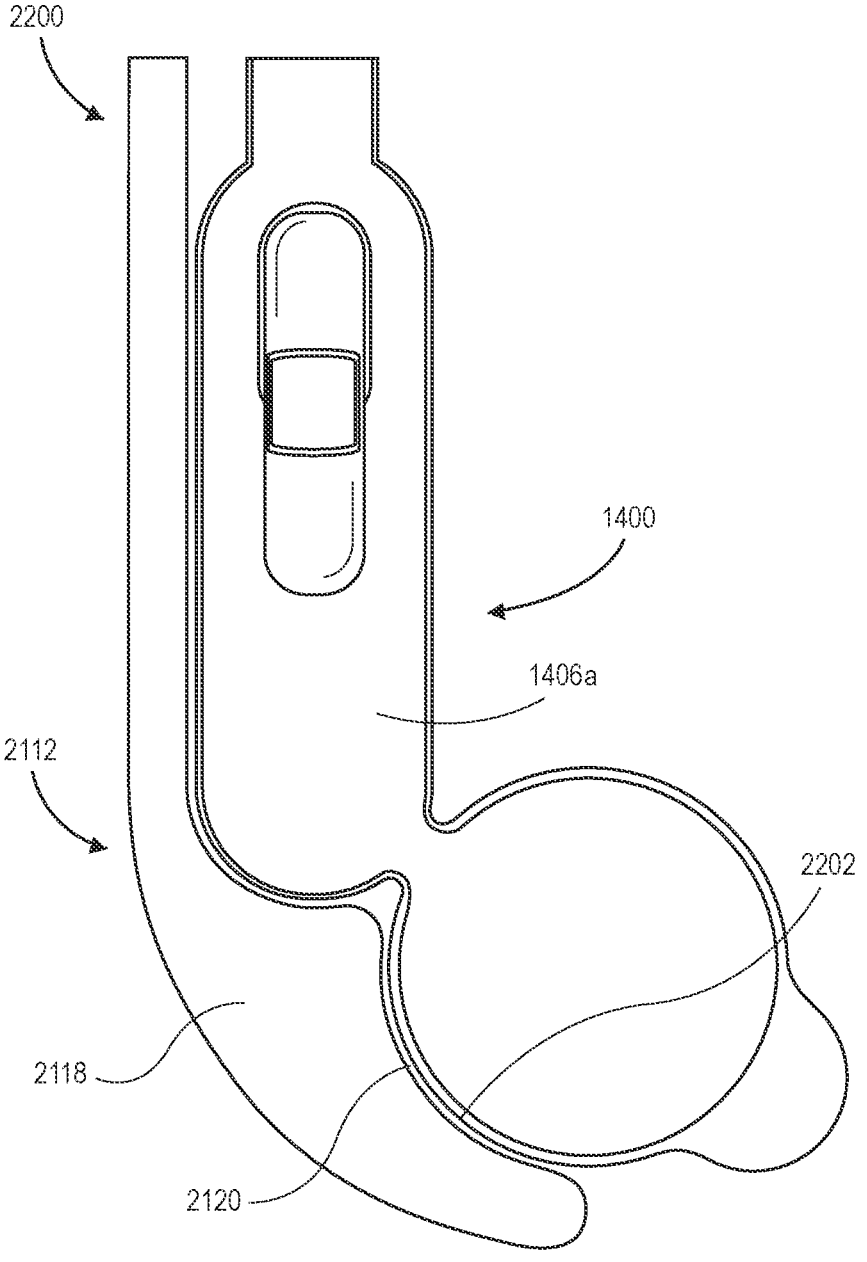
FIG. 22 illustrates an example positioning arrangement, according to some embodiments of the disclosure.

FIG. 22 illustrates an example positioning arrangement 2200, according to some embodiments of the disclosure. In particular, FIG. 22 illustrates a portion of the positioning piece 2112 of FIG. 21 and a portion of the device 1400 of FIG. 14, where the positioning piece 2112 and the device 1400 are positioned as would be positioned for positioning of the device 1400 on the subject.

The portion of the positioning piece 2112 illustrated includes the indication portion 2118. The indication portion 2118 includes the edge 2120. The device 1400 is positioned adjacent to the edge 2120 of the indication portion 2118. In particular, an edge 2202 of the device 1400 is positioned adjacent to the edge 2120 of the indication portion. In the illustrated embodiment, the edge 2202 is an edge of the first extension 1406a of the device 1400, where a portion of the first extension 1406a that includes the edge 2202 is located adjacent to the indication portion 2118. The device 1400 may be affixed to the subject (such as via adhesives 900 (FIG. 9)) while positioned adjacent to the indication portion

2118. The guide 2100 (FIG. 21) may be removed from the subject after the device 1400 has been positioned.

Figure 23:
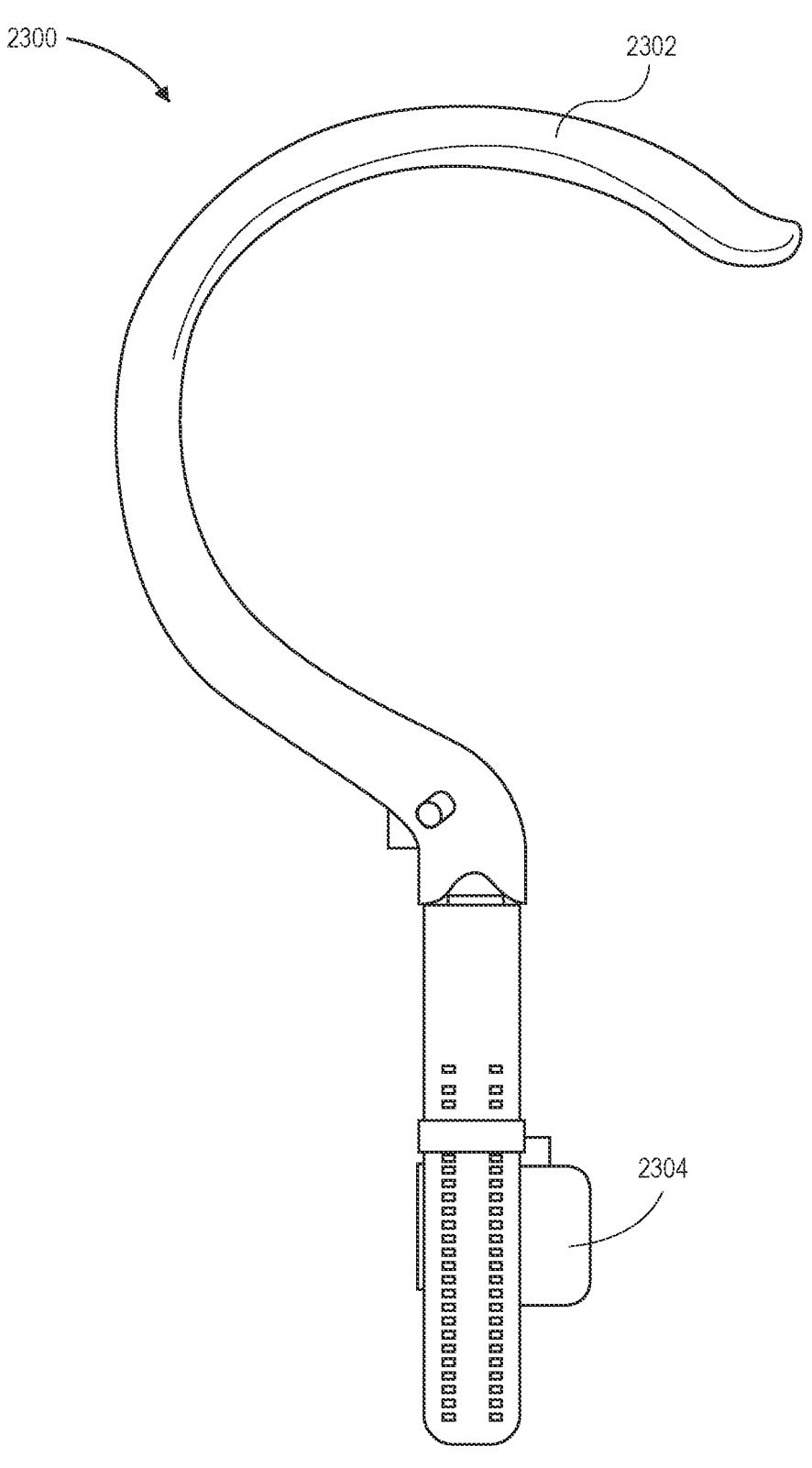
FIG. 23 illustrates another example guide, according to some embodiments of the disclosure.

FIG. 23 illustrates another example guide 2300, according to some embodiments of the disclosure. The guide 2300 may include one or more of the features of the neck piece 2102 (FIG. 21). The guide 2300 may be utilized with a positioning piece (such as the positioning piece 2112 (FIG. 21)) to position a device on a subject.

The guide 2300 may include a hook portion 2302, where the hook portion 2302 has a hook shape. When positioned on the subject, a neck of the subject may be located within opening formed by the hook portion 2302, with the hook of the hook portion 2302 extending along a back of a neck of the subject. The guide 2300 may be supported on the subject by the hook portion 2302 being placed around the neck of the subject.

The guide 2300 may further include a socket 2304. The socket 2304 may be coupled to the hook portion 2302. Further, the socket 2304 may engage with a device and facilitate positioning of the device on the subject. When the hook portion 2302 is properly positioned around a neck of a subject, the socket 2304 may indicate proper positioning for the device and may engage with the device for proper positioning of the device on the subject.

An example method of non-invasively detecting and monitoring medical or health conditions in human subjects using multiple modalities of sensing is described below with reference to FIG. 24, as well as FIGS. 1-3. At block 2402, the system 102 (see FIGS. 1-3), configured with a suitably shaped device (such as device 304, device 400, device 500, device 600, and/or device 700), is positioned on the human subject 104 such that it contacts suitable parts or areas of the body via at least the plurality of surface electrodes/sensors 114a-114d, where the suitable parts or areas of the body correspond to positioning of the devices, systems, and/or surface sensors (such as the electrodes) described throughout this disclosure. At block 2404, once the system 102 is positioned in contact with the suitable parts or areas of the body, the plurality of multi-modality sensing and measurement modules 112 are activated to obtain multi-modality sensing data from the human subject 104, including, but not limited to, one or more of thoracic impedance sensing data, ECG sensing data, breath rate and tidal volume sensing data, heart rate variability/heart sounds-based sensing data, and pulse oximetry sensing data. At block 2406, the multi-modality sensing data are provided to the data analyzer 226 for at least partial data analysis, data trending, and/or data reduction. At block 2408, the analyzed multi-modality sensing data are provided to the data fusion/decision engine 228, which effectively at least partially fuses or combines the multi-modality sensing data for subsequent use in making one or more inferences about the medical or health status of the human subject 104. At block 2410, the combined multi-modality sensing data are provided to the transmitter/receiver 204, which transmits the at least partially combined multi-modality sensing data over the wireless communication paths 122 to the cloud 110 for possible further data analysis, trending, reduction, and/or fusion. The partially combined multi-modality sensing data can also be transmitted over the wireless communication paths 122 to the cloud 110 for remote downloading by hospital clinicians for monitoring and/or tracking purposes.

FIG. 25 is a diagram illustrating a device 2500 for detecting and monitoring health conditions of a subject, according to some embodiments of the disclosure. In particular, the device 2500 non-invasively detects and monitors COPD conditions in human subjects. The device 2500 is an elongated rectangular element 2512 and includes first electrode 2502a, second electrode 2502b, and third electrode 2502c. The elongated rectangular element 2512 may comprise a frame of the device 2500. The first electrode 2502a is positioned at a first end of the elongated rectangular element 2512, the second electrode 2502b is positioned approximately in the center of the elongated rectangular element 2512, and the third electrode 2502c is positioned at a second end of the elongated rectangular element 2512. In use, the device 2500 is positioned on the torso of a subject with the electrodes 2502a-2502c positioned in contact with the subject's skin. As described above with respect to the system 102 of FIG. 1, data from the electrodes 2502a-2502c are connected to a plurality of multi-modality sensing and measurement modules (such as the modules 112 shown in FIG. 2), which can be activated to gather, collect, sense, measure, or otherwise obtain multi-modality sensing data from the subject.

To detect and/or monitor for COPD, the heart sounds sensor is positioned higher on the torso for better detection of lung sounds. Measurements for COPD include impedance for determining respiration rate, ECG if desired, impedance for determining tidal volume, lung sounds (for detection of abnormal lung rails), and impedance for measuring the shape of the lung volume changes. In particular, the change in the shape of the impedance variations indicates the lung/airway resistance, which can be used to determine the presence of COPD.

Figure 26A:
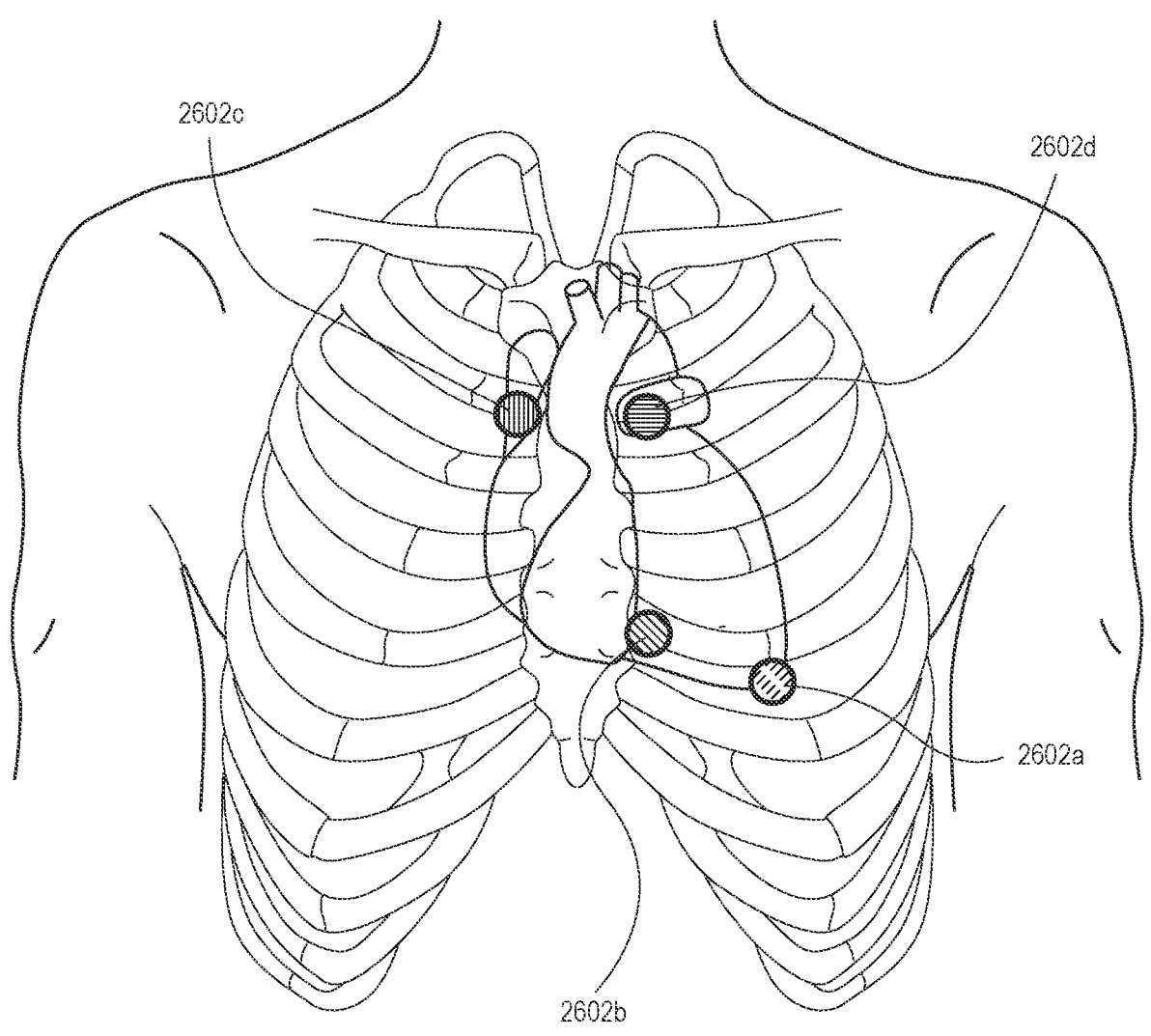
FIGS. 26A-26G are diagrams illustrating various examples of electrode and sensor torso placements for detecting and monitoring health conditions of a subject, according to some embodiments of the disclosure.

FIGS. 26A-26G are diagrams illustrating various examples of electrode and sensor torso placements for detecting and monitoring health conditions of a subject, according to some embodiments of the disclosure. In FIG. 26A, four elements 2602a-2602d are positioned on the torso of the subject, generally over the subject's heart. One element 2602a is positioned at the apex of the heart, in the fifth intercostal space. According to some examples, the placement of 2602a at the apex of the heart in the fifth intercostal space is generally optimal for detection of S3 and S4 heart sounds.

Figure 26B:
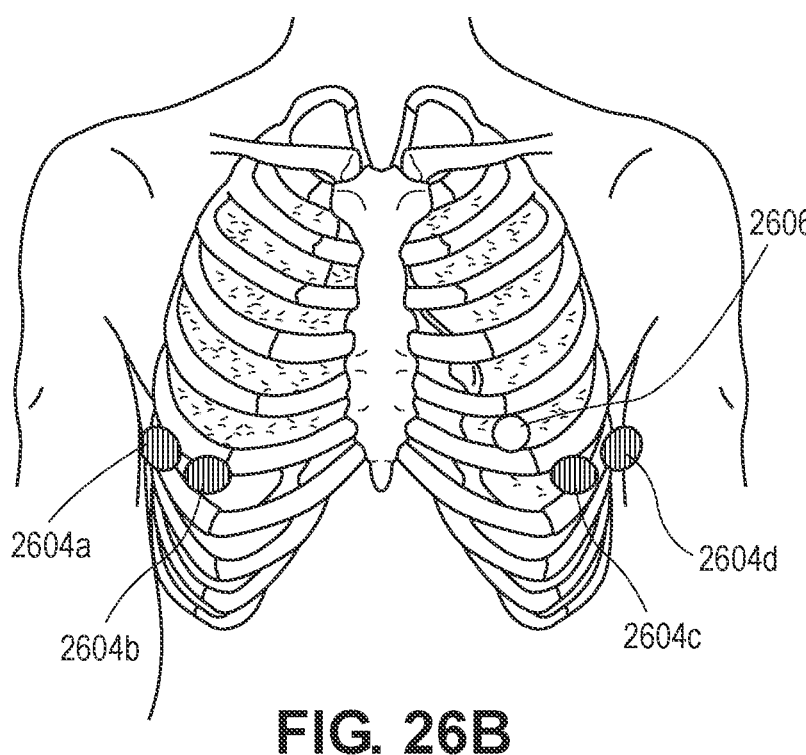

In FIG. 26B, elements 2604a-2604d are positioned across both sides of the torso, and are positioned to measure the impedance across both lungs. The element 2606 is a microphone for detecting heart sounds. A device including elements 2604a-2604d extends across the width of the torso. In some implementations it may be secured in place with a strap around the torso. The elements 2604a-2604d can also be used to measure an ECG.

Figure 26C:
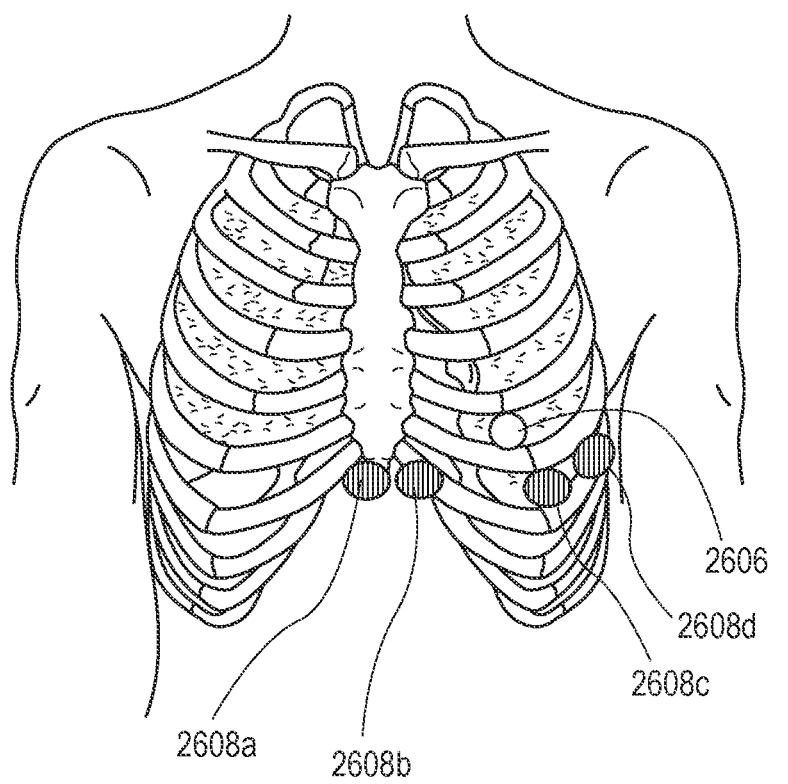

In FIG. 26C, elements 2608a-2608d are positioned on one side of the torso and measure the impedance across one lung. The element 2606 is a microphone for detecting heart sounds. A device including elements 2608a-2608d extends across one side of the torso. In one example, a device such as the device 400 in FIG. 4A can include elements 2608a-2608d and 2606. The elements 2608a-2608d can also be used to measure an ECG.

Figure 26D:
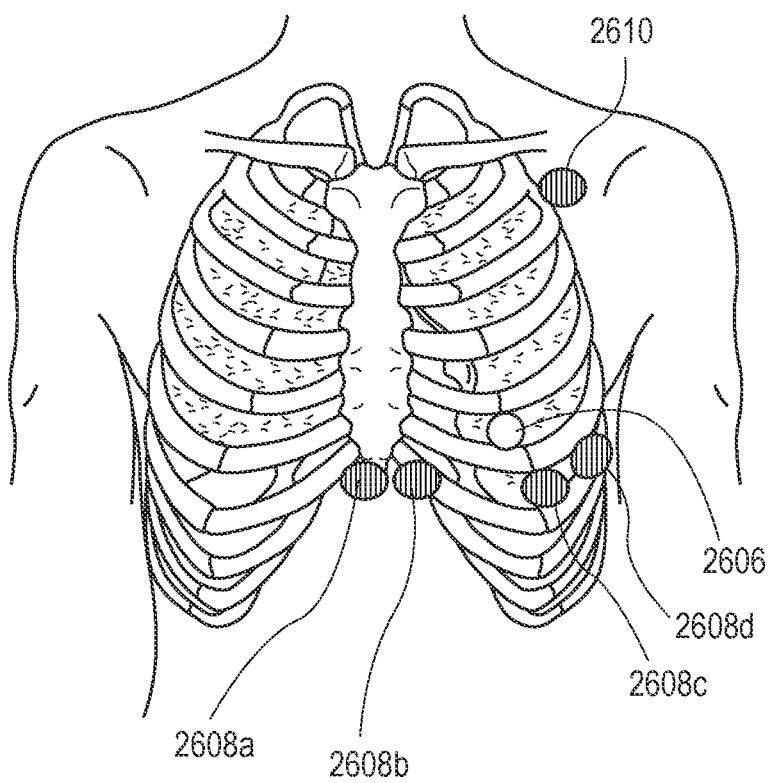

FIG. 26D shows the elements 2608a-2608d and 2606 of FIG. 26C, and an additional element 2610. The element 2610 can be used with any of the elements 2608a-2608d to measure an ECG.

Figure 26E:
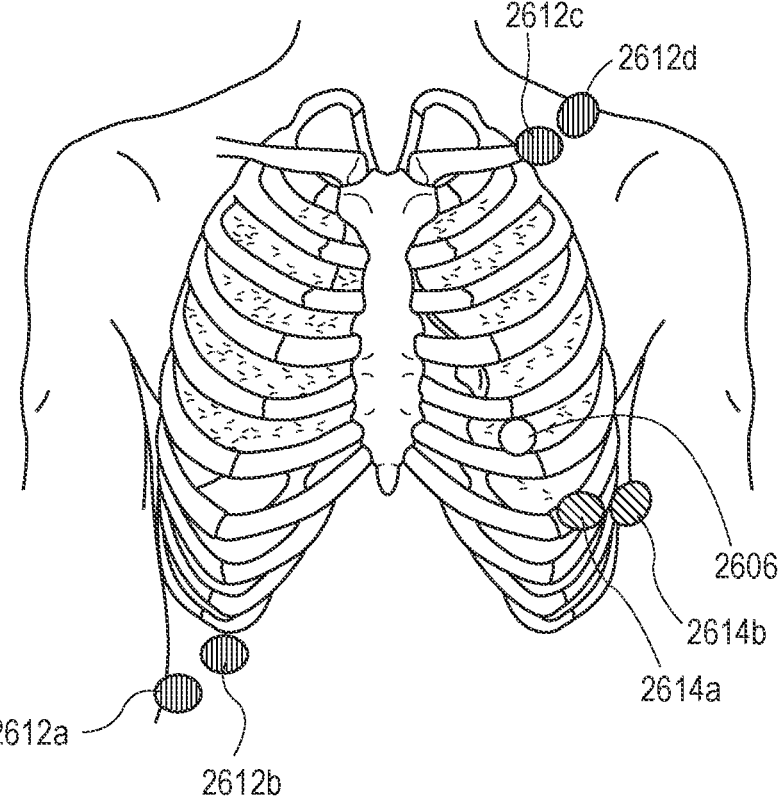

FIG. 26E shows elements 2612a-2612d, 2614a-2614b, and 2606. Elements 2612a-2612d and 2614a-2614b can be used to measure impedance and to measure an ECG. The configuration of elements 2612a-2612d, 2614a-2614b and 2606 can be implemented in a device such as a vest or a shirt.

Figure 26F:
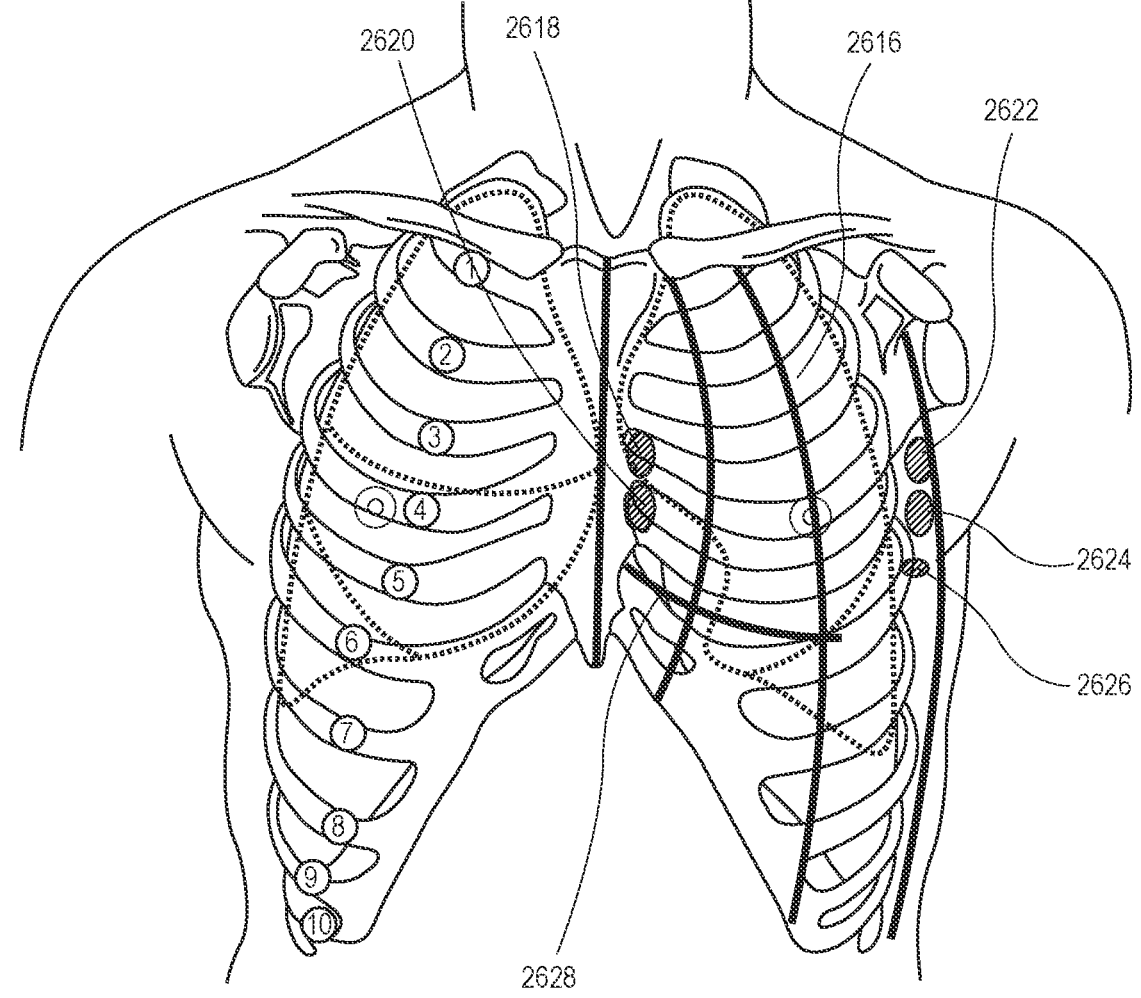

FIG. 26F illustrates another example for placement of electrodes and sensors on a subject. In particular, FIG. 26F illustrates a diagram of a portion of a body of a subject, including a lung 2616 of the subject.

In the example, a first electrode placement 2618 and a second electrode placement 2620 may be located on, or toward, a first side of the lung 2616, and a third electrode placement 2622, a fourth electrode placement 2624, and a fifth electrode placement 2626 may be located on, or toward, a second side of the lung 2616. In some embodiments, the third electrode 1002c (FIG. 10) may be positioned at the first electrode placement 2618 and the fourth electrode 1002d (FIG. 10) may be positioned at the second electrode placement 2620 on the first side of the lung 2616. The first electrode 1002a (FIG. 10) may be positioned at the third electrode placement 2622, the second electrode 1002b (FIG. 10) may be positioned at the fourth electrode placement 2624, and the reference electrode 1002e (FIG. 10) may be positioned at the fifth electrode placement 2626.

Further, a range of sound sensor placements 2628 is illustrated in FIG. 26F. In particular, a sound sensor (such as the sound sensor 1004 (FIG. 10)) may be placed anywhere along the line of the sound sensor placements 2628. The sound sensor placements 2628 may be located toward a lower portion of the lung 2616 and close to a heart of the subject. In some embodiments, the sound sensor placement 2628 may extend from a midline of the subject and 10 cm toward a side from the midline of the subject.

Figure 26G:
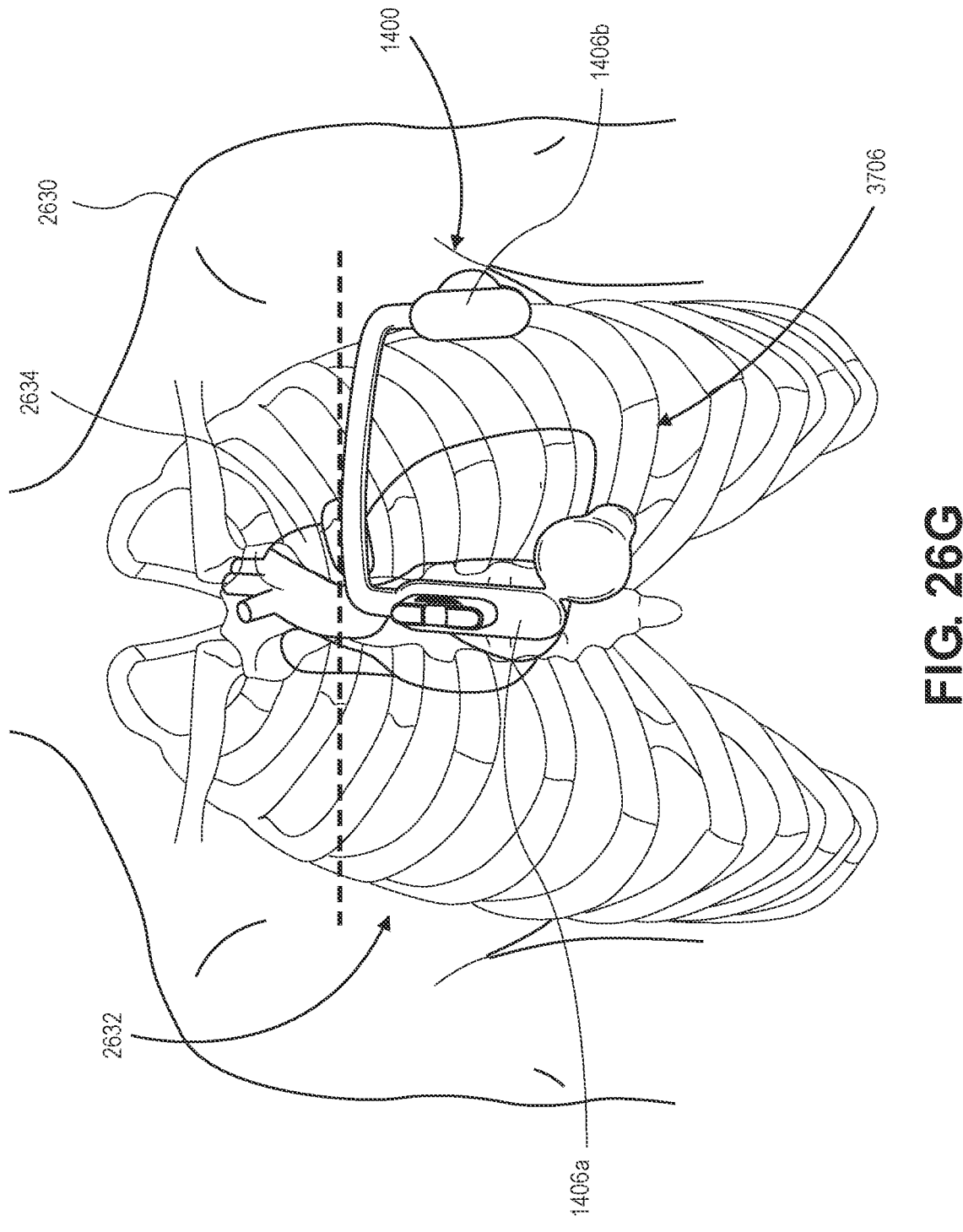

FIG. 26G illustrates another example for placement of electrodes and sensors on a subject. In particular, FIG. 26G illustrates the device 1400 of FIG. 14 positioned on a body 2630 of a subject. The device 1400 is positioned on a chest 2632 of the subject in the illustrated embodiment.

The first extension 1406a of the device 1400 is positioned over a heart 2634 of the subject and at a first side of ribs 3706 of the subject. Accordingly, the electrodes and/or the sensors located on the first extension 1406a (such as the combination sensor 1508 (FIG. 15), the third electrode 1502c (FIG. 15), the fourth electrode 1502d (FIG. 15), and/or the sound sensor 1504 (FIG. 15)) are located at the first side of the ribs 3706. The device 1400 extends across the ribs 3706 of the subject, where the second extension 1406b of the device 1400 is positioned at a second side of the ribs 3706, the second side of the ribs 3706 being opposite to the first side of the ribs 3706. Accordingly, the electrodes and/or the sensors located on the second extension 1406b (such as the first electrode 1502a (FIG. 15) and/or the second electrode 1502b (FIG. 15)) are located at the second side of the ribs 3706.

Figure 27:
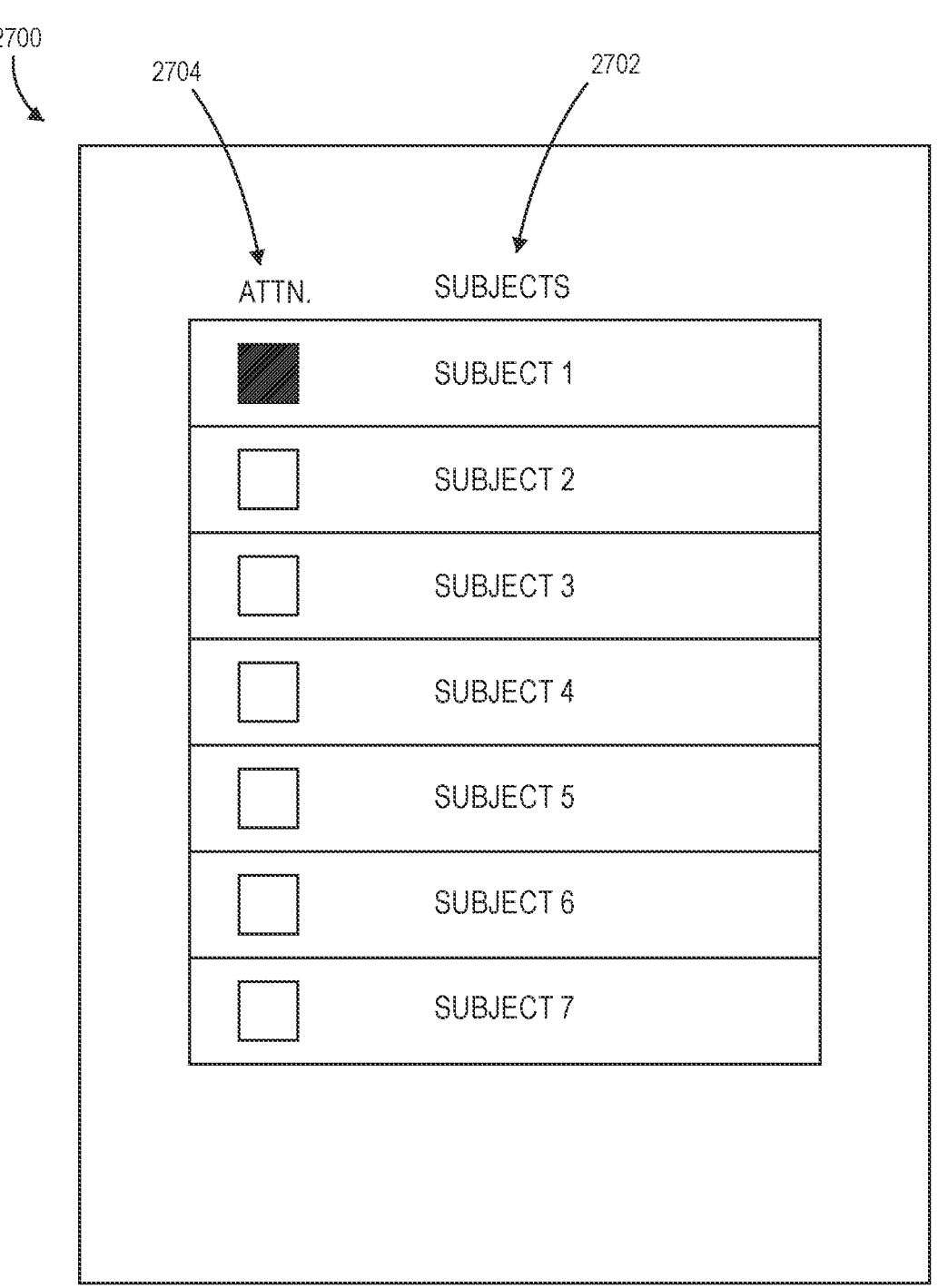
FIG. 27 illustrates an example user interface, according to some embodiments of the disclosure.

FIG. 27 illustrates an example user interface 2700, according to some embodiments of the disclosure. The user interface 2700 may be displayed on a computer device, such as the smartphone 106 (FIG. 1). In particular, the user interface 2700 may be displayed on a display of the computer device.

The user interface 2700 may include a list of subjects 2702. The list of subjects 2702 may include one or more subjects that have utilized systems or devices disclosed herein, such as the system 102 (FIG. 1), the system 1100 (FIG. 11) or the device 304 (FIG. 3), the device 400 (FIG. 4A), the device 500 (FIG. 5), the device 600 (FIG. 6), the device 700 (FIG. 7), the device 1000 (FIG. 10), the device 1400 (FIG. 14), and/or the device 1902 (FIG. 19). In the illustrated embodiment, the list of subjects 2702 includes subjects 1 through 7. Although the subjects are labeled generically in FIG. 27, it is to be understood that the subjects may be labeled via identifiers of each of the subjects in embodiments, where the identifiers can include names of the subjects and/or characters associated with each of the subjects.

The user interface 2700 may further include attention indicators 2704, where each subject within the list of subjects 2702 may have a corresponding attention indicator of the attention indicators 2704. The attention indicators 2704 may indicate whether measurements captured by the systems or devices disclosed herein indicate that the corresponding subject requires attention or review by a user of the user interface. In particular, the attention indicators 2704 can indicate that the subject is having a medical emergency, had measurements taken by the systems or devices that are in within a range of concern for medical reasons, or some combination thereof. In the illustrated embodiment, the attention indicators 2704 includes a plurality of checkboxes, where the checkboxes may be filled to indicate that the data of the corresponding subject requires attention or review by a user and may be left empty to indicate that attention or review is not required for the corresponding subject. In some embodiments, the subjects in the list of subjects 2702 can be ordered based on whether the corresponding attention indicators 2704 indicate that attention or review is required. In other embodiments, the user interface 2700 may further include indications of when the last reading was performed for each of the subjects in the list of subjects 2702, whether each of the subjects in the list of subjects 2702 have completed scheduled measurements, a trend of the measurements for each of the subjects in the list of subjects 2702, a trend of vitals for each of the subjects in the list of subjects 2702, or some combination thereof. Further, the user interface 2700 may include indications of a number of subjects that have been indicated for monitoring by the user, a number of high-risk subjects, a number of actions pending, a number of new readings, or some combination. In response to a user interacting with the subjects listed in the list of subjects, any of the attention indicators, or any of the other indications, another user interface may be displayed that includes the corresponding information. For example, in response to the user interacting (such as clicking a mouse, or placing a finger on an associated area on a touch screen) with a subject, a user interface displaying data for the subject may be displayed.

Figure 28:
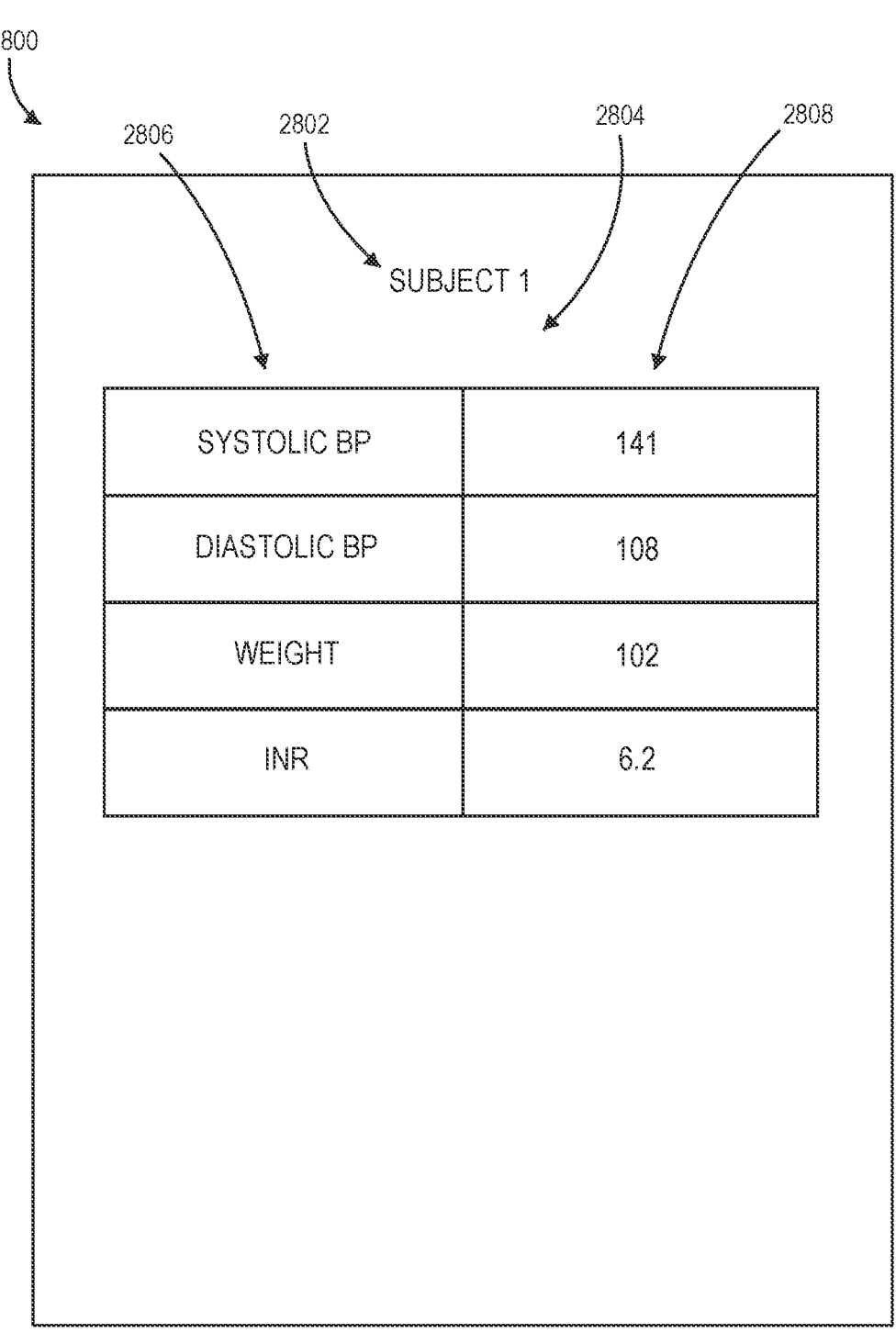
FIG. 28 illustrates another example user interface, according to some embodiments of the disclosure.

FIG. 28 illustrates another example user interface 2800, according to some embodiments of the disclosure. In particular, the user interface 2800 may display information of a subject. The user interface 2800 may be displayed in response to a user interacting with one of the subjects in the list of subjects 2702 (FIG. 27) on the user interface 2700 (FIG. 27). The user interface 2800 may be displayed on a computer device, such as the smartphone 106 (FIG. 1). In particular, the user interface 2800 may be displayed on a display of the computer device.

The user interface 2800 may include a subject indication 2802 that indicates a subject for which data is being displayed. The user interface 2800 may further display data 2804 for the subject. The data 2804 may include characteristics 2806 of the subject and values 2808 corresponding to the characteristics 2806. In the illustrated embodiment, the characteristics 2806 include a systolic blood pressure, a diastolic blood pressure, a weight, and an international normalized ratio (INR) of the subject. In other embodiments, the characteristics 2806 may include other characteristics of the subject that can be derived from the captured data.

Figure 29:
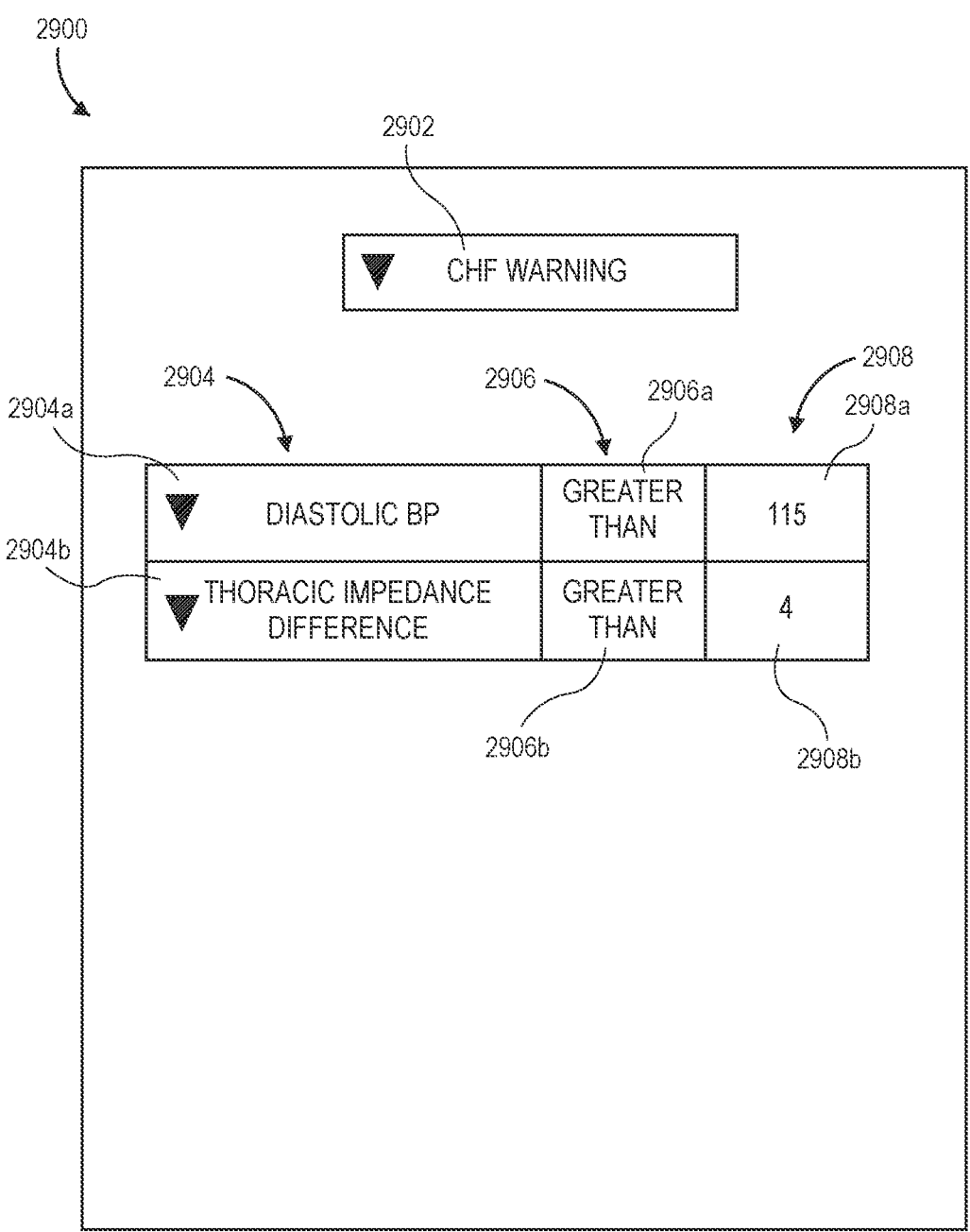
FIG. 29 illustrates another example user interface, according to some embodiments of the disclosure.

FIG. 29 illustrates another example user interface 2900, according to some embodiments of the disclosure. The user interface 2900 may be displayed on a computer device, such as the smartphone 106 (FIG. 1). The user interface 2900 may display a number of fields that allow a user to select a display action and define characteristics indicating when the display action is to be performed. The display action may include displaying an indication on a display of the computer device, displaying data on the display of the computer device, displaying an indication on a base station (such as the base station 1204 (FIG. 12), the base station 1300 (FIG. 13), and/or the base station 1900 (FIG. 19)) related to the display action, displaying an indication on a device (such as the system 102 (FIG. 1), the device 304 (FIG. 3), the device 400 (FIG. 4A), the device 500 (FIG. 5), the device 600 (FIG. 6), the device 700 (FIG. 7), the device 1000 (FIG. 10), the device 1102 (FIG. 11), the device 1400 (FIG. 14), the device 1902 (FIG. 19), and/or the device 2500 (FIG. 25)) related to the display action, or some combination thereof. The indication may include displaying a light, emitting a sound, producing a physical force, displaying a message, or some combination thereof.

The user interface 2900 may include a display action field 2902. The display action field 2902 allows a user to select a display action to be performed. In the illustrated embodiment, the display action selected in the display action field 2902 is a CHF warning. The display action field 2902 may comprise a drop-down menu or list where the drop-down menu or list displays one or more display actions that can be selected. In some embodiments, the display action field 2902 may allow the user to generate a display action and define the actions to be performed in response to the display action being triggered, and/or to edit the actions to be performed in response to a display action being triggered that was previously defined.

The user interface 2900 may further include one or more characteristics fields 2904. For example, the user interface 2900 includes a first characteristic field 2904a for a diastolic blood pressure and a second characteristic field 2904b for a thoracic impedance difference in the illustrated embodiment. The characteristic fields 2904 allows the user to select characteristics utilized to determine when the display action is to be triggered. In some embodiments, each of the characteristic fields 2904 may comprise a drop-down menu or list that displays one or more characteristics that can be utilized for determining when a display action is to be triggered. The characteristics included in the drop-down menu or list may include any characteristics associated with the data captured by a device (such as the system 102 (FIG. 1), the device 304 (FIG. 3), the device 400 (FIG. 4A), the device 500 (FIG. 5), the device 600 (FIG. 6), the device 700 (FIG. 7), the device 1000 (FIG. 10), the device 1102 (FIG. 11), the device 1400 (FIG. 14), the device 1902 (FIG. 19), and/or the device 2500 (FIG. 25)), any characteristics that can be derived from the data captured by the device, or information (such as age, weight, and/or medical history) associated with a subject that may utilize the device. In some embodiments, one or more of the display actions may have corresponding characteristics, where the corresponding characteristics are displayed in the characteristic fields 2904 when the display action is selected in the display action field 2902. Further, user interface 2900 may allow the user to add or remove characteristic fields 2904 in some embodiments, where one or more characteristic fields 2904 may be included on the user interface 2900 as the user adds or removes characteristic fields 2904. In some embodiments, the user interface 2900 may allow the user to define new characteristic fields, as well as measurements and/or inputs that are used for determining the values corresponding to the characteristic fields.

The user interface 2900 may further include one or more relational fields 2906. Each characteristic field of the characteristic fields 2904 may have a corresponding relational field of the relational fields 2906. For example, a first relational field 2906a corresponds to the first characteristic field 2904a and a second relational field 2906b corresponds to the second characteristic field 2904b in the illustrated embodiment. The relational fields 2906 allow a user to define a relationship between a measured or calculated value for a characteristic with a threshold value for the characteristic. For example, the relational fields 2906 may include entries of greater than, less than, equal to, between, and/or outside of, where the entries are utilized for determining when a display action should be triggered when comparing the measured or calculated value with the threshold value. For one example, when the entry of a relational field is selected to be greater than, the display action may be triggered when the measured or calculated value is greater than the threshold value. Further, the entry of between may indicate that the display action may be triggered when the measured or calculated value is between a first threshold value and a second threshold value, and the entry of outside of may indicate that the display action may be triggered when the measured or calculated value is outside of a range defined by a first threshold value and a second threshold value.

The user interface 2900 may further include one or more threshold value fields 2908. Each characteristic field of the characteristic fields 2904 may have one or more corresponding threshold value fields of the threshold value fields 2908. For example, a first threshold value field 2908a corresponds to the first characteristic field 2904a and a second threshold value field 2908b corresponds to the second characteristic field 2904b in the illustrated embodiment. The threshold value fields 2908 allow a user to define threshold values for the characteristics of the corresponding characteristic fields 2904. Further, each relational field 2906 may have one or more corresponding threshold value fields of the threshold value fields 2908. For example, the first threshold value field 2908a corresponds to the first relational field 2906a and the second threshold value field 2908b corresponds to the second relational field 2906b.

Entries of the characteristic fields 2904, the corresponding relational fields 2906, and the corresponding threshold value fields 2908 may define when the corresponding display action should be performed. For example, each characteristic field of the characteristic fields 2904 may be utilized to define a characteristic for which a measured or calculated value should be obtained for determining whether the corresponding display action is to be performed. The relational field of the relational fields 2906 and the threshold value field or threshold value fields of the threshold value fields 2908 that corresponds to a characteristic field may be utilized to define an equation for the characteristic of the characteristic field, where the equation indicates that the display action may be performed when the measured or calculated value satisfies the equation. For example, the entry of the first characteristic field 2904a in the illustrated embodiment indicates that a measured or calculated value for diastolic blood pressure is to be obtained for the CHF warning display action, as selected in the display action field 2902. The first relational field 2906a and the first threshold value field 2908a define the equation of x greater than 115 in the illustrated embodiment, where x is measured or calculated value. Therefore, if the measured or calculated value for the diastolic blood pressure is greater than 115 (thereby satisfying the equation), it indicates that the display action should be performed.

In some embodiments, the display action may be performed in response to all of the defined equations for the characteristics being satisfied. In other embodiments, the display action may be performed in response to a portion of the defined equations for the characteristics being satisfied. The user may define which equations are to be satisfied, or which combination of equations are to be satisfied, to trigger performance of the display action in some embodiments. For example, the user may define that all of the equations are to be satisfied for the performance to be triggered, that a first portion of the equations and a second portion of the equations are to be satisfied for the performance to be triggered, that a first portion of the equations or a second portion of the equations are to be satisfied for the performance to be triggered, or some combination thereof. In some embodiments, the user interface 2900 may include one or more fields that allow the user to define which equations are included in each of the portions and the operand (for example, the "and" operand and the "or" operand) defining the relationship between the portions to trigger the performance of the display action.

Having described the above illustrative embodiments of systems, apparatus, and methods of non-invasively detecting and monitoring medical or health conditions such as chronic conditions, including CHF, in human subjects using multiple modalities of sensing, other alternative embodiments and/or variations can be made and/or practiced. For example, it was described herein that the thoracic impedance measurement module 212, the ECG measurement module 214, the breath rate and tidal volume measurement modules 216, 218, the heart sounds-based measurement module 220, and the pulse oximetry measurement module 222 can provide corresponding multi-modality sensing data to the data analyzer 226 for subsequent data analysis, data trending, and/or data reduction. In an alternative embodiment, one or more of the plurality of multi-modality sensing and measurement modules 112 can further obtain multi-modality sensing data pertaining to non-invasive, pressure wave velocity (PWV)-based systolic and/or diastolic blood pressures between the human subject's chest and finger, for example, and/or cardiac output data based on the direct measurement of at least the cardiac contractility, and provide these additional modalities of sensing data to the data analyzer 226 for further data analysis, data trending, and/or data reduction.

Figure 30A:
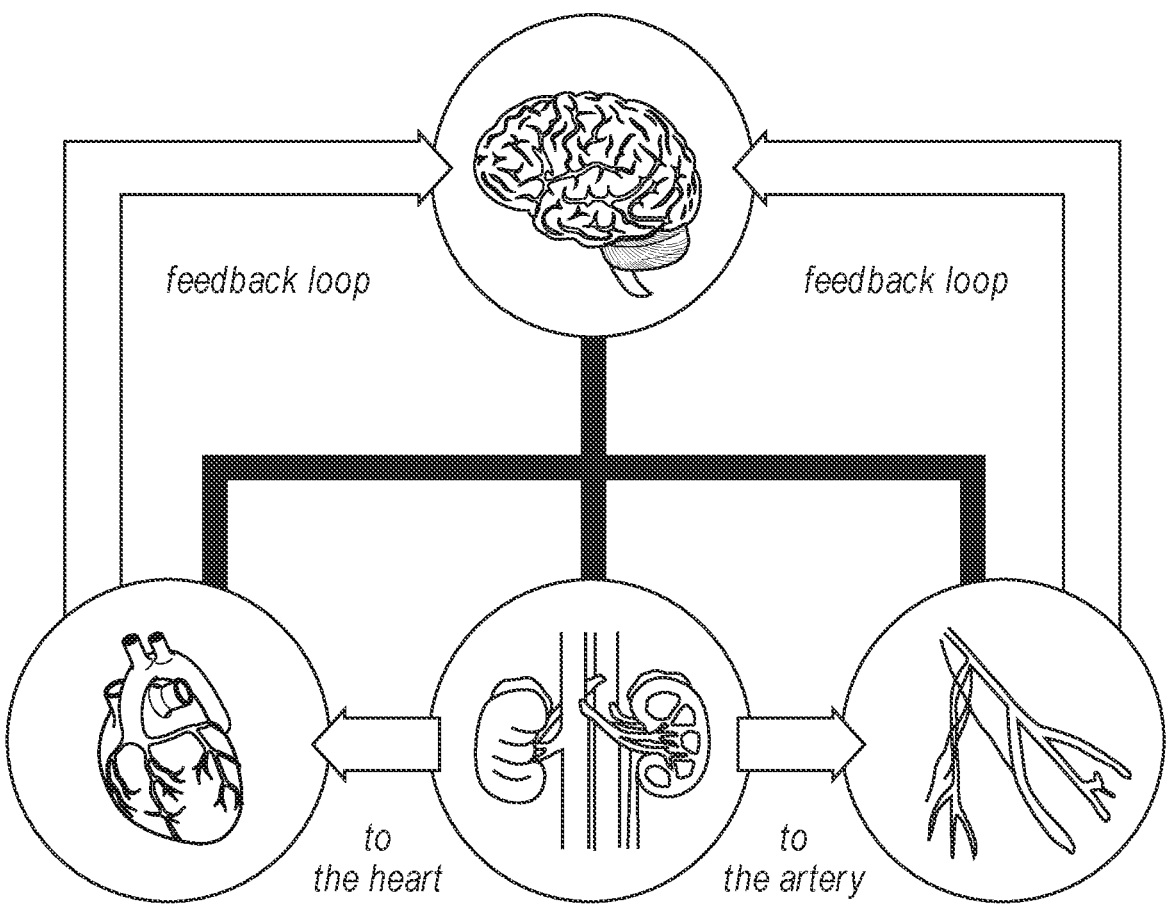
FIGS. 30A and 30B are diagrams illustrating an example cardiovascular feedback loop.
Figure 30B:
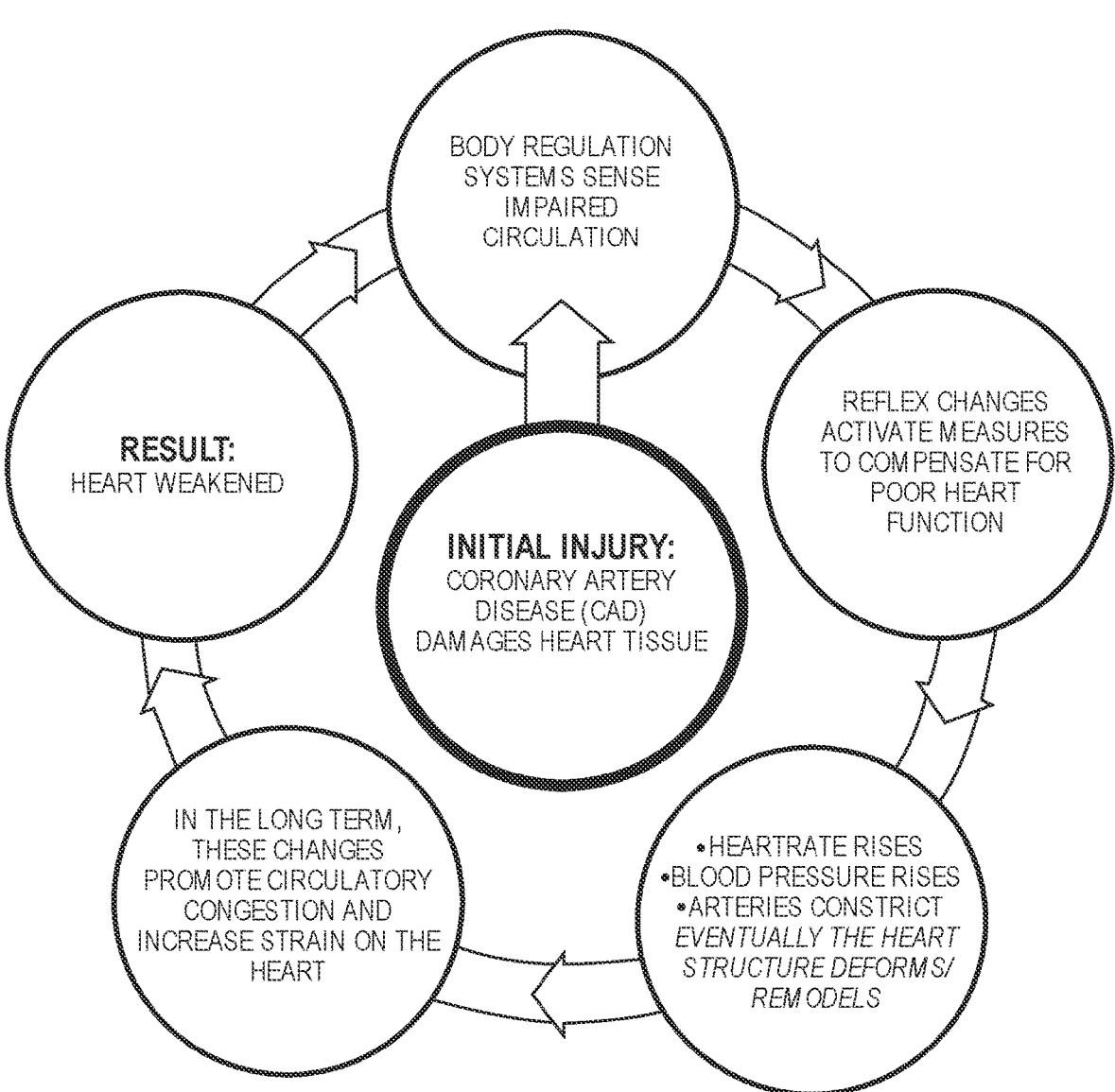

Cardiovascular Feedback Loop (See FIGS. 30A and 30B)

The nervous system receives a signal that blood pressure is falling. To ensure survival, the brain sends signals to the heart, kidneys, and arteries, each playing a role in diverting blood flow to major organs and maintaining blood pressure. In response to the signals from the brain, the heart beats faster and more forcefully. This increases the circulating blood pressure to the body. It then sends feedback to the brain, informing that changes have been made, and to halt the nervous system's intervention. The signals from the brain stimulate the adrenal glands (a member of the endocrine system located on top of each kidney) to secrete epinephrine (generally known as adrenaline) and norepinephrine into the bloodstream. Upon reaching target organs, it alters their activity. The arteries, in response to the signals from the brain, assist the blood pressure in the body by changing arterial resistance to flow. Changes in vascular tone shift blood away from muscles to internal organs, as their health most directly effects survival. Arteries send feedback to the brain, informing it of the changes.

Figure 31:
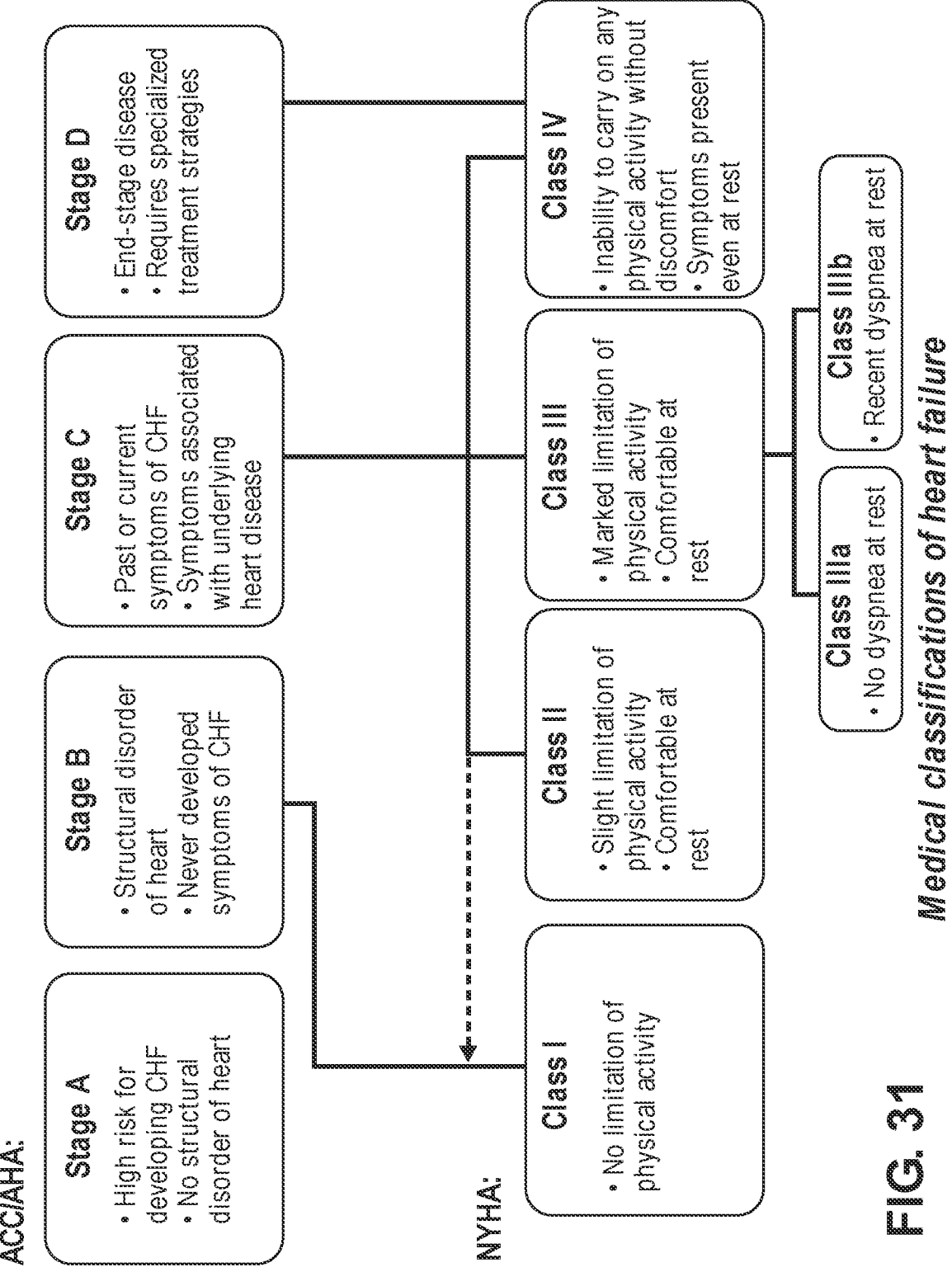
FIG. 31 is a diagram illustrating the medical classifications of heart failure.

What is "Heart Failure?" (See FIG. 31)

The 2013 ACCF/AHA Heart Failure Guidelines defined heart failure as "a complex clinical syndrome that results from any structural or functional impairment of ventricular filling or ejection of blood." Heart pump impairment resulting in symptoms:

Heart: It is necessary that any occurrence of clinical heart failure must include a primary or secondary involvement of the heart. If this is not evident, we either have not looked hard enough or it is not heart failure.

Pump: A complete description of the heart includes multiple functions including electrical, hormonal, and structural components. For heart failure to be present, however, there must be a manifest effect on the ability of the heart to move blood in the circulation.

Impairment: Impairment implies a degree of insufficiency that, in general, does not require complete replacement therapy. It may only be unmasked by activity or stress. If given a letter grade, a patient's heart function would rate a C+ rather than an F. Nevertheless, some degree of decreased function must be present for an individual to have heart failure.

Resulting in: An initial insult to the heart may result in an immediate profound or a subtle progression to heart pump impairment only overtime. Neurohormonal mechanisms may be activated and contribute to this syndrome. This may include adverse structural and biochemical remodeling. Any process affecting the heart must be causally related to an individual's status to result in heart failure.

Stages: The ACC/AHA classification of heart failure defines 4 stages of heart failure beginning with (1) risk factors for heart failure, (2) asymptomatic heart impairment, (3) symptomatic heart failure, and (4) advanced heart failure.

The following recites some examples of subject matter disclosed herein. It is to be understood that the examples are not to limit this scope of the disclosure and the scope of the disclosure includes everything described herein.

Example 1 may include a device for non-invasively detecting and monitoring medical conditions using multiple modalities of sensing, comprising at least two electrodes configured to be positioned on a subject, an acoustic sensor configured to be positioned on a subject, a thoracic impedance measurement module connected to the at least two electrodes, for measuring a first impedance between the at least two electrodes, and a heart acoustic measurement module connected to the acoustic sensor, for detecting and measuring a heart sound from the acoustic sensor.

Example 2 may include the device of example 1 or some other example herein, further comprising a sensor for determining an orientation of the device.

Example 3 may include the device of example 2 or some other example herein, wherein the thoracic impedance measurement module measures the first impedance when the device is in a first orientation, and measures a second impedance between the at least two electrodes when the device is in a second orientation.

Example 4 may include the device of example 3 or some other example herein, wherein the first orientation indicates that the device is approximately horizontal, and wherein the second orientation indicates that the device is at an angle with respect to a horizontal plane.

Example 5 may include the device of example 1 or some other example herein, wherein the thoracic impedance measurement module automatically measures the first impedance at regular intervals.

Example 6 may include the device of example 1 or some other example herein, further comprising an electrocardiogram measurement module, connected to the at least two electrodes, for measuring electrical activity between the at least two electrodes.

Example 7 may include the device of example 1 or some other example herein, wherein the acoustic sensor is one of an ultrasound sensor and a piezo-electric microphone.

Example 8 may include the device of example 1 or some other example herein, wherein the at least two electrodes comprise at least two electrode pairs, each electrode pair including a force electrode configured to apply current to the subject and a sense electrode configured to sense changes caused by the applied current.

Example 9 may include the device of example 1 or some other example herein, wherein the heart sound is an S3 heart sound.

Example 10 may include a system for non-invasively detecting and monitoring medical conditions using multiple modalities of sensing, comprising a device positioned on a subject having a plurality of surface sensors and a plurality of sensing modules connected to the plurality of surface sensors, configured to gather multi-modality sensing data, wherein the multi-modality sensing data includes a first impedance between at least two of the surface sensors, and heart sounds from at least one of the plurality of surface sensors, and a data analyzer operative to perform at least one of data analysis, data trending, and data reduction of the multi-modality sensing data.

Example 11 may include the system of example 10 or some other example herein, further comprising a data decision engine configured to combine at least some of the multi-modality sensing data, wherein the combined multi-modality sensing data indicates a medical condition status of the subject.

Example 12 may include the system of example 11 or some other example herein, further comprising a transceiver configured to transmit the combined multi-modality sensing data over at least one wireless communication path to a cloud for further processing.

Example 13 may include the system of example 10 or some other example herein, wherein the device further comprises a sensor for determining an orientation of the device.

Example 14 may include the system of example 13 or some other example herein, wherein the device includes a thoracic impedance measurement module configured to measure the first impedance when the device is in a first orientation and a second impedance between the at least two of the surface sensors when the device is in a second orientation.

Example 15 may include the system of example 10 or some other example herein, wherein the device further comprises an electrocardiogram measurement module, connected to the plurality of surface sensors, for measuring electrical activity between at least two of the surface sensors.

Example 16 may include the system of example 10 or some other example herein, wherein the surface sensors include at least one of electrodes, heart sounds sensors, ultrasound sensors, and photoplethysmography sensors.

Example 17 may include a method for non-invasively detecting and monitoring medical conditions using multiple modalities of sensing, comprising transmitting a current transcutaneously from a first electrode positioned on a subject, receiving a current transcutaneously at a second electrode positioned on the subject, measuring a voltage between the first and second electrodes, determining a thoracic impedance at least based on the voltage, receiving an acoustic signal from an acoustic sensor, measuring a heart sound from the acoustic sensor, and transmitting thoracic impedance data and heart sound measurements to a data analyzer configured to perform at least one of data analysis, data trending, and data reduction of the thoracic impedance data and heart sound measurements.

Example 18 may include the method of example 17 or some other example herein, further comprising determining an orientation of the device.

Example 19 may include the method of example 18 or some other example herein, wherein the thoracic impedance is determined when the device is in a first orientation and further comprising determining a second impedance measurement between the first and second electrodes when the device is in a second orientation.

Example 20 may include the method of example 17 or some other example herein, further comprising measuring electrical activity between the first and second electrodes and producing an electrocardiogram.

Example 21 may include a device for capturing measurements related to health of a subject, comprising a frame to be worn on a skin of the subject, the frame having a main body, a first extension coupled at a first end of the main body, and a second extension coupled at a second end of the main body, a first electrode mounted to the first extension, the first electrode to apply an electrical potential to the subject, a second electrode mounted to the second extension, the second electrode to detect a disturbance caused by the electrical potential being applied, and a sound sensor mounted to the first extension or the second extension, the sound sensor to detect heart sounds of the subject.

Example 22 may include the device of example 21, further comprising a control module mounted to the frame and coupled to the second electrode and the sound sensor, the control module to receive first data related to the disturbance from the second electrode, receive second data related to the heart sounds from the sound sensor, and fuse the first data and the second data into combined data.

Example 23 may include the device of example 22, wherein the control module is further coupled to the first electrode, the control module to cause the first electrode to apply the electrical potential.

Example 24 may include the device of example 22, wherein the control module includes one or more indicators, and wherein the control module causes the one or more indicators to provide an indication of a status of the device.

Example 25 may include the device of example 21, wherein the electrical potential is a first electrical potential and the disturbance is a first disturbance, and wherein the device further comprises a third electrode mounted to the first extension, the third electrode to apply a second electrical potential to the subject, and a fourth electrode mounted to the second extension, the fourth electrode to detect a second disturbance caused by the second electrical potential being applied.

Example 26 may include the device of example 21, further comprising a reference electrode mounted to the frame, the reference electrode to detect a potential of a body of the subject.

Example 27 may include the device of example 26, further comprising a control module mounted to the frame and coupled to the second electrode and the reference electrode, the control module to receive first data related to the disturbance from the second electrode and second data related to the potential of the body from the reference electrode, wherein the control module is to utilize the second data to facilitate processing of the first data.

Example 28 may include the device of example 21, further comprising a temperature sensor mounted to the frame, the temperature sensor to detect a temperature of the subject.

Example 29 may include the device of example 21, further comprising a combination sensor mounted to the frame, the combination sensor having a reference electrode for detecting a potential of a body of the subject and a temperature sensor for detecting a temperature of the subject.

Example 30 may include a base station to be coupled to a device for capturing measurements related to health of a subject, the base station comprising a housing, and electronics located within the housing, the electronics to couple to the device and to analyze data received from the device to determine physiologic information for the subject based on the data.

Example 31 may include the base station of example 31, wherein the electronics include a processor, and wherein the processor is to analyze the data and determine the physiologic information.

Example 32 may include the base station of example 31, wherein the electronics include a transmitter/receiver to wirelessly communicate with a computer device and provide the physiologic information to the computer device.

Example 33 may include the base station of example 32, wherein the computer device comprises a smartphone or a cloud.

Example 34 may include the base station of example 30, further comprising an arm coupled to the housing and to retain the device when the device is mounted to the base station.

Example 35 may include the base station of example 34, wherein the arm includes an offset portion that is configured contact the device when the device is mounted to the base station, and wherein the offset portion is to apply a force to the device to retain the device.

Example 36 may include the base station of example 30, further comprising a cover rotatably coupled to the housing, the cover to rotate between a cover position and a stand position, wherein the cover is to extend across the a front side of the housing when in the cover position, and wherein the cover is located on a back side of the housing when in the stand position, and is to contact a surface and at least partially support the base station on the surface when the base station is placed on the surface.

Example 37 may include the base station of example 30, further comprising one or more indicators, wherein the one or more indicators are to indicate a status of the base station.

Example 38 may include a system for capturing measurements related to health of a subject, the system comprising a device including a frame and one or more surface sensors mounted to the frame, and a guide to facilitate positioning of the device on the subject, wherein a portion of the guide indicates proper position of the device on the subject when the guide is worn by the subject.

Example 39 may include the system of example 38, wherein an edge of the device is to indicate a position on the subject for a certain edge of the device to indicate the proper position of the device.

Example 40 may include the system of example 38, wherein the guide includes a neck piece to be worn around a neck of the subject to facilitate positioning of the device, and a positioning piece to be mounted to the neck piece, wherein the positioning piece is to indicate the proper position of the device when the positioning piece is mounted to the neck piece and the neck piece is worn around the neck of the subject.

Example 41 may include the system of example 40, wherein a position that the positioning piece to be mounted to the neck piece is adjustable.

Example 42 may include the system of example 38 wherein the one or more surface sensors include a first electrode, a second electrode, and a sound sensor.

Example 43 may include a guide to be utilized for positioning a device on a subject, the guide comprising a neck piece to be positioned around a neck of the subject, and a positioning piece having an indication portion that indicates a proper position for the device on the subject when the neck piece is position around the neck of the subject.

Example 44 may include the guide of example 43, wherein the neck piece comprises a necklace portion having a circular shape with a hollow center, and wherein the neck of the subject is to be located within the hollow center of the necklace portion when the neck piece is positioned around the neck of the subject.

Example 45 may include the guide of example 44, further comprising a first positioning element coupled to the necklace portion and a second positioning element coupled to the necklace portion, wherein the first positioning element and the second positioning element extend inward from the necklace portion, and wherein the first positioning element and the second positioning element are to contact the neck of the subject to facilitate positioning of the necklace portion when the neck piece is positioned around the neck of the subject.

Example 46 may include the guide of example 45, wherein the first positioning element is coupled to a first side of the necklace portion and the second positioning element is coupled to a second side of the necklace portion, the second side of the necklace portion being opposite to the first side of the necklace portion.

Example 47 may include the guide of example 43, wherein the positioning piece is adjustably coupled to the neck piece.

Example 48 may include the guide of example 47, wherein the neck piece includes a mounting portion, wherein the positioning piece includes a mounting portion, and wherein the mounting portion of the neck piece couples to the mounting portion of the positioning piece to couple the positioning piece to the neck piece.

Example 49 may include the guide of example 43, wherein the indication portion includes an edge of the positioning piece, and wherein indication portion indicates that the device is to be positioned adjacent to the edge for the proper position.

Example 50 may include a system for monitoring medical or health conditions of a subject, the system comprising a device to be worn by the subject, the system comprising a sensor to capture data associated with the subject, a base station to be communicatively coupled to the device, the base station to retrieve the data to the device and process the data to produce processed data, and a computer device to be communicatively coupled to the base station, the computer device to retrieve the processed data from the base station and to display information based on the processed data.

Example 51 may include the system of example 50, wherein the sensor comprises an electrode, a sound sensor, or a temperature sensor, and wherein the data comprises a representation of a current, a voltage, a heart sound, a temperature of the subject.

Example 52 may include the system of example 50, wherein to process the data by the base station includes fusing the data with other data captured by the device and retrieved from the device.

Example 53 may include the system of example 50, wherein the base station includes a housing and an arm, wherein the arm is to maintain the device against the housing when the device is mounted to the base station.

Example 54 may include the system of example 50, wherein the information comprises the processed data.

Example 55 may include the system of example 50, wherein the computer device is to receive selections from a user and generate an equation associated with a display action based on the selections from the user, the equation including the processed data, wherein the display action is to be performed in response to the equation being satisfied.

Example 56 may include the system of example 55, wherein the display action comprises displaying an indication by the base station or the device.

Example 57 may include a device for capturing measurements related to a health of a subject, comprising a frame to be worn on a skin of the subject, the frame having a main body, a first extension coupled at a first end of the main body, and a second extension coupled at a second end of the main body, a first electrode mounted to the first extension, the first electrode to apply an electrical potential to the subject, a second electrode mounted to the second extension, the second electrode to detect a disturbance caused by the electrical potential being applied, and a sound sensor mounted to the first extension or the second extension, the sound sensor to detect heart sounds of the subject.

Example 58 may include the device of example 57, further comprising a control module mounted to the frame and coupled to the second electrode and the sound sensor, the control module to receive first data related to the disturbance from the second electrode, receive second data related to the heart sounds from the sound sensor, and fuse the first data and the second data to produce fused data.

Example 59 may include the device of example 58, wherein the control module is further coupled to the first electrode, the control module to cause the first electrode to apply the electrical potential.

Example 60 may include the device of example 58, wherein the control module includes one or more indicators, and wherein the control module causes the one or more indicators to provide an indication of a status of the device.

Example 61 may include the device of example 57, wherein the electrical potential is a first electrical potential and the disturbance is a first disturbance, and wherein the device further comprises a third electrode mounted to the first extension, the third electrode to apply a second electrical potential to the subject, and a fourth electrode mounted to the second extension, the fourth electrode to detect a second disturbance caused by the second electrical potential being applied.

Example 62 may include the device of example 61, wherein a first vector is formed between the first electrode and the second electrode, wherein a second vector is formed between the third electrode and the fourth electrode, wherein the second vector is located above the first vector when the device is positioned on the skin of the subject.

Example 63 may include the device of example 57, further comprising a reference electrode mounted to the frame, the reference electrode to detect a potential of a body of the subject.

Example 64 may include the device of example 63, further comprising a control module mounted to the frame and coupled to the second electrode and the reference electrode, the control module to receive first data related to the disturbance from the second electrode and second data related to the potential of the body from the reference electrode, and utilize the second data to facilitate processing of the first data.

Example 65 may include the device of example 57, further comprising a temperature sensor mounted to the frame, the temperature sensor to detect a temperature of the subject.

Example 66 may include the device of example 57, further comprising a combination sensor mounted to the frame, the combination sensor having a reference electrode for detecting a potential of a body of the subject and a temperature sensor for detecting a temperature of the subject.

Example 67 may include a system for monitoring a health of a subject, comprising a device for capturing measurements related to the health of the subject, comprising a first electrode coupled to a first extension of the device, the first extension of to be positioned against a skin of the subject on a first side of a lung of the subject, the first electrode to apply an electrical potential to the skin of the subject, a second electrode coupled to a second extension of the device, the second extension at an opposite end of the device from the first extension, the second extension to be positioned against the skin of the subject on a second side of the lung of the subject, the second electrode to detect a disturbance caused by the electrical potential being applied, and a base station to couple to the device, the base station to retrieve data related to the disturbance detected from the device and upload the data to a cloud.

Example 68 may include the system of example 67, wherein the base station includes one or more indicators to indicate retrieval of the data from the device and upload of the data to the cloud.

Example 69 may include the system of example 67, wherein the device further includes a sound sensor coupled to an island of the device, the island coupled to one of the first extension or the second extension, wherein the island is to positioned against the skin of the subject near an apex of a heart of the subject, and wherein the sound sensor is to sense heart sounds of the subject.

Example 70 may include the system of example 69, wherein the base station is further to retrieve the heart sounds sensed by the sound sensor from the device and provide the heart sounds to the cloud for replay.

Example 71 may include the system of example 67, wherein the device further comprises a control module with one or more indicators, the control module coupled to the first electrode and the second electrode, wherein the control module is to capture a first measure of the disturbance detected by the second electrode when the device is positioned against the skin of the subject and at a first orientation, indicate, via the one or more indicators, that the subject is to change a position to have the device at a second orientation when the device is positioned against the skin of the subject, and capture a second measure of the disturbance detected by the second electrode when the device is positioned against the skin of the subject and at the second orientation.

Example 72 may include the system of example 71, wherein the control module includes an accelerometer, and wherein the accelerometer is to determine orientations of the device for determination of the first orientation and the second orientation.

Example 73 may include the system of example 67, wherein a first vector extends between the first electrode and the second electrode, wherein the electrical potential is a first electrical potential, wherein the disturbance is a first disturbance, and wherein the device further comprises a third electrode coupled to the first extension of the device and located closer to a bottom of the device than the first electrode, the third electrode to apply a second electrical potential to the skin of the subject, and a fourth electrode coupled to the second extension of the device and located closer to a bottom of the device than the second electrode, the fourth electrode to detect a second disturbance caused by the second electrical potential being applied, wherein a second vector extends between the third electrode and the fourth electrode, the second vector being separate from the first vector.

Example 74 may include a device for capturing measurements related to a health of a subject, comprising one or more sensors to be positioned on the subject, and one or more measurement modules coupled to the one or more sensors, the one or more measurement modules to cause a first portion of the one or more sensors to detect a thoracic impedance of a portion of the subject, cause a second portion of the one or more sensors to detect heart sounds of the subject, generate representations of the detected thoracic impedance, and generate representations of the detected heart sounds.

Example 75 may include the device of example 74, wherein one or more measurement modules are further to fuse the representations of the detected thoracic impedance and the representations of the detected heart sounds to produce fused data, and provide the fused data to a cloud system for analysis.

Example 76 may include the device of example 74, wherein the one or more sensors comprise one or more electrodes and a sound sensor.

Example 77 may include the device of example 74, wherein the one or more measurement modules includes connection switching circuitry to selectively couple other modules of the one or more measurement modules to the one or more sensors to detect the thoracic impedance and to detect the heart sounds.

Example 78 may include a base station for storage of a device for measuring health characteristics of a subject, comprising a housing to which to mount the device for storage, and electronics within the housing, the electronics to retrieve data from the device when coupled to the device, and provide the data to a cloud system for analysis.

Example 79 may include the base station of example 78, wherein the housing has a contoured portion to receive the device for storage.

Example 80 may include the base station of example 79, wherein the housing includes a first piece and a second piece, the second piece coupled to the first piece via a hinge, wherein the contoured portion is located within the first piece, and wherein the second piece is to rotate about the hinge against the first piece to enclose the device within the housing.

Example 81 may include the base station of example 79, wherein the electronics include a connector that abuts the contoured portion, wherein the connector couples the electronics to the device when the device is positioned in the contoured portion.

Example 82 may include the base station of example 78, wherein the electronics include one or more indicators, wherein the one or more indicators are to indicate when the electronics are retrieving the data from the device and when the electronics are providing the data to the cloud system.

Example 83 may include the base station of example 78, wherein the electronics further comprise a connection port located at a surface of the housing, wherein the connection port is to facilitate coupling of the electronics with the device.

Example 84 may include the base station of example 78, wherein the base station further comprises an arm coupled to the housing, wherein the arm extends along a surface of the housing, and wherein the device is to be maintained between the arm and the surface of the housing when the device is mounted to the housing.

Example 85 may include the base station of example 84, wherein the arm comprises an offset portion, wherein the offset portion is to contact the device when the device is mounted to the housing and to apply pressure to the device to maintain a position of the device when the device is mounted to the housing.

Example 86 may include the base station of example 78, wherein the electronics are further to charge the device when the device is coupled to the electronics.

Example 87 may include the base station of example 78, further comprising a cover rotatably coupled to the housing, wherein the cover is to rotate between a first position and a second position, wherein the cover is to cover a portion of the device when the device is mounted to the housing and the cover is in the first position, and wherein the cover is to support the housing on a surface when the housing is placed on the surface and the cover is in the second position.

Example 88 may include a guide for positioning a wearable device for measuring health characteristics of a subject, comprising a first portion to be positioned around a neck of the subject, the first portion to support the guide around the neck of the subject when positioned around the neck of the subject, and a second portion located at an opposite end of the guide from the first portion, the second portion to engage with the wearable device to indicate a proper position for the wearable device on the subject.

Example 89 may include the guide of example 88, wherein the first portion comprises a neck piece that is to be positioned around the neck of the subject, wherein the second portion comprises a positioning piece, wherein the neck piece comprises a first mounting portion and the positioning piece comprises a second mounting portion, the second mounting portion to adjustably mount the positioning piece to the first mounting portion of the positioning piece, and wherein a position that the second mounting portion is mounted to the first mounting portion can be adjusted to provide the proper position for the wearable device on the subject.

Example 90 may include the guide of example 89, wherein an edge of the positioning piece is to abut a portion of the wearable device to indicate the proper position for the wearable device on the subject.

Example 91 may include the guide of example 89, wherein the neck piece includes a first positioning element located on a first side of the neck piece and a second positioning element located on a second side of the neck piece, the second side opposite to the first side, wherein the first positioning element is to contact a first portion of the neck of the subject and the second positioning element is to contact a second portion of the neck of the subject to center the neck piece around the neck of the subject.

Example 92 may include the guide of example 88, wherein the first portion comprises a hook portion, wherein the second portion comprises a socket, where the socket is located toward an opposite end of the guide from the hook portion, and wherein the socket is to engage with a portion of the wearable device to indicate the proper position for the wearable device on the subject.

Example 93 may include one or more computer-readable media having instructions stored thereon, wherein the instructions, when executed by a computer device, cause the computer device to identify one or more health characteristics for a subject, the one or more health characteristics determined from measurements captured from the subject, compare the one or more health characteristics with threshold values corresponding to one or more health warnings, and determine whether to display an attention indicator with an indicator of the subject in a list of subjects based on the comparison of the one or more health characteristics with the threshold values.

Example 94 may include the one or more computer-readable media of example 93, wherein to determine whether to display the attention indicator comprises to determine to display the attention indicator based on the comparison of the one or more health characteristics with the threshold values, and wherein the instructions further cause the computer device to display the list of subjects on a display of the computer device with the attention indicator by the indicator of the subject.

Example 95 may include the one or more computer-readable media of example 94, wherein the instructions, when executed by the computer device, further cause the computer device to display the indicator of the subject at a top of the list of subjects based on the determination to display the attention indicator with the indicator of the subject.

Example 96 may include the one or more computer-readable media of example 93, wherein the measurements captured from the subject include one or more heart sounds of the subject or a thoracic impedance of a portion of a body of the subject.

Example 97 may include the one or more computer-readable media of example 93, wherein the instructions, when executed by the computer device, further cause the computer device to perform a user authentication of a user of the computer device, wherein the list of subjects include subjects associated with a result of the user authentication.

Example 98 may include the one or more computer-readable media of example 93, wherein the instructions, when executed by the computer device, further cause the computer device to detect a user interaction with the indicator of the subject when displayed on a display of the computer device, and display at least a portion of the one or more health characteristics on the display of the computer device in response to detection of the user interaction.

Example 99 may include one or more computer-readable media having instructions stored thereon, wherein the instructions, when executed by a computer device, cause the computer device to identify a display action indicated by an input of a user of the computer device, identify one or more characteristics input by the user, identify one or more threshold values input by the user, each of the one or more threshold values corresponding to a corresponding characteristic of the one or more characteristics, and generate one or more equations based on the one or more characteristics and the one or more threshold values, wherein the display action is to be performed when at least a portion of the one or more equations are satisfied.

Example 100 may include the one or more computer-readable media of example 99, wherein the instructions, when executed by computer device, further cause the computer device to identify one or more relationships input by the user, the one or more relationships corresponding to the one or more characteristics and defining relationships for the one or more threshold values corresponding to the one or more characteristics, wherein the one or more equations are further based on the one or more relationships.

Example 101 may include the one or more computer-readable media of example 99, wherein the instructions, when executed by the computer device, further cause the computer device to utilize health characteristics to determine whether the at least the portion of the one or more equations are satisfied, and perform the display action in response to a determination that the at least the portion of the one or more equations are satisfied.

It will be appreciated by those of ordinary skill in the art that modifications to and variations of the above-described systems, apparatus, and methods may be made without departing from the inventive concepts disclosed herein. Accordingly, the present application should not be viewed as limited except as by the scope and spirit of the appended summary of important aspects.

What is claimed is:

1. A device for capturing measurements related to health of a subject, comprising:

a frame to be removably directly affixed to the chest of the subject at a defined position and in contact with skin of the subject, the frame having a main body that is elongated, a first extension that extends from the main body at a first end of the main body, and a second extension that extends from the main body at a second end of the main body, the first extension and the second extension spaced apart by a distance that spans a lung of the subject;

a first electrode mounted to the first extension, the first electrode to apply an electrical potential to the subject;

a second electrode mounted to the second extension, the second electrode to detect a disturbance caused by the electrical potential being applied; and a sound sensor mounted to the first extension or the second extension, with the sound sensor positioned on the first extension or the second extension to cover an area over the heart of the subject at the defined position, the sound sensor to detect heart sounds of the subject.

2. The device of claim 1, further comprising a control module mounted to the frame and coupled to the second electrode and the sound sensor, the control module to:

receive first data related to the disturbance from the second electrode;

receive second data related to the heart sounds from the sound sensor; and fuse the first data and the second data to produce fused data.

3. The device of claim 2, wherein the control module is further coupled to the first electrode, the control module to cause the first electrode to apply the electrical potential.

4. The device of claim 2, wherein the control module includes one or more indicators, and wherein the control module causes the one or more indicators to provide an indication of a status of the device.

5. The device of claim 1, wherein the electrical potential is a first electrical potential and the disturbance is a first disturbance, and wherein the device further comprises:

a third electrode mounted to the first extension, the third electrode to apply a second electrical potential to the subject; and a fourth electrode mounted to the second extension, the fourth electrode to detect a second disturbance caused by the second electrical potential being applied.

6. The device of claim 5, wherein a first vector is formed between the first electrode and the second electrode, wherein a second vector is formed between the third electrode and the fourth electrode, wherein the second vector is located above the first vector when the device is positioned on the skin of the subject.

7. The device of claim 1, further comprising a reference electrode mounted to the frame, the reference electrode to detect a potential of a body of the subject.

8. The device of claim 7, further comprising:

a control module mounted to the frame and coupled to the second electrode and the reference electrode, the control module to:

receive first data related to the disturbance from the second electrode and second data related to the potential of the body front the reference electrode; and utilize the second data to facilitate processing of the first data.

9. The device of claim 1, further comprising a temperature sensor mounted to the frame, the temperature sensor to detect a temperature of the subject.

10. The device of claim 1, further comprising a combination sensor mounted to the frame, the combination sensor having a reference electrode for detecting a potential of a body of the subject and a temperature sensor for detecting a temperature of the subject.

* * * * *